US009963522B2

(12) United States Patent
Suzuki et al.

(10) Patent No.: US 9,963,522 B2
(45) Date of Patent: May 8, 2018

(54) METALLOCENE COMPLEX AND METHOD FOR PRODUCING OLEFIN POLYMER

(71) Applicant: JAPAN POLYPROPYLENE CORPORATION, Tokyo (JP)

(72) Inventors: Toshinori Suzuki, Mie (JP); Masami Kashimoto, Kanagawa (JP); Masato Nakano, Mie (JP); Hideshi Uchino, Mie (JP); Takao Tayano, Mie (JP)

(73) Assignee: JAPAN POLYPROPYLENE CORPORATION, Tokyo (JP)

(*) Notice: Subject to any disclaimer, the term of this patent is extended or adjusted under 35 U.S.C. 154(b) by 0 days. days.

(21) Appl. No.: 15/126,344

(22) PCT Filed: Mar. 17, 2015

(86) PCT No.: PCT/JP2015/057893
§ 371 (c)(1),
(2) Date: Sep. 15, 2016

(87) PCT Pub. No.: WO2015/141675
PCT Pub. Date: Sep. 24, 2015

(65) Prior Publication Data
US 2017/0081431 A1 Mar. 23, 2017

(30) Foreign Application Priority Data

Mar. 20, 2014 (JP) .................................. 2014-057557

(51) Int. Cl.
*C07F 17/00* (2006.01)
*C08F 4/6592* (2006.01)
*C08F 10/06* (2006.01)
*C08F 210/06* (2006.01)
*C08F 4/659* (2006.01)
*C08F 10/00* (2006.01)

(52) U.S. Cl.
CPC .......... *C08F 4/65916* (2013.01); *C07F 17/00* (2013.01); *C08F 4/65927* (2013.01); *C08F 10/00* (2013.01); *C08F 4/65912* (2013.01); *C08F 2420/06* (2013.01)

(58) Field of Classification Search
CPC .............................. C07F 17/00; C08F 4/65927
See application file for complete search history.

(56) References Cited

U.S. PATENT DOCUMENTS

| 7,019,157 B2* | 3/2006 | Uwai ...................... C07F 17/00 526/161 |
| 2004/0152851 A1 | 8/2004 | Weng et al. |
| 2010/0227987 A1* | 9/2010 | Ito ........................... C08F 10/06 526/114 |
| 2011/0230622 A1 | 9/2011 | Nakano et al. |

FOREIGN PATENT DOCUMENTS

| CN | 102245620 A | 11/2011 |
| EP | 2360163 A1 | 8/2011 |
| JP | 4-337308 A | 11/1992 |
| JP | 6-287257 A | 10/1994 |
| JP | 8-239416 A | 9/1996 |
| JP | 11-240909 A | 9/1999 |
| JP | 2003-206325 A | 7/2003 |
| JP | 2004-502698 A | 1/2004 |
| JP | 2007-517961 A | 7/2007 |
| JP | 2010-163423 A | 7/2010 |
| JP | 2012-6903 A | 1/2012 |
| JP | 2012-121882 A | 6/2012 |
| JP | 2013-124228 A | 6/2013 |
| JP | 2014-193846 A | 10/2014 |
| RU | 2160276 C1 | 12/2000 |
| RU | 2160277 C1 | 12/2000 |
| WO | 02/02575 A1 | 1/2002 |

OTHER PUBLICATIONS

European Search Report issued with respect to Application No. 15764920.3, dated Feb. 15, 2017.
Yong-Woo Shin et al., "Synthesis and characterization of ethylene-propylene random copolymers with isotactic propylene sequence", Polymer 42, 2001, pp. 9611-9615.
International Search Report issued with respect to application No. PCT/JP2015/057893, dated Jun. 16, 2015.
International Preliminary Report on Patentability issued with respect to application No. PCT/JP2015/057893, dated Sep. 20, 2016.
Chinese Office Action from Application No. 201580015221.9 dated Jan. 25, 2018.
Notification of Reasons for Refusal from Japanese Application No. 2015-053494, dated Feb. 26, 2018, with English machine translation.

* cited by examiner

*Primary Examiner* — Caixia C Lu
(74) *Attorney, Agent, or Firm* — Greenblum & Bernstein, P.L.C.

(57) ABSTRACT

The present invention provides a metallocene complex capable of producing a homopolypropylene having a high melting point in the homopolymerization of propylene, and a production method of an olefin polymer using the same. The metallocene complex of the present invention is represented by formula [I].

12 Claims, No Drawings

METALLOCENE COMPLEX AND METHOD FOR PRODUCING OLEFIN POLYMER

TECHNICAL FIELD

The present invention relates to a novel metallocene complex and a production method of an olefin polymer. More specifically, the present invention relates to a novel metallocene complex having a substituent introduced into a specific position, which can produce a high-melting-point polypropylene and in the copolymerization of propylene and ethylene, can provide a high ethylene uptake efficiency and produce an ethylene-propylene copolymerized rubber component with high activity, and a production method of an olefin polymer.

BACKGROUND ART

Crystalline polypropylene is excellent in mechanical property, chemical resistance, etc. and therefore, is widely used in various molding fields. However, a homopolymer of propylene or a random copolymer with a small amount of α-olefin sometimes lacks impact resistance, though its rigidity is high.

To cope with this problem, attempts have been made to improve the impact resistance by a method of adding a rubber component such as ethylene-propylene copolymer (EPR) to a propylene homopolymer or by the production of a so-called impact copolymer where a rubber component is incorporated by copolymerizing propylene and ethylene or α-olefin continuously after the homopolymerization of propylene. Furthermore, flexibility and impact resistance can be enhanced by increasing the amount of a rubber component in the impact copolymer.

As another problem, in an impact copolymer obtained by the polymerization in the presence of a conventional Ziegler-Natta catalyst, a low-molecular-weight component (an oligomer component, etc.) is present by the nature of the catalyst. Particularly, in recent years, there is a tendency to more improve the moldability of the obtained impact copolymer by increasing the flowability.

However, when the flowability of the rubber moiety is raised too much, this is accompanied also by an increase in the production rate of a low-molecular-weight component, and the low-molecular-weight component is known not only to give rise to generation of fume, bad smell, etc. during processing but also to, even after processing, adversely affect the odor or taste and cause various problems such as change for the worse in the blocking property due to sticking. Deterioration of powder properties of the polymerized polymer disadvantageously makes stable production impossible. On the other hand, when the difference in the average molecular weight between crystalline polypropylene and rubber moiety becomes large, a problem such as increased incidence of gels in a molded article or high coefficient of linear expansion of a molded article is caused.

Meanwhile, it is known that isotactic polypropylene is obtained by polymerizing propylene with use of a metallocene-based catalyst different from the conventional Ziegler-Natta catalyst. It is also known that an impact copolymer is produced by copolymerizing ethylene and propylene with use of a similar catalyst continuously after the homopolymerization of propylene (see, for example, Patent Documents 1 and 2). An impact copolymer having good rigidity and good impact resistance is also disclosed (see, for example, Patent Document 3).

Among others, the impact copolymer needs to exhibit, for example, a lower glass transition temperature so as to develop high impact resistance and for satisfying this requirement, it is supposed that copolymerization of propylene and ethylene or α-olefin is preferably performed to let each content satisfy a certain range (see, for example, Non-Patent Document 1).

As for the transition metal compound constituting the above-described metallocene-base catalyst, many examples have been already known. Above all, in order to improve the rigidity of an impact copolymer, a transition metal compound capable of providing a homopolypropylene having a high melting point has also been already known (see, for example, Patent Document 4).

However, the production of such a propylene-based impact copolymer by the use of a metallocene-based catalyst involves the following technical problems due to difference in the reactivity of propylene with other comonomers.

When copolymerization of propylene and ethylene or α-olefin is performed after the homopolymerization of propylene according to the conventional production method by using a metallocene-based catalyst, the gas composition ratio of propylene/(ethylene or α-olefin) in the polymerization atmosphere greatly differs from the polymerization amount ratio of propylene amount/(ethylene or α-olefin amount) polymerized in this atmosphere, and the polymerization amount of (ethylene or α-olefin) in the polymer sometimes decreases. That is, in order to obtain a copolymer having a desired ethylene or α-olefin content, polymerization must be performed by feeding a gas having a monomer ratio greatly different from the contents in a copolymer, which involves a production problem. In an extreme case, a copolymer having desired contents cannot be produced due to restriction of the polymerization apparatus.

In this way, a catalyst using a metallocene complex produces a large difference in the ethylene content between an ethylene/propylene mixed gas and a polymer, and it is demanded to develop a production method where the difference is eliminated and the uptake efficiency of ethylene and α-olefin is high.

In addition, in the case of using a so-far known metallocene catalyst, there is a problem that when copolymerization of propylene and ethylene or α-olefin is performed in gas phase, the molecular weight of the obtained copolymer is low. In a propylene-base impact copolymer, the molecular weight of the copolymer must have a value not less than a certain level so as to develop high impact resistance, and a production method capable of producing a copolymer having a high molecular weight is demanded as well. Furthermore, development of a catalyst with high rubber activity is also demanded for the purpose of reducing the catalyst cost per unit polymer or increasing the content of rubber moiety.

As described above, in order to enhance the rigidity of an impact copolymer, a homopolypropylene having a high melting point is required. However, as far as a catalyst using a metallocene complex is concerned, in the above-described catalyst capable of enhancing the uptake efficiency of ethylene and α-olefin and producing a copolymer having a high molecular weight, a catalyst exerting a sufficient performance as a catalyst capable of producing a homopolypropylene having a high melting point is not yet known.

Patent Document 5 discloses a metallocene complex having a substituent on the 5-position of an indenyl ring and having, on the 2-position of an indenyl ring, a furyl or thienyl group that may have a substituent, and a metallocene complex with which a relatively high ethylene uptake efficiency and a copolymer having a high molecular weight can be provided, is disclosed.

Patent Document 6 discloses a metallocene complex having a cyclic-structure substituent between the 5-position and the 6-position of an indenyl ring and having, on the 2-position of an indenyl group, a furyl or thienyl group that may have a substituent, and a metallocene complex with which a relatively high ethylene uptake efficiency and a copolymer having a high molecular weight can be provided, is disclosed.

However, the metallocene complexes disclosed in Patent Documents 5 and 6 do not have a sufficiently high performance in terms of activity, and creation of a higher-performance metallocene complex is demanded. The melting point is also preferably higher, because the rigidity can be enhanced.

PRIOR ART LITERATURE

Patent Document

Patent Document 1: JP-A-4-337308 (the term "JP-A" as used herein means an "unexamined published Japanese patent application")
Patent Document 2: JP-A-6-287257
Patent Document 3: JP-A-2003-206325
Patent Document 4: JP-A-11-240909
Patent Document 5: JP-A-2010-163423
Patent Document 6: JP-A-2012-121882

Non-Patent Document

Non-Patent Document 1: Polymer, 2001, Vol. 42, page 9611

SUMMARY OF THE INVENTION

Problems that the Invention is to Solve

Considering the problems in the above-described conventional techniques, an object of the present invention is to provide a metallocene complex that exhibits a higher uptake efficiency of ethylene and α-olefin comonomers in the copolymerization of an olefin containing propylene as a monomer than conventional metallocene catalysts, can polymerize a homopolypropylene and a rubber component with high activity, and in the homopolymerization of propylene, can produce a homopolypropylene having a high melting point, and a production method of an olefin polymer using the same.

Means for Solving the Problems

As a result of a variety of studies to solve the above-described problems, the present inventors have made versatile examinations and experimental searches on the ligand structure of a transition metal compound as a metallocene complex in a metallocene-based polymerization catalyst with an attempt to complete a technique for increasing (i) the uptake efficiency of ethylene and α-olefin and enhancing (ii) the activity and in addition, to obtain (iii) a homopolypropylene having a high melting point by performing highly stereoregular polymerization of a propylene monomer in the homopolymerization of propylene, while respecting the empirical rules in light of symmetry attributable to a basic skeleton, the mechanism of polymer formation at a catalytic active site, and the steric effect and electronic effect of a substituent on a coordinated monomer or a growing polymer, and have found in the process thereof that when a transition metal compound having a specific steric structure is formed, a catalytic function expressing all of the above-described three catalytic performances in a balanced manner is manifested, and reached the present invention.

More specifically, in order to attain the object above, the present inventors have discovered a metallocene complex having a specific substituent, particularly, a metallocene complex configured to place a substituent having a cyclic structure on the carbon atom, silicon atom or germanium atom crosslinking two indenyl ring moieties, have a substituent also on the 5-position of an indenyl ring, and have, on the 2-position of an indenyl ring, a furyl group that may have a substituent, or a thienyl group that may have a substituent. The present invention has been accomplished based on these findings.

That is, according to a first aspect of the present invention, a metallocene complex represented by the following formula [I] is provided.

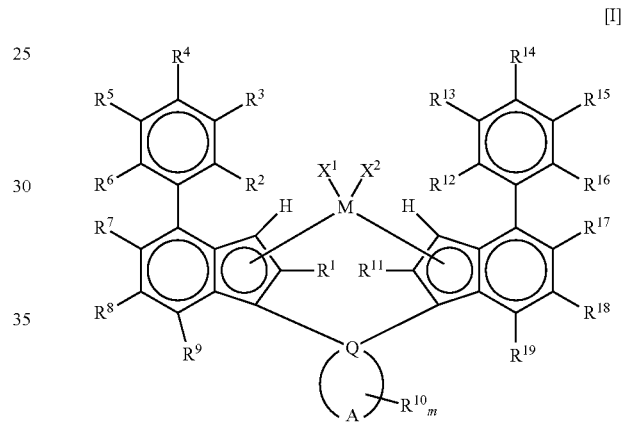

[I]

(in formula [I], M is Ti, Zr or Hf; Q is a carbon atom, a silicon atom or a germanium atom; each of $X^1$ and $X^2$ is independently a halogen atom, an alkyl group having a carbon number of 1 to 6, an aryl group having a carbon number of 6 to 18, an amino group substituted with an alkyl group having a carbon number of 1 to 6, an alkoxy group having a carbon number of 1 to 6, a halogen-containing alkyl group having a carbon number of 1 to 6, or a halogen-containing aryl group having a carbon number of 6 to 18; $R^1$ and $R^{11}$ may be the same or different and are a hydrogen atom, an alkyl group having a carbon number of 1 to 6, an alkoxy group having a carbon number of 1 to 6, a furyl group, a thienyl group, a furyl group having a substituent, or a thienyl group having a substituent, and one or both of $R^1$ and $R^{11}$ are inevitably any of a furyl group, a thienyl group, a furyl group having a substituent, or a thienyl group having a substituent; $R^7$ and $R^{17}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18, and when either one of $R^7$ and $R^{17}$ is a hydrogen atom, the other is a substituent except for a hydrogen atom;

$R^8$ and $R^{18}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18; adjacent substituents out of $R^7$, $R^8$, $R^{17}$ and $R^{18}$ may bilaterally constitute a 5- to 7-membered ring, and the 5- to 7-membered ring may contain an unsaturated bond; $R^2$, $R^3$, $R^4$, $R^5$, $R^6$, $R^9$, $R^{12}$, $R^{13}$, $R^{14}$, $R^{15}$, $R^{16}$ and $R^{19}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, an aryl group having a carbon number of 6 to 18, a halogen-containing aryl group having a carbon number of 6 to 18, a furyl group, a thienyl group, a furyl group having a substituent, or a thienyl group having a substituent; adjacent substituents out of $R^2$, $R^3$, $R^4$, $R^5$, $R^6$, $R^{12}$, $R^{13}$, $R^{14}$, $R^{15}$ and $R^{16}$ may bilaterally constitute a 5- to 7-membered ring, and the 5- to 7-membered ring may contain an unsaturated bond; A is a divalent hydrocarbon group having a carbon number of 3 to 12 and forming a ring together with Q to which it is bonded, and may contain an unsaturated bond; $R^{10}$ is a substituent on A and is an alkyl group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18; and m represents an integer of 0 to 24, and when m is 2 or more, $R^{10}$s may combine with each other to form a new ring structure).

According to a second aspect of the present invention, the metallocene complex of the first aspect, wherein in the formula [I], $R^7$ and $R^{17}$ may be the same or different and are an alkyl group having a carbon number of 1 to 6, is provided.

According to a third aspect of the present invention, the metallocene complex of the first or second aspect, wherein in the formula [I], $R^8$ and $R^{18}$ may be the same or different and are an alkyl group having a carbon number of 1 to 6, is provided.

According to a fourth aspect of the present invention, the metallocene complex of any one of the first to third aspects, wherein in the formula [I], A is a divalent hydrocarbon group having a carbon number of 3 to 6 and forms a 4- to 7-membered ring and m is an integer of 0 to 6, is provided.

According to a fifth aspect of the present invention, the metallocene complex of any one of the first to fourth aspects, wherein in the formula [I], $R^2$, $R^6$, $R^9$, $R^{12}$, $R^{16}$ and $R^{19}$ are a hydrogen atom, is provided.

According to a sixth aspect of the present invention, the metallocene complex of any one of the first to fifth aspects, wherein the formula [I] is represented by the following formula [II], is provided:

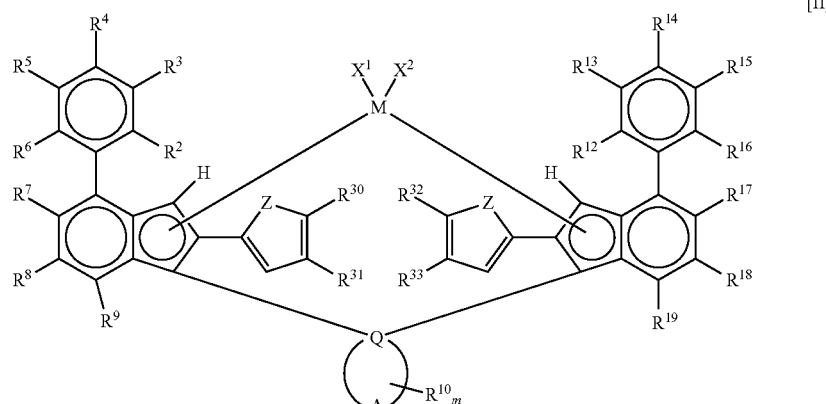

(in formula [II], Z is an oxygen atom or a sulfur atom, $R^{30}$, $R^{31}$, $R^{32}$ and $R^{33}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a silyl group containing a hydrocarbon group having a carbon number of 1 to 6, or an aryl group having a carbon number of 6 to 18, adjacent substituents out of $R^{30}$, $R^{31}$, $R^{32}$ and $R^{33}$ may bilaterally constitute a 5- to 7-membered ring, the 5- to 7-membered ring may contain an unsaturated bond, and each of M, $X^1$, $X^2$, Q, $R^2$ to $R^{10}$, $R^{12}$ to $R^{19}$ and m has the same meaning as in formula [I]).

According to a seventh aspect of the present invention, a catalyst for olefin polymerization, comprising the metallocene complex of any one of the first to sixth aspects, is provided.

According to an eighth aspect of the present invention, the catalyst for olefin polymerization of the seventh aspect, comprising each of the following components (A), (B) and (C), is provided:

component (A): the metallocene complex according to any one of the first to sixth aspects, component (B): a compound reacting with the component (A) to form an ion pair, or an ion-exchange layered silicate, and component (C): an organoaluminum compound.

According to a ninth aspect of the present invention, the catalyst for olefin polymerization of the eighth aspect, wherein the component (B) is an ion-exchange layered silicate, is provided.

According to a tenth aspect of the present invention, a method for producing an olefin polymer, comprising performing a polymerization or copolymerization of olefin by using the catalyst for olefin polymerization of any one of the seventh to ninth aspects, is provided.

According to an eleventh aspect of the present invention, a method for producing a propylene-based polymer by using the catalyst for olefin polymerization according to any one of the seventh to ninth aspects, is provided, which comprises:

(i) a step of polymerizing propylene in a ratio of 90 to 100 wt % and ethylene or α-olefin in a ratio of 0 to 10 wt %, relative to all monomer components; and (ii) a step of polymerizing propylene in a ratio of 10 to 90 wt % and ethylene and/or α-olefin having a carbon number of 4 or more in a ratio of 10 to 90 wt %, relative to all monomer components.

According to a twelfth aspect of the present invention, a method for producing a propylene-based polymer by using the catalyst for olefin polymerization according to any one of the seventh to ninth aspects is provided, which comprises:

(i) a first step of polymerizing propylene in a ratio of 90 to 100 wt % and ethylene or α-olefin in a ratio of 0 to 10 wt %, relative to all monomer components, by bulk polymerization using propylene as a solvent or gas phase polymerization of maintaining the monomers in a gas state; and (ii) a second step of gas phase polymerizing propylene in a ratio of 10 to 90 wt % and ethylene or α-olefin in a ratio of 10 to 90 wt %, relative to all monomer components.

Advantage of the Invention

By using the metallocene complex of the present invention as a polymerization catalyst, a high uptake efficiency of ethylene or α-olefin is achieved, compared with conventional metallocene compounds, and this makes it possible to produce a homopolypropylene with high activity, particularly, an ethylene/propylene copolymer with high activity. Furthermore, a homopolypropylene having a high melting point can be produced in the homopolymerization of propylene.

Consequently, a propylene-based polymer excellent in flexibility or impact resistance and having high rigidity can be efficiently produced, and the novel metallocene complex and the production method of an olefin polymer of the present invention are very useful from the industrial viewpoint. For example, in the case of a propylene/α-olefin block copolymer produced by multistage polymerization of a polypropylene component and a propylene.α-olefin copolymer component, the efficiency in uptaking a polypropylene component having high rigidity and α-olefin is high and since high-activity polymerizations of a homopolypropylene and a propylene.α-olefin copolymer can be achieved at the same time, a propylene.α-olefin block copolymer in which the rigidity and the impact resistance are improved in a balanced manner can be obtained with good productivity.

The advantages of the present invention provided by the metallocene complex according to the present invention is discussed below.

The metallocene complex constituting a basic configuration of the present invention is a novel transition metal compound characterized by the electronic and steric structures of ligands thereof and develops a catalytic function of providing a good uptake efficiency of ethylene and α-olefin, enabling high-activity polymerizations of homopolypropylene and a propylene.α-olefin copolymer, and producing a homopolypropylene having a high melting point in the homopolymerization of propylene.

The metallocene complex is composed of a transition metal compound having a structure represented by formula [I] and in the present invention, is used as a catalyst component of a catalyst for olefin polymerization and combined with a co-catalyst, etc. to form a catalyst for α-olefin polymerization.

As demonstrated by comparison between Examples and Comparative Examples described later, using the transition metal compound of the present invention as a catalyst component for olefin polymerization makes it possible to realize a metallocene catalyst for α-olefin polymerization, which provides a good uptake efficiency of ethylene and α-olefin, enables polymerizations of a homopolypropylene and a propylene.α-olefin copolymer with high activity, and affords a homopolypropylene having a higher melting point in the homopolymerization of propylene.

The reason therefor is not necessarily clarified, but the transition metal compound represented by formula [I] in the present invention is fundamentally characterized by a specific structure configured to place a substituent having a cyclic structure on the carbon atom, silicon atom or germanium atom crosslinking two indenyl ring moieties, have a substituent also on the 5-position of an indenyl ring, and have, on the 2-position of an indenyl ring, a furyl group that may have a substituent, or a thienyl group that may have a substituent, and it is presumed that the specificity of the present invention is achieved by these characteristics.

In particular, it is believed that the configuration of arranging a substituent on the 5-position of an indenyl ring and making the crosslinking part cyclic brings about optimization of an angle of two indenyl rings and allows for appropriate adjustment of the angle between a furyl group, etc. at the 2-position of an indenyl group and the indenyl ring, enabling the furyl group, etc. to express an optimal steric effect on the coordination field.

The steric effect of a substituent such as furyl group at the 2-position of an indenyl ring is considered to make selective propylene coordination possible in the propylene insertion reaction and produce an excellent effect of causing highly stereoregular polymerization.

MODE FOR CARRYING OUT THE INVENTION

The metallocene complex of the present invention and a method for producing a propylene-based polymer by using the metallocene complex (or a metallocene compound) are described in detail below item by item.

1. Metallocene Complex

The metallocene complex of the present invention is a metallocene complex having specific substituents, represented by the following formula [I]:

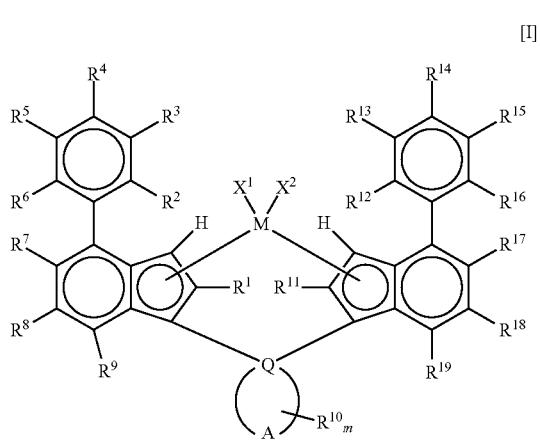

[I]

(in formula [I], M is Ti, Zr or Hf; Q is a carbon atom, a silicon atom or a germanium atom; each of $X^1$ and $X^2$ is independently a halogen atom, an alkyl group having a carbon number of 1 to 6, an aryl group having a carbon number of 6 to 18, an amino group substituted with an alkyl group having a carbon number of 1 to 6, an alkoxy group having a carbon number of 1 to 6, a halogen-containing alkyl group having a carbon number of 1 to 6, or a halogen-containing aryl group having a carbon number of 6 to 18; $R^1$ and $R^{11}$ may be the same or different and are a hydrogen atom, an alkyl group having a carbon number of 1 to 6, an alkoxy group having a carbon number of 1 to 6, a furyl group, a thienyl group, a furyl group having a substituent, or a thienyl group having a substituent, and one or both of $R^1$ and $R^{11}$ are inevitably any of a furyl group, a thienyl group, a furyl group having a substituent, or a thienyl group having a substituent; $R^7$ and $R^{17}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18, and when either one of $R^7$ and $R^{17}$ is a hydrogen atom, the other is a substituent except for a hydrogen atom; $R^8$ and $R^{18}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18; adjacent substituents out of $R^7$, $R^8$, $R^{17}$ and $R^{18}$ may bilaterally constitute a 5- to 7-membered ring, and the 5- to 7-membered ring may contain an unsaturated bond; $R^2$, $R^3$, $R^4$, $R^5$, $R^6$, $R^9$, $R^{12}$, $R^{13}$, $R^{14}$, $R^{15}$, $R^{16}$ and $R^{19}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, an aryl group having a carbon number of 6 to 18, a halogen-containing aryl group having a carbon number of 6 to 18, a furyl group, a thienyl group, a furyl group having a substituent, or a thienyl group having a substituent; adjacent substituents out of $R^2$, $R^3$, $R^4$, $R^5$, $R^6$, $R^{12}$, $R^{13}$, $R^{14}$, $R^{15}$, and $R^{16}$ may bilaterally constitute a 5- to 7-membered ring, and the 5- to 7-membered ring may contain an unsaturated bond; A is a divalent hydrocarbon group having a carbon number of 3 to 12 and forming a ring together with Q to which it is bonded, and may contain an unsaturated bond; $R^{10}$ is a substituent on A and is an alkyl group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18; and m represents an integer of 0 to 24, and when m is 2 or more, $R^{10}$s may combine with each other to form a new ring structure).

In formula [I], specific examples of the alkyl group having a carbon number of 1 to 6 include a methyl group, an ethyl group, an n-propyl group, an i-propyl group, an n-butyl group, an i-butyl group, an s-butyl group, a tert-butyl group, an n-pentyl group, an n-hexyl group, a cyclopropyl group, a cyclopentyl group, and a cyclohexyl group.

Specific examples of the alkoxy group having a carbon number of 1 to 6 include a methoxy group, an ethoxy group, an n-propoxy group, an i-propoxy group, an n-butoxy group, an i-butoxy group, a tert-butoxy group, and a phenoxy group.

The aryl group having a carbon number of 6 to 18 may be substituted with a hydrocarbon group having a carbon number of 1 to 6, and specific examples of the aryl group include a phenyl group, a tolyl group, a dimethylphenyl group, an ethylphenyl group, a trimethylphenyl group, a tert-butylphenyl group, a di-tert-butylphenyl group, a biphenyl group, a 1-naphthyl group, a 2-naphthyl group, an acenaphthyl group, a phenanthryl group, and an anthryl group.

In formula [I], the halogen atom includes a chlorine atom, a bromine atom, an iodine atom, and a fluorine atom. The amino group substituted with an alkyl group having a carbon number of 1 to 6 includes a dimethylamino group, a diethylamino group, a di-n-propylamino group, a di-i-propylamino group, a methylethylamino group, etc.

The halogen atom in the halogen-containing alkyl group having a carbon number of 1 to 6 includes a fluorine atom, a chlorine atom, a bromine atom, and an iodine atom. The halogen-containing alkyl group having a carbon number of 1 to 6 is an alkyl group where a hydrogen atom on the skeleton of an alkyl group having a carbon number of 1 to 6 is replaced by a halogen atom. Specific examples thereof include a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a 2,2,2-trifluoroethyl group, a 2,2,1,1-tetrafluoroethyl group, a pentafluoroethyl group, a pentachloroethyl group, a pentafluoropropyl group, a nonafluorobutyl group, a 5-chloropentyl group, a 5,5,5-trichloropentyl group, a 5-fluoropentyl group, a 5,5,5-trifluoropentyl group, a 6-chlorohexyl group, a 6,6,6-trichlorohexyl group, a 6-fluorohexyl group, and a 6,6,6-trifluorohexyl group.

In formula [I], the trialkylsilyl group-containing alkyl group having a carbon number of 1 to 6 includes, specifically, a (trimethylsilyl)methyl group, a (triethylsilyl)methyl group, a (tert-butyldimethylsilyl)methyl group, and a (trimethylsilyl)ethyl group.

In formula [I], the silyl group containing a hydrocarbon group having a carbon number of 1 to 6 is a substituent in which three hydrocarbon groups each having a carbon number of 1 to 6, which may be different, are substituted on a silicon atom. The hydrocarbon group having a carbon number of 1 to 6 includes an alkyl group having a carbon number of 1 to 6, an alkenyl group having a carbon number of 1 to 6, and a phenyl group, which are recited in formula [I], and a substituent may be present on the phenyl group. Specific examples of the silyl group include a trimethylsilyl group, a triethylsilyl group, a tri-n-butylsilyl group, a tert-butyldimethylsilyl group, a trivinylsilyl group, a triallylsilyl group, and a triphenylsilyl group.

In formula [I], the halogen-containing aryl group having a carbon number of 6 to 18 is specifically, for example, an aryl group in which a hydrogen atom of the above-described aryl group having a carbon number of 6 to 18 is replaced by a halogen atom, and specific examples thereof include 2-, 3- and 4-substituted fluorophenyl groups, 2-, 3- and 4-substituted chlorophenyl groups, 2-, 3- and 4-substituted bromophenyl groups, 2,4-, 2,5-, 2,6-, and 3,5-substituted difluorophenyl groups, 2,4-, 2,5-, 2,6-, and 3,5-substituted dichlorophenyl groups, 2,4,6-, 2,3,4-, 2,4,5-, and 3,4,5-substituted trifluorophenyl groups, 2,4,6-, 2,3,4-, 2,4,5-, and 3,4,5-substituted trichlorophenyl groups, a pentafluorophenyl group, a pentachlorophenyl group, a 3,5-dimethyl-4-chlorophenyl group, and a 3,5-dichloro-4-biphenyl group.

In formula [I], specific examples of the furyl group, the thienyl group, the furyl group having a substituent, and the thienyl group having a substituent include a 2-furyl group, a 2-(5-methylfuryl) group, a 2-(5-ethylfuryl) group, a 2-(5-n-propylfuryl) group, a 2-(5-i-propylfuryl) group, a 2-(5-tert-butylfuryl) group, a 2-(5-trimethylsilylfuryl) group, a 2-(5-triethylsilylfuryl) group, a 2-(5-phenylfuryl) group, a 2-(5-tolylfuryl) group, a 2-(5-fluorophenylfuryl) group, a 2-(5-chlorophenylfuryl) group, a 2-(4,5-dimethylfuryl) group, a 2-(3,5-dimethylfuryl) group, a 2-benzofuryl group, a 3-furyl group, a 3-(5-methylfuryl) group, a 3-(5-ethylfuryl) group, a 3-(5-n-propylfuryl) group, a 3-(5-i-propylfuryl) group, a 3-(5-tert-butylfuryl) group, a 3-(5-trimethylsilylfuryl) group, a 3-(5-triethylsilylfuryl) group, a 3-(5-phenylfuryl) group, a 3-(5-tolylfuryl) group, a 3-(5-fluorophenylfuryl) group, a 3-(5-chlorophenylfuryl) group, a 3-(4,5-dimethylfuryl) group, a 3-benzofuryl group, a 2-thienyl group, a 2-(5-methylthienyl) group, a 2-(5-ethylthienyl) group, a 2-(5-n-propylthienyl) group, a 2-(5-i-propylthienyl) group, a 2-(5-tert-butylthienyl) group, a 2-(5-trimethylsilylthienyl) group, a 2-(5-triethylsilylthienyl) group, a 2-(5-phenylthienyl) group, a 2-(5-tolylthienyl) group, a 2-(5-fluorophenylthienyl) group, a 2-(5-chlorophenylthienyl) group, a 2-(4,5-dimethylthienyl) group, a 2-(3,5-dimethylthienyl) group, a 2-benzothienyl group, a 3-thienyl group, a 3-(5-methylthienyl) group, a 3-(5-ethylthienyl) group, a 3-(5-n-propylthienyl) group, a 3-(5-i-propylthienyl) group, a 3-(5-tert-butylthienyl) group, a 3-(5-trimethylsilylthienyl) group, a 3-(5-triethylsilylthienyl) group, a 3-(5-phenylthienyl) group, a 3-(5-tolylthienyl) group, a 3-(5-fluorophenylthienyl) group, a 3-(5-chlorophenylthienyl) group, a 3-(4,5-dimethylthienyl) group, and a 3-benzothienyl group.

In formula [I], M is Ti, Zr or Hf, preferably Zr or Hf, more preferably Zr. Q is a carbon atom, a silicon atom or a germanium atom, preferably a silicon atom or a germanium atom.

Each of $X^1$ and $X^2$ is independently a halogen atom, an alkyl group having a carbon number of 1 to 6, an aryl group having a carbon number of 6 to 18, an amino group substituted with an alkyl group having a carbon number of 1 to 6, an alkoxy group having a carbon number of 1 to 6, a halogen-containing alkyl group having a carbon number of 1 to 6, or a halogen-containing aryl group having a carbon number of 6 to 18.

Among these, a halogen atom and a hydrocarbon group having a carbon number of 1 to 6 are preferred, and specifically, a chlorine atom, a bromine atom, an iodine atom, a methyl group, an ethyl group, an i-butyl group, and a phenyl group are more preferred.

$R^7$ and $R^{17}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18, and when either one of $R^7$ and $R^{17}$ is a hydrogen atom, the other is a substituent except for a hydrogen atom. $R^7$ and $R^{17}$ are preferably an alkyl group having a carbon number of 1 to 6 or an alkoxy group having a carbon number of 1 to 6, more preferably an alkyl group having a carbon number of 1 to 6. Among others, $R^7$ and $R^{17}$ are preferably a methyl group.

$R^8$ and $R^{18}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18. $R^8$ and $R^{18}$ are preferably an alkyl group having a carbon number of 1 to 6. Among others, $R^8$ and $R^{18}$ are preferably a methyl group.

Adjacent substituents out of $R^7$, $R^8$, $R^{17}$ and $R^{18}$ may bilaterally constitute a 5- to 7-membered ring, and the 5- to 7-membered ring may contain an unsaturated bond. It is preferable for $R^7$, $R^8$, $R^{17}$ and $R^{18}$ to form a 5- or 6-membered ring.

$R^2$, $R^3$, $R^4$, $R^5$, $R^6$, $R^9$, $R^{12}$, $R^{13}$, $R^{14}$, $R^{15}$, $R^{16}$ and $R^{19}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, an aryl group having a carbon number of 6 to 18, a halogen-containing aryl group having a carbon number of 6 to 18, a furyl group, a thienyl group, a furyl group having a substituent, or a thienyl group having a substituent.

$R^9$ and $R^{19}$, which are a substituent on an indenyl group, are preferably a hydrogen atom, an alkyl group having a carbon number of 1 to 6, or an alkoxy group having a carbon number of 1 to 6, more preferably a hydrogen atom.

$R^2$, $R^3$, $R^4$, $R^5$, $R^6$, $R^{12}$, $R^{13}$, $R^{14}$, $R^{15}$ and $R^{16}$, which are a substituent of a phenyl group on the 4-position of an indenyl group, are preferably a hydrogen atom, a halogen atom, an alkyl group having a carbon number of 1 to 6, a trialkylsilyl group-containing alkyl group having a carbon number of 1 to 6, or an aryl group having a carbon number of 6 to 18. In addition, $R^2$, $R^6$, $R^{12}$ and $R^{16}$ are preferably a hydrogen atom.

Adjacent substituents out of $R^2$, $R^3$, $R^4$, $R^5$, $R^6$, $R^{12}$, $R^{13}$, $R^{14}$, $R^{15}$ and $R^{16}$ may bilaterally constitute a 5- to 7-membered ring, and the 5- to 7-membered ring may contain an unsaturated bond.

Specifically, the substituent on the 4-position of an indenyl ring includes a 1-naphthyl group, a 2-naphthyl group, a 5,6,7,8-tetrahydro-1-naphthyl group, a 5,6,7,8-tetrahydro-2-naphthyl group, a phenanthryl group, an anthryl group, etc.

$R^1$ and $R^{11}$, which are a substituent on the 2-position of an indenyl group, may be the same or different and are a hydrogen atom, an alkyl group having a carbon number of 1 to 6, an alkoxy group having a carbon number of 1 to 6, a furyl group, a thienyl group, a furyl group having a substituent, or a thienyl group having a substituent, and one or both of $R^1$ and $R^{11}$ are inevitably any of a furyl group, a thienyl group, a furyl group having a substituent, or a thienyl group having a substituent.

The substituents $R^1$ and $R^{11}$ are preferably an alkyl group having a carbon number of 1 to 6, a furyl group that may have a substituent, or a thienyl group that may have a substituent. Among the alkyl group having a carbon number of 1 to 6, a methyl group, an ethyl group, an n-propyl group, an n-butyl group, an i-propyl group, and an i-butyl group are preferred, and a methyl group is more preferred.

A furyl group, a thienyl group, a furyl group having a substituent, or a thienyl group having a substituent, recited as the substituents $R^1$ and $R^{11}$, can be more preferably represented by the following formula [III]:

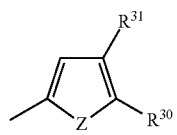

[III]

(in formula [III], Z is an oxygen atom or a sulfur atom, $R^{30}$ and $R^{31}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a silyl group containing a hydrocarbon group having a carbon number of 1 to 6, or an aryl group having a carbon number of 6 to 18, adjacent substituents $R^{30}$ and $R^{31}$ may bilaterally constitute a 5- to 7-membered ring, and the 5- to 7-membered ring may contain an unsaturated bond).

In formula [III], the substituent $R^{31}$ is preferably a hydrogen atom, a halogen atom, an alkyl group having a carbon number of 1 to 6, or an aryl group having a carbon number of 6 to 18, more preferably a hydrogen atom or an alkyl group having a carbon number of 1 to 6. The substituent $R^{30}$ is preferably a halogen atom, an alkyl group having a carbon number of 1 to 6, or an aryl group having a carbon number of 6 to 18, more preferably an alkyl group having a carbon number of 1 to 6 or an aryl group having a carbon number of 6 to 18.

In formula [I], $R^1$ and $R^{11}$ are preferably a furyl group, a thienyl group, a furyl group having a substituent, or a thienyl group having a substituent and in terms of high ethylene uptake efficiency, more preferably a furyl group having a substituent or a thienyl group having a substituent, still more preferably a furyl group having a substituent.

A is a divalent hydrocarbon group having a carbon number of 3 to 12 and forming a ring together with Q to which it is bonded, and may contain an unsaturated bond. A is preferably a divalent hydrocarbon group having a carbon number of 3 to 6 and forming a 4- to 7-membered ring, and A is more preferably a divalent hydrocarbon group having a carbon number of 3 or 4 and forming a 4- or 5-membered ring.

$R^{10}$ is a substituent on A and is an alkyl group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18. $R^{10}$ is preferably an alkyl group having a carbon number of 1 to 6, more preferably a methyl group.

m represents an integer of 0 to 24, and when m is 2 or more, $R^{10}$s may combine with each other to form a new ring structure. m is preferably an integer of 0 to 6, and m is more preferably 0.

The metallocene complex of the present invention is more specifically a metallocene complex having specific substituents, represented by the following formula [II]:

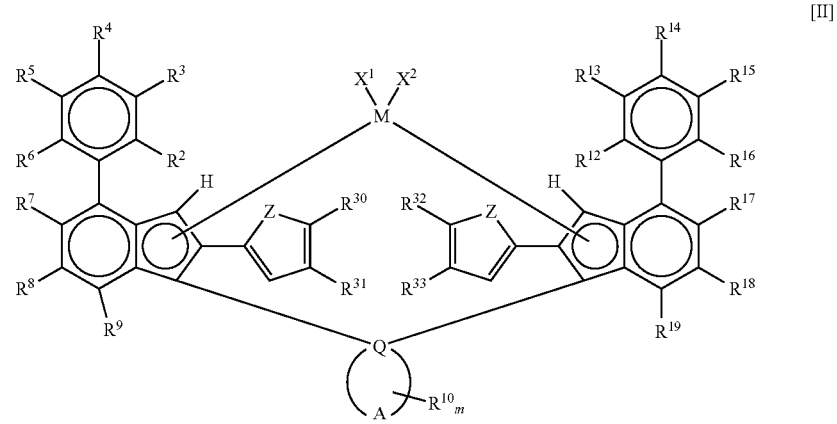

[II]

(in formula [III], Z is an oxygen atom or a sulfur atom, $R^{30}$, $R^{31}$, $R^{32}$ and $R^{33}$ may be the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a silyl group containing a hydrocarbon group having a carbon number of 1 to 6, or an aryl group having a carbon number of 6 to 18, adjacent substituents out of $R^{30}$, $R^{31}$, $R^{32}$ and $R^{33}$ may bilaterally constitute a 5- to 7-membered ring, the 5- to 7-membered ring may contain an unsaturated bond, and each of M, $X^1$, $X^2$, Q, $R^2$ to $R^{10}$, $R^{12}$ to $R^{19}$ and m has the same meaning as in formula [I]).

In formula [III], M, $X^1$, $X^2$, Q, $R^2$, $R^3$, $R^4$, $R^5$, $R^6$, $R^7$, $R^8$, $R^9$, $R^{12}$, $R^{13}$, $R^{14}$, $R^{15}$, $R^{16}$, $R^{17}$, $R^{18}$, $R^{19}$, $R^{10}$ and m are the same substituents as in formula [I].

Z is an oxygen atom or a sulfur atom, preferably an oxygen atom.

The substituents $R^{31}$ and $R^{33}$ are preferably a hydrogen atom, a halogen atom, an alkyl group having a carbon number of 1 to 6, or an aryl group having a carbon number of 6 to 18, more preferably a hydrogen atom or an alkyl group having a carbon number of 1 to 6. The substituents $R^{30}$ and $R^{32}$ are preferably a halogen atom, an alkyl group having a carbon number of 1 to 6, or an aryl group having a carbon number of 6 to 18, more preferably an alkyl group having a carbon number of 1 to 6 or an aryl group having a carbon number of 6 to 18, still more preferably a methyl group.

Specific Examples of Metallocene Compound:

Specific examples of the metallocene complex of the present invention are recited below.

Specific examples of 5-methylindenyl skeleton when Q and A form a 4-membered ring
(1) Dichlorosilacyclobutylenebis[2-(2-furyl)-4-phenyl-5-methyl-1-indenyl]zirconium
(2) Dichlorosilacyclobutylenebis[2-(5-methyl-2-furyl)-4-phenyl-5-methyl-1-indenyl]zirconium
(3) Dichlorosilacyclobutylenebis[$_2$-(4,5-dimethyl-2-furyl)-4-phenyl-5-methyl-1-indenyl]zirconium
(4) Dichlorosilacyclobutylenebis[2-(5-tert-butyl-2-furyl)-4-phenyl-5-methyl-1-indenyl]zirconium
(5) Dichlorosilacyclobutylenebis[2-(5-phenyl-2-furyl)-4-phenyl-5-methyl-1-indenyl]zirconium
(6) Dichlorosilacyclobutylenebis[2-(2-thienyl)-4-phenyl-5-methyl-1-indenyl]zirconium
(7) Dichlorosilacyclobutylenebis[2-(5-methyl-2-thienyl)-4-phenyl-5-methyl-1-indenyl]zirconium
(8) Dichlorosilacyclobutylenebis[2-(5-methyl-2-furyl)-4-(4-fluorophenyl)-5-methyl-1-indenyl]zirconium
(9) Dichlorosilacyclobutylenebis[2-(5-methyl-2-furyl)-4-(4-chlorophenyl)-5-methyl-1-indenyl]zirconium
(10) Dichlorosilacyclobutylenebis[2-(5-methyl-2-furyl)-4-(4-methylphenyl)-5-methyl-1-indenyl]zirconium
(11) Dichlorosilacyclobutylenebis[2-(5-methyl-2-furyl)-4-(4-tert-butylphenyl)-5-methyl-1-indenyl]zirconium
(12) Dichlorosilacyclobutylenebis[2-(5-methyl-2-furyl)-4-(3,5-dimethylphenyl)-5-methyl-1-indenyl]zirconium
(13) Dichlorosilacyclobutylenebis[2-(5-methyl-2-furyl)-4-(3,5-di-tert-butylphenyl)-5-methyl-1-indenyl]zirconium
(14) Dichlorosilacyclobutylenebis[2-(5-methyl-2-furyl)-4-(1-naphthyl)-5-methyl-1-indenyl]zirconium
(15) Dichlorosilacyclobutylenebis[2-(5-methyl-2-furyl)-4-(2-naphthyl)-5-methyl-1-indenyl]zirconium
(16) Dichlorosilacyclobutylenebis[2-(5-methyl-2-furyl)-4-(4-biphenylyl)-5-methyl-1-indenyl]zirconium Specific examples of 5,6-dimethylindenyl skeleton when Q and A form a 4-membered ring
(17) Dichlorosilacyclobutylenebis[2-(2-furyl)-4-phenyl-5,6-dimethyl-1-indenyl]zirconium
(18) Dichlorosilacyclobutylenebis[2-(5-methyl-2-furyl)-4-phenyl-5,6-dimethyl-1-indenyl]zirconium
(19) Dichlorosilacyclobutylenebis[2-(4,5-dimethyl-2-furyl)-4-phenyl-5,6-dimethyl-1-indenyl]zirconium
(20) Dichlorosilacyclobutylenebis[2-(5-tert-butyl-2-furyl)-4-phenyl-5,6-dimethyl-1-indenyl]zirconium
(21) Dichlorosilacyclobutylenebis[2-(5-phenyl-2-furyl)-4-phenyl-5,6-dimethyl-1-indenyl]zirconium
(22) Dichlorosilacyclobutylenebis[2-(2-thienyl)-4-phenyl-5,6-dimethyl-1-indenyl]zirconium
(23) Dichlorosilacyclobutylenebis[2-(5-methyl-2-thienyl)-4-phenyl-5,6-dimethyl-1-indenyl]zirconium
(24) Dichlorosilacyclobutylenebis[2-(5-methyl-2-furyl)-4-(4-fluorophenyl)-5,6-dimethyl-1-indenyl]zirconium
(25) Dichlorosilacyclobutylenebis[2-(5-methyl-2-furyl)-4-(4-chlorophenyl)-5,6-dimethyl-1-indenyl]zirconium
(26) Dichlorosilacyclobutylenebis[2-(5-methyl-2-furyl)-4-(4-methylphenyl)-5,6-dimethyl-1-indenyl]zirconium
(27) Dichlorosilacyclobutylenebis[2-(5-methyl-2-furyl)-4-(4-tert-butylphenyl)-5,6-dimethyl-1-indenyl]zirconium
(28) Dichlorosilacyclobutylenebis[2-(5-methyl-2-furyl)-4-(3,5-dimethylphenyl)-5,6-dimethyl-1-indenyl]zirconium
(29) Dichlorosilacyclobutylenebis[2-(5-methyl-2-furyl)-4-(3,5-di-tert-butylphenyl)-5,6-dimethyl-1-indenyl]zirconium
(30) Dichlorosilacyclobutylenebis[2-(5-methyl-2-furyl)-4-(1-naphthyl)-5,6-dimethyl-1-indenyl]zirconium
(31) Dichlorosilacyclobutylenebis[2-(5-methyl-2-furyl)-4-(2-naphthyl)-5,6-dimethyl-1-indenyl]zirconium
(32) Dichlorosilacyclobutylenebis[2-(5-methyl-2-furyl)-4-(4-biphenylyl)-5,6-dimethyl-1-indenyl]zirconium Specific examples of indacenyl skeleton when Q and A form a 4-membered ring
(33) Dichlorosilacyclobutylenebis[2-(2-furyl)-4-phenyl-1,5,6,7-tetrahydro-s-indacen-1-yl]zirconium
(34) Dichlorosilacyclobutylenebis[2-(5-methyl-2-furyl)-4-phenyl-1,5,6,7-tetrahydro-s-indacen-1-yl]zirconium
(35) Dichlorosilacyclobutylenebis[2-(4,5-dimethyl-2-furyl)-4-phenyl-1,5,6,7-tetrahydro-s-indacen-1-yl]zirconium
(36) Dichlorosilacyclobutylenebis[2-(5-tert-butyl-2-furyl)-4-phenyl-1,5,6,7-tetrahydro-s-indacen-1-yl]zirconium
(37) Dichlorosilacyclobutylenebis[2-(5-phenyl-2-furyl)-4-phenyl-1,5,6,7-tetrahydro-s-indacen-1-yl]zirconium
(38) Dichlorosilacyclobutylenebis[2-(2-thienyl)-4-phenyl-1,5,6,7-tetrahydro-s-indacen-1-yl]zirconium
(39) Dichlorosilacyclobutylenebis[2-(5-methyl-2-thienyl)-4-phenyl-1,5,6,7-tetrahydro-s-indacen-1-yl]zirconium
(40) Dichlorosilacyclobutylenebis[2-(5-methyl-2-furyl)-4-(4-fluorophenyl)-1,5,6,7-tetrahydro-s-indacen-1-yl]zirconium
(41) Dichlorosilacyclobutylenebis[2-(5-methyl-2-furyl)-4-(4-chlorophenyl)-1,5,6,7-tetrahydro-s-indacen-1-yl]zirconium
(42) Dichlorosilacyclobutylenebis[2-(5-methyl-2-furyl)-4-(4-methylphenyl)-1,5,6,7-tetrahydro-s-indacen-1-yl]zirconium
(43) Dichlorosilacyclobutylenebis[2-(5-methyl-2-furyl)-4-(4-tert-butylphenyl)-1,5,6,7-tetrahydro-s-indacen-1-yl]zirconium
(44) Dichlorosilacyclobutylenebis[2-(5-methyl-2-furyl)-4-(3,5-dimethylphenyl)-1,5,6,7-tetrahydro-s-indacen-1-yl]zirconium

(45) Dichlorosilacyclobutylenebis[2-(5-methyl-2-furyl)-4-(3,5-di-tert-butylphenyl)-1,5,6,7-tetrahydro-s-indacen-1-yl]zirconium
(46) Dichlorosilacyclobutylenebis[2-(5-methyl-2-furyl)-4-(1-naphthyl)-1,5,6,7-tetrahydro-s-indacen-1-yl]zirconium
(47) Dichlorosilacyclobutylenebis[2-(5-methyl-2-furyl)-4-(2-naphthyl)-1,5,6,7-tetrahydro-s-indacen-1-yl]zirconium
(48) Dichlorosilacyclobutylenebis[2-(5-methyl-2-furyl)-4-(4-biphenylyl)-1,5,6,7-tetrahydro-s-indacen-1-yl]zirconium
(49) Dichlorosilacyclobutylenebis[2-(2-furyl)-4-phenyl-1,5,6,7-tetrahydro-5,5,7,7-tetramethyl-s-indacen-1-yl]zirconium
(50) Dichlorosilacyclobutylenebis[2-(5-methyl-2-furyl)-4-phenyl-1,5,6,7-tetrahydro-5,5,7,7-tetramethyl-s-indacen-1-yl]zirconium Specific examples when Q and A form a 4-membered ring and $R^1$ and $R^{11}$ are different

(51) Dichlorosilacyclobutylene[2-(5-methyl-2-furyl)-4-phenyl-5-methyl-1-indenyl][2,5-dimethyl-4-phenyl-1-indenyl]zirconium
(52) Dichlorosilacyclobutylene[2-(5-methyl-2-furyl)-4-phenyl-5-methyl-1-indenyl][2-(2-furyl)-4-phenyl-5-methyl-1-indenyl]zirconium
(53) Dichlorosilacyclobutylene[2-(5-methyl-2-furyl)-4-phenyl-5-methyl-1-indenyl][2-(5-tert-butyl-2-furyl)-4-phenyl-5-methyl-1-indenyl]zirconium Specific examples when Q and A form a 4-membered ring and $R^7$ and $R^{17}$ and/or $R^8$ and $R^{18}$ are different

(54) Dichlorosilacyclobutylene[2-(5-methyl-2-furyl)-4-phenyl-5-methyl-1-indenyl][2-(5-methyl-2-furyl)-4-phenyl-1-indenyl]zirconium
(55) Dichlorosilacyclobutylene[2-(5-methyl-2-furyl)-4-phenyl-5-methyl-1-indenyl][2-(5-methyl-2-furyl)-4-phenyl-5,6-dimethyl-1-indenyl]zirconium
(56) Dichlorosilacyclobutylene[2-(5-methyl-2-furyl)-4-phenyl-5-methyl-1-indenyl][2-(5-methyl-2-furyl)-4-phenyl-1,5,6,7-tetrahydro-s-indacen-1-yl]zirconium Specific examples when Q and A form a 5-membered ring

(57) Dichlorosilacyclopentylenebis[2-(2-furyl)-4-phenyl-5-methyl-1-indenyl]zirconium
(58) Dichlorosilacyclopentylenebis[2-(5-methyl-2-furyl)-4-phenyl-5-methyl-1-indenyl]zirconium
(59) Dichlorosilacyclopentylenebis[2-(2-furyl)-4-phenyl-1,5,6,7-tetrahydro-s-indacen-1-yl]zirconium
(60) Dichlorosilacyclopentylenebis[2-(5-methyl-2-furyl)-4-phenyl-1,5,6,7-tetrahydro-s-indacen-1-yl]zirconium Other examples include compounds where the central metal M in the compounds exemplified above is a hafnium atom in place of a zirconium atom, and compounds where one or both of $X^1$ and $X^2$ are a bromine atom, an iodine atom, a methyl group, a phenyl group, a dimethylamino group, a diethylamino group, etc. in place of a chlorine atom exemplified.

Synthesis Method of Metallocene Compound

The metallocene complex (compound) of the present invention can be synthesized by an arbitrary method according to the form of substituent or bond. One example of the typical synthetic route is illustrated below.

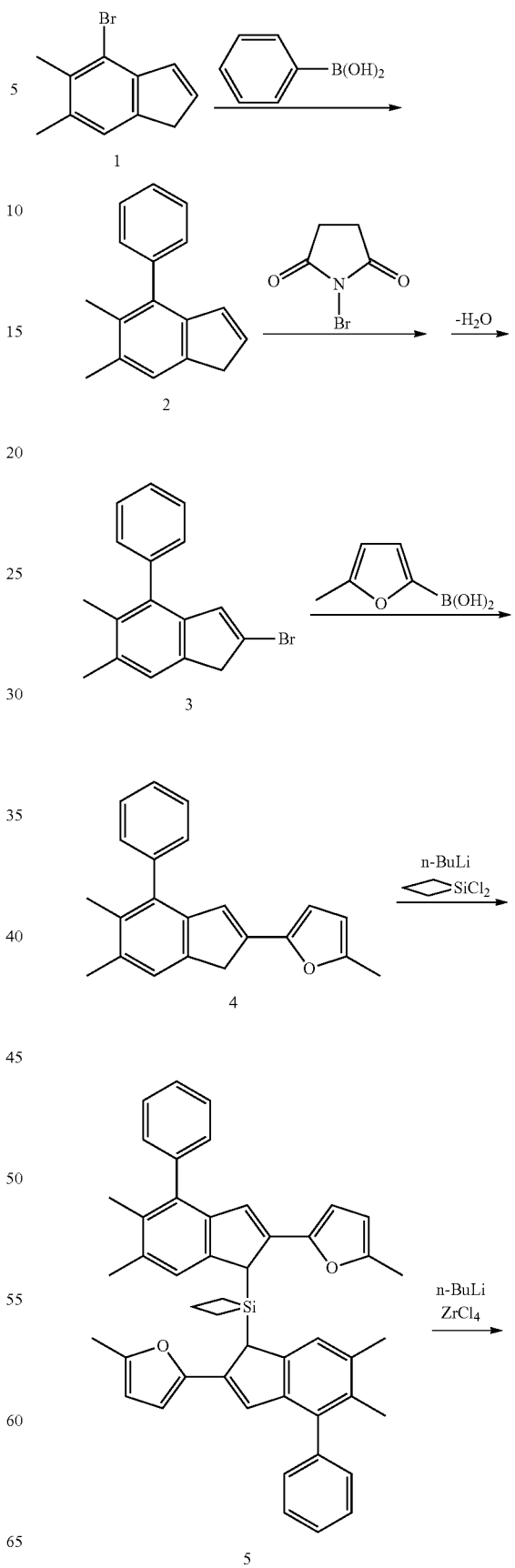

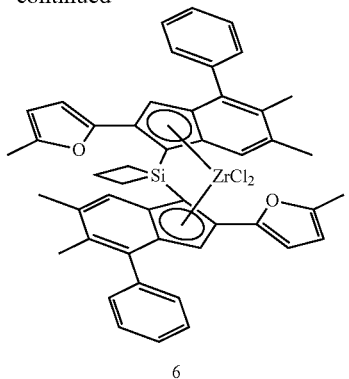

6

In the synthetic route above, a coupling reaction of Compound 1 with a phenylboronic acid is performed in the presence of a palladium catalyst to obtain Compound 2. Compound 2 can be brominated into Compound 3, for example, by a method described in the literature (J. Org. Chem. 1982, 47, 705-709), and bromination is obtained by reacting N-bromosuccinimide with Compound 2 in the presence of water and dehydrating the reaction product with an acid such as p-toluenesulfonic acid. A coupling reaction of Compound 3 with 5-methyl-2-furylboronic acid is performed in the presence of a palladium catalyst to obtain Compound 4. As for crosslinked Compound 5, Compound 4 is anionized with butyllithium, etc. and then reacted with 1,1-dichlorosilacyclobutane to obtain Compound 5. Compound 5 is dianionized with 2 equivalents of n-butyllithium, etc. and then reacted with zirconium tetrachloride to obtain Metallocene Compound 6.

A metallocene compound having introduced thereinto substituents can be synthesized by using corresponding substituent raw materials. When a corresponding boronic acid, for example, 4,5-dimethyl-2-furylboronic acid or 2-thienylboronic acid, is used in place of 5-methyl-2-furylboronic acid, a corresponding 2-position substituent ($R^1$, $R^{11}$) can be introduced, and in the case of introducing an alkyl group as the 2-position substituent ($R^1$, $R^{11}$), this can be introduced by reacting a Grignard reagent with Compound 3 in the presence of an Ni catalyst as described in the literature (J. Org. Chem. 1984, 49, 4226).

In the synthesis of a metallocene compound having different substituents on two indenyl rings, different substituted indenes are sequentially reacted with 1,1-dichlorosilacyclobutane, etc., whereby the rings can be crosslinked. At the time of crosslinking, a crosslinking aid such as nitrogen-containing compound (e.g., methylimidazole) may be allowed to be present.

2. Catalyst for Olefin Polymerization

The metallocene complex of the present invention forms a catalyst component for olefin polymerization, and the catalyst component can be used in a catalyst for olefin polymerization. The component is preferably used, for example, in the below-described catalyst for olefin polymerization containing the metallocene complex as a component (A).

(1) Component of Catalyst for Olefin Polymerization

The catalyst for olefin polymerization of the present invention contains the following components (A), (B) and (C):

component (A): a metallocene complex represented by formula [I] or [III];

component (B): a compound reacting with the component (A) to form an ion pair, or an ion-exchange layered silicate; and component (C): an organoaluminum compound.

(2) Respective Components

As for the metallocene complex represented by formula [I] or [III] of the component (A), two or more compounds represented by formula [I] or [III], which are the same or different, may be used.

The component (B), i.e., a compound reacting with the component (A) to form an ion pair, or an ion-exchange layered silicate, includes an aluminum oxy compound, a boron compound, an ion-exchange layered silicate, etc. and is preferably an ion-exchange layered silicate. As the component (B), one of these compounds may be used alone, or two or more thereof may be mixed and used.

As to the aluminum oxy compound, it is well known that an aluminum oxy compound can activate a metallocene complex, and such a compound includes, specifically, a compound represented by each of the following formulae [IV] to [VI]:

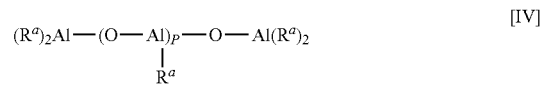 [IV]

 [V]

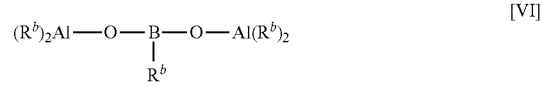 [VI]

In formulae [IV] and [V], $R^a$ represents a hydrogen atom or a hydrocarbon group, preferably a hydrocarbon group having a carbon number of 1 to 10, more preferably a carbon number of 1 to 6. The plurality of $R^a$ may be the same or different, and p represents an integer of 0 to 40, preferably from 2 to 30.

The compounds represented by formulae [IV] and [V] are compounds also referred to as aluminoxane, and among these, methyl aluminoxane and methylisobutyl aluminoxane are preferred. A plurality of aluminoxanes may be used in combination in each group or among groups. The aluminoxane can be prepared under various known conditions.

The compound represented by formula [VI] can be obtained by reacting one kind of trialkylaluminum or two or more kinds of trialkylaluminum with an alkylboronic acid represented by the formula: $R^bB(OH)_2$, in a ratio of 10:1 to 1:1 (by mol). In the formula, $R^b$ represents a hydrocarbon group having a carbon number of 1 to 10, preferably a hydrocarbon group having a carbon number of 1 to 6.

The boron compound includes, for example, a complex of a cation such as carbonium and ammonium cations with an organoboron compound such as triphenylboron, tris(3,5-difluorophenyl)boron and tris(pentafluorophenyl)boron, and various organoboron compounds such as tris(pentafluorophenyl)boron.

The ion-exchange layered silicate (hereinafter, sometimes simply referred to as "silicate") indicates a silicate compound having a crystal structure in which planes each constituted by an ionic bond, etc. are stacked one another in parallel by a bonding force, and contained ions are exchangeable. Various silicates are known and specifically described in Haruo Shiramizu, "Nendo Kobutsu Gaku (Clay Mineralogy)", Asakura Shoten (1995).

In the present invention, the silicate preferably used as the component (B) is one belonging to a smectite group and specifically includes montmorillonite, sauconite, beidellite, nontronite, saponite, hectorite, stevensite, etc. Among these, in view of activity and molecular weight of the rubber component, montmorillonite is preferred.

Most natural silicates are produced as a main component of clay mineral, and impurities (e.g., quartz, cristobalite) other than the ion-exchange layered silicate are contained in many cases. Impurities may be contained in the smectite group silicate for use in the present invention.

Granulation of Ion-Exchange Layered Silicate:

The silicate may be used in a dry state or in a state of being slurried in a liquid. The shape of the ion-exchange layered silicate is not particularly limited and may be a naturally occurring shape or a shape at the time of artificial synthesis, or an ion-exchange layered silicate with the shape being processed by an operation such as pulverization, granulation, classification, etc. may also be used. Among these, granulated silicate provides good polymer particle property and is preferably used.

The shape processing of the ion-exchange layered silicate, such as granulation, pulverization and classification, may be performed before an acid treatment, or the shape may be processed after an acid treatment.

The granulation method used here includes, for example, a stirring granulation method, a spray granulation method, a rolling granulation method, briquetting, compacting, an extrusion granulation method, a fluidized-bed granulation method, an emulsifying granulation method, a submerged granulation method, and a compression molding granulation method but is not particularly limited. A stirring granulation method, a spray granulation method, a rolling granulation method and a fluidized-bed granulation method are preferred, and a stirring granulation method and a spray granulation method are more preferred.

In the case of performing spray granulation, water or an organic solvent such as methanol, ethanol, chloroform, methylene chloride, pentane, hexane, heptane, toluene and xylene, is used as the dispersion medium of a raw material slurry. Preferably, water is used as the dispersion medium. The concentration of the component (B) in a raw material slurry liquid for spray granulation providing a spherical particle is from 0.1 to 30 wt %, preferably from 0.5 to 20 wt %, more preferably from 1 to 10 wt %. The inlet temperature of hot air for spray granulation providing a spherical particle varies depending on the dispersion medium but in the case of water, is from 80 to 260° C., preferably from 100 to 220° C.

At the time of granulation, in order to obtain a carrier having high particle strength and enhance the propylene polymerization activity, the silicate is micronized, if desired. The silicate may be micronized by any method. The micronization method can be either method of dry milling or wet milling. Wet milling using water as the dispersion medium and making use of swellability of silicate is preferred, and this method includes, for example, a method by forced stirring using Polytron, etc., and a method by means of Dynomill, a pearl mill, etc. The average particle diameter before granulation is from 0.01 to 3 μm, preferably 0.05 to 1 μm.

At the time of granulation, an organic material, an inorganic solvent, an inorganic salt, or various binders may also be used. The binder used includes, for example, magnesium chloride, aluminum sulfate, aluminum chloride, magnesium sulfate, alcohols, and glycols.

The spherical particle obtained as above preferably has a compressive fracture strength of 0.2 MPa or more for suppressing crushing or dust generation in the polymerization process. The particle diameter of the granulated ion-exchange layered silicate is from 0.1 to 1,000 μm, preferably from 1 to 500 μm. The pulverization method is also not particularly limited and may be either dry pulverization or wet pulverization.

Acid Treatment:

The silicate for use in the present invention is subjected to an acid treatment before use. The treatment may be performed in combination with other chemical treatments. Other chemical treatments include an alkali treatment, a treatment with salts, and a treatment with an organic material.

The acid treatment of the silicate can change the acid strength of a solid. In addition, the acid treatment has an effect of exchanging ions and removing impurities on the surface and an effect of partially eluting cations such as Al, Fe, Mg and Li in the crystal structure.

The acid used in the acid treatment includes hydrochloric acid, nitric acid, sulfuric acid, phosphoric acid, acetic acid, oxalic acid, benzoic acid, stearic acid, propionic acid, acrylic acid, maleic acid, fumaric acid, phthalic acid, etc. Two or more of these may be used at the same time. Among others, an inorganic acid is preferred, sulfuric acid, hydrochloric acid and nitric acid are more preferred, and sulfuric acid is still more preferred.

A method combining an acid treatment and a treatment with salts is particularly preferred, and examples thereof include a method of performing an acid treatment after performing a treatment with salts, a method of performing a treatment with salts after performing an acid treatment, a method of simultaneously performing a treatment with salts and an acid treatment, and a method of simultaneously performing a treatment with salts and an acid treatment after performing a treatment with salts.

As for the conditions of the treatment with an acid, conditions that the acid concentration is from 0.1 to 30 wt %, the treatment temperature is from room temperature to boiling point of the used solvent, and the treatment time is from 5 minutes to 24 hours are usually selected, and the treatment is preferably performed under the conditions allowing at least part of the to-be-treated compound to dissolve out. The acid is generally used in the form of an aqueous solution. For example, in the case of using sulfuric acid, it is preferred that the treatment temperature is from 80 to 100° C. and the treatment time is from 0.5 hours to less than 5 hours.

When a treatment with salts is performed at the same time, an ion composite, a molecule composite, an organic derivative, etc. are formed, and the surface area or the distance between layers can be thereby changed. For example, by utilizing ion exchangeability, an exchangeable ion between layers can be replaced by another large bulky ion, thereby producing a layered material having an enlarged distance between layers.

In the case of performing the above-described acid treatment, the shape may be controlled by pulverization, granulation, etc., before, during or after the treatment. In addition, other chemical treatments such as alkali treatment, organic compound treatment and organometallic treatment may be used in combination.

The salts used for ion exchange are a compound containing at least one atom selected from the group consisting of Groups 1 to 14 atoms of the long-form Periodic Table, preferably a compound composed of a cation containing at least one atom selected from the group consisting of Groups 1 to 14 atoms of the Periodic Table and an anion derived from at least one atom or atomic group selected from a halogen atom, an inorganic acid and an organic acid, more preferably a compound composed of a cation containing at least one atom selected from the group consisting of Groups 2 to 14 atoms of the Periodic Table and at least one anion selected from the group consisting of Cl, Br, I, F, $PO_4$, $SO_4$, $NO_3$, $CO_3$, $C_2O_4$, $ClO_3$, $ClO_4$, $OOCCH_3$, $CH_3COCHCOCH_3$, $OCl_2$, $O(NO_3)_2$, $O(ClO_4)_2$, $O(SO_4)$, OH, $O_2Cl_2$, $OCl_3$, OOCH, $OOCCH_2CH_3$, $C_2H_4O_4$, and $C_6H_5O_7$. Two or more of these salts may be used at the same time.

In the thus-obtained silicate, the volume of pores having a radius of 20 Å or more as measured by a mercury penetration method is preferably 0.1 $cm^3/g$ or more, particularly from 0.3 to 5 $cm^3/g$. Such silicate contains adsorbed water and intercalated water when treated in an aqueous solution. The adsorbed water as used herein is water adsorbed onto the surface of silicate or the fracture surface of crystal, and the intercalated water is water present between layers of crystal.

The silicate is preferably used after removing the above-described adsorbed water and intercalated water. The dehydration method is not particularly limited, but a method, such as heating dehydration, heating dehydration under gas flow, heating dehydration under reduced pressure and azeotropic dehydration with an organic solvent, is used. The heating temperature is set to a temperature range of preventing adsorbed water and intercalated water from remaining and is usually 100° C. or more, preferably 150° C. or more, but a high temperature condition causing a structural destruction is not preferred. The heating time is 0.5 hours or more, preferably 1 hour or more. At this time, the weight reduction of silicate after dehydration and drying is preferably 3 wt % or less as a value when suctioned for 2 hours under the conditions of a temperature of 200° C. and a pressure of 1 mmHg. In the present invention, in the case of using silicate where the weight reduction is adjusted to 3 wt % or less, the silicate is preferably dealt with so as for the same weight reduction to be kept also at the time of contact with the component (A) and the component (C).

Composition of Silicate after Acid Treatment:

The acid-treated silicate that is the component (B) according to the present invention preferably has an atom ratio of Al/Si of 0.01 to 0.29, preferably from 0.03 to 0.25, more preferably from 0.05 to 0.23, in view of the activity of the polymerization catalyst and the molecular weight of the rubber component.

The Al/Si atom ratio is an indicator indicating the strength of acid treatment in the clay moiety and as the method for controlling the Al/Si atom ratio, the ratio can be controlled by adjusting, when performing an acid treatment, the acid species, acid concentration, acid treatment time and temperature.

Aluminum and silicon in the silicate are measured by a method of preparing a calibration curve based on chemical analysis according to JIS and quantitatively determining the elements with fluorescent X-ray.

Component (C):

One example of the organoaluminum compound is represented by the following formula:

In the formula, R represents a hydrocarbon group having a carbon number of 1 to 20, X represents a hydrogen atom, a halogen atom, an alkoxy group or a siloxy group, and a represents a number of more than 0 and 3 or less.

Specific examples of the organoaluminum compound represented by the formula include a trialkylaluminum such as trimethylaluminum, triethylaluminum, tripropylaluminum and triisobutylaluminum, and a halogen- or alkoxy-containing alkylaluminum such as diethylaluminum monochloride and diethylaluminum monomethoxide. Among these, a trialkylaluminum is preferred. Two or more of these organoaluminum compounds may be used in combination.

(3) Preparation Method of Catalyst

In the preparation method of the catalyst for olefin polymerization according to the present invention, the method for contacting the component (A), the component (B) and the component (C) is not particularly limited but includes, for example, the following methods:

(i) a method of contacting the component (A) and the component (B) and then adding the component (C);

(ii) a method of contacting the component (A) and the component (C) and then adding the component (B);

(iii) a method of contacting the component (B) and the component (C) and then adding the component (A);

(iv) a method of contacting respective components (A), (B) and (C) at the same time.

Furthermore, respective components may be used as a mixture of different kinds of components or may be separately contacted by changing the order. This contact may be performed not only at the time of preparation of a catalyst but also at the time of prepolymerization by olefin or polymerization of olefin.

In addition, respective components may be contacted by dividing a component into parts, in such a manner that the component (B) and the component (C) are contacted and a mixture of the component (A) and the component (C) is then added.

The contact of respective components (A), (B) and (C) is preferably performed in an inert gas such as nitrogen and in an inert hydrocarbon solvent such as pentane, hexane, heptane, toluene or xylene. The contact can be performed at a temperature between −20° C. and the boiling point of the solvent and in particular, is preferably performed at a temperature between room temperature and the boiling point of the solvent.

In the polymerization catalyst according to the present invention, when the component (B) is silicate, as for the preferable amounts of component (A), component (B) and component (C), the amount used of a metallocene compound of the component (A) is from 0.001 to 10 mmol, more preferably from 0.001 to 1 mmol, per gram of the component (B). As for the amount of the component (C) used, the molar ratio of Al/metallocene compound is from 0.1 to 100,000, preferably from 1 to 10,000. These usage proportions are an example of the normal ratio, and the present invention is not limited to the above-described usage proportion, as long as the catalyst conforms to the object of the present invention.

Before using the catalyst containing the components (A), (B) and (C) as a catalyst for olefin polymerization (main polymerization), a prepolymerization of preliminarily polymerizing a small amount of an olefin such as ethylene, propylene, 1-butene, 1-hexene, 1-octene, 4-methyl-1-pentene, 3-methyl-1-butene, vinylcycloalkane and styrene may be applied, if desired. As the method for prepolymerization, a known method may be used.

(4) Olefin

The catalyst for olefin polymerization of the present invention can be used for homopolymerization of one polymerization monomer selected from the group consisting of ethylene and α-olefins, or for copolymerization of two or more polymerization monomers.

The α-olefin indicates, for example, an olefin having a carbon number of 3 to 20 and specifically includes propylene, 1-butene, 1-pentene, 1-hexene, 1-heptene, 1-octene, 1-decene, 1-dodecene, 1-hexadecene, 4-methyl-1-pentene, styrene, vinylcyclohexane, diene, triene, cyclic olefin, etc.

3. Polymerization Method

In the present invention, as for the polymerization form, all modes can be employed as long as a polymerization catalyst containing the metallocene complex represented by formula [I] or [II] can be efficiently put into contact with monomers to catalyze olefin polymerization or copolymerization.

Specifically, for example, a slurry method using an inert solvent, a bulk polymerization method using substantially no inert solvent but using propylene as a solvent, and a gas-phase polymerization method of keeping each monomer in a gaseous state by using substantially no liquid solvent.

As for the polymerization method, a method of performing continuous polymerization, batch polymerization, or prepolymerization may also be applied.

The combination of polymerization types is not particularly limited, and a mode such as two-stage bulk polymerization, bulk polymerization followed by gas-phase polymerization, or two-stage gas-phase polymerization can be employed as well. The polymer can also be produced through a larger number of polymerization stages.

Above all, in order to obtain a polymer having a good particle shape, it is preferable to perform the first step by bulk polymerization and the second step by gas-phase polymerization or to perform both the first and second steps by gas-phase polymerization.

Use of the catalyst of the present invention makes it possible to produce a homopolypropylene with high activity, particularly an ethylene/propylene copolymer with high activity, provide a good uptake efficiency of ethylene and α-olefin as comonomers, and produce a propylene-based polymer having rigidity and impact resistance. The production method is preferably a polymerization method including the following step 1 (first step) and step 2 (second step), more preferably a polymerization method of performing step 2 continuously after step 1. Multistage polymerization of producing the polymer through three or more stages in combination with other polymerization conditions may also be performed.

[Step 1]

Step 1 is a step of polymerizing from 90 to 100 wt % of propylene and from 0 to 10 wt % of ethylene or α-olefin relative to all monomer components.

In the case of slurry polymerization, as the polymerization solvent, saturated aliphatic or aromatic hydrocarbons such as hexane, heptane, pentane, cyclohexane, benzene and toluene are used individually or as a mixture.

The polymerization temperature is from 0 to 150° C., and hydrogen can be secondarily used as a molecular weight modifier. The polymerization pressure is suitably from 0 to 3 MPaG, preferably from 0 to 2 MPaG.

In the case of a bulk polymerization method, the polymerization temperature is from 0 to 90° C., preferably from 60 to 80° C. The polymerization pressure is suitably from 0 to 5 MPaG, preferably from 0 to 4 MPaG.

In the case of gas-phase polymerization, the polymerization temperature is from 0 to 200° C., preferably from 50 to 120° C., more preferably from 60 to 100° C. The polymerization pressure is suitably from 0 to 4 MPaG, preferably from 0 to 3 MPaG.

Step 1 is preferably performed by a bulk polymerization method or gas-phase polymerization.

Ethylene or α-olefin may be allowed to coexist in a range of 0 to 10%, not deteriorating the shape of the polymer, relative to all monomer components, and in this case, the molecular weight, activity and melting point can be adjusted. Hydrogen may be used as a molecular weight modifier.

[Step 2]:

Step 2 is a step of polymerizing from 10 to 90 wt % of propylene and from 10 to 90 wt % of ethylene or α-olefin, relative to all monomer components, where a rubber component exhibiting suitable impact resistance can be produced. In terms of providing a propylene polymer having high impact resistance, the amount of propylene is preferably from 20 to 80 wt % relative to monomer components.

In the case of slurry polymerization and bulk polymerization, the polymerization conditions of step 2 are the same as in step 1, but in the case of gas-phase polymerization, since the monomer composition differs from that in step 1, the polymerization temperature is from 0 to 200° C., preferably from 20 to 90° C., more preferably from 30 to 80° C. The polymerization pressure is suitably from 0 to 4 MPaG, preferably from 1 to 3 MPaG. Hydrogen may be used as a molecular weight modifier.

Step 2 is preferably performed by gas-phase polymerization.

In the case of using ethylene as a monomer in step 2, the propylene-based polymer obtained by the polymerization method of the present invention has an ethylene-containing moiety that is observed in a 100° C. soluble fraction in CFC-IR. This ethylene-containing moiety is expected to improve the impact resistance and transparency.

[Polymerization Monomer]

In the present invention, the "α-olefin" indicates an olefin having a carbon number of 3 to 20 as described above and specifically includes propylene, 1-butene, 1-pentene, 1-hexene, 1-heptene, 1-octene, 1-decene, 1-dodecene, 1-hexadecene, 4-methyl-1-pentene, styrene, vinylcyclohexane, diene, triene, and cyclic olefin.

The monomer used together with propylene is preferably ethylene or 1-butene, more preferably ethylene. These monomers may be used in combination.

[Analysis of Characteristic Values of Polymerized Olefin Polymer]

The content of the copolymer component (rubber component; hereinafter referred to as "CP") obtained in the second step in the propylene-based polymer produced using the catalyst of the present invention and the proportion of ethylene or α-olefin in CP are determined by the following methods.

In the following example, ethylene in CP is used, but α-olefin other than ethylene is also determined by a method in accordance with the following example.

(1) Analyzers Used (i) Cross-Fractionation Apparatus

CFC T-100 manufactured by Dia Instruments Co., Ltd.

(ii) Fourier Transform Infrared Absorption Spectral Analysis (FT-IR)

1760× manufactured by PerkinElmer Inc.

A fixed-wavelength infrared spectrophotometer attached as a detector of CFC (cross-fractionation chromatograph) is detached and by connecting FT-IR instead, this FT-IR is used as the detector.

The transfer line between the outlet for a solution eluted from CFC and FT-IR is set to a length of 1 m and maintained at a temperature of 140° C. throughout the measurement. The flow cell attached to FT-IR has an optical path length of 1 mm and an optical path width of 5 mmφ and is maintained at a temperature of 140° C. throughout the measurement.

(iii) Gel Permeation Chromatography (GPC)

In the latter part of CFC, three GPC columns (AD806MS manufactured by Showa Denko K.K.) are connected in series and used.

(2) Measurement Conditions of CFC
  (i) Solvent: ortho-dichlorobenzene (ODCB)
  (ii) Sample concentration: 4 mg/mL
  (iii) Injection volume: 0.4 mL
  (iv) Crystallization: Temperature is lowered to 40° C. from 140° C. over about 40 minutes.
  (v) Fractionation method:

The fractionation temperature at the time of temperature rising elution fractionation is set to 40, 100 or 140° C., and the eluate is fractioned into a total of 3 fractions.

The elution ratios (unit:wt %) of a component (fraction 1) eluted at 40° C. or less, a component (fraction 2) eluted at 40 to 100° C., and a component (fraction 3) eluted at 100 to 140° C. are defined as W40, W100 and W140, respectively. W40+W100+W140=100. Each of the fractions is automatically transferred as it is to FT-IR analyzer.

(vi) Flow velocity of solvent at the time of elution: 1 mL/min.

(3) Measurement Conditions of FT-IR

After the sample solution starts eluting from GPC in the latter part of CFC, measurement of FT-IR is performed under the following conditions, and GPC-IR data on each of fractions 1 to 3 above are collected.
  (i) Detector: MCT
  (ii) Resolution: 8 $cm^{-1}$
  (iii) Measurement interval: 0.2 minutes (12 seconds)
  (iv) Cumulated number per one measurement: 15

(4) Post-Processing and Analysis of Measurement Results

The elution amount and molecular weight distribution of the component eluted at each temperature are determined by using the absorbance at 2,945 $cm^{-1}$ obtained by FT-IR as a chromatogram. The elution amount is normalized such that the total of the elution amounts of respective eluted components is 100%. The conversion from the retention volume to the molecular weight is performed using a calibration curve prepared in advance with standard polystyrene. The standard polystyrenes used are all produced by Tosoh Corporation under the following brand names:

(F380, F288, F128, F80, F40, F20, F10, F4, F1, A5000, A2500, A1000).

A calibration curve is created by injecting 0.4 mL of a solution prepared by dissolving each standard polystyrene in ODCB to provide a concentration of 0.5 mg/mL (containing 0.5 mg/mL of BHT). As the calibration curve, a cubic expression obtained by approximation according to the least square method is used. For the conversion to the molecular weight, a general-purpose calibration curve is used by reference to Sadao Mori, "Size Haijo Chromatography (Size Exclusion Chromatography)", Kyoritsu Shuppan. In the viscosity formula ($[\eta]=K \times M^\alpha$) used here, the following numerical values are used.

(i) At the time of creation of calibration curve using standard polystyrene:
  K=0.000138, α=0.70
(ii) At the time of measurement of sample of propylene-based block copolymer:
  K=0.000103, α=0.78

The ethylene content distribution of each eluted component (the distribution of ethylene contents along the molecular weight axis) is determined in terms of an ethylene polymerization ratio (mol %) by using the ratio between absorbance at 2,956 $cm^{-1}$ and absorbance at 2,927 $cm^{-1}$ obtained by GPC-IR, based on a calibration curve prepared in advance by use of polyethylene, polypropylene, ethylene-propylene rubber (EPR) of which ethylene content is known by $^{13}$C-NMR measurement, etc. and a mixture thereof.

(5) CP Content

The CP content of the propylene-based block copolymer in the present invention is defined by the following formula (i) and is determined through the following procedure:

$$CP\ content\ (wt\ \%) = W40 \times A40/B40 + W100 \times A100/B100 \quad (i)$$

In formula (i), W40 and W100 are an elution ratio (unit:wt %) of each fraction described above, A40 and A100 are an average ethylene content (unit:wt %) measured in each of fractions corresponding to W40 and W100, and B40 and B100 are an ethylene content (unit:wt %) of CP contained in each fraction. The method for determining A40, A100, B40 and B100 is described later.

The meanings in formula (i) are as follows.

The first term on the right side of formula (i) is a term for calculating the amount of CP contained in fraction 1 (portion soluble at 40° C.). In the case where fraction 1 contains only CP and does not contain a propylene polymer component (PP), W40 directly contributes to the fraction 1-derived CP content in the entirety, but fraction 1 also contains a small amount of PP-derived component (a component having an extremely low molecular weight and an atactic polypropylene) in addition to the CP-derived component, and this portion needs to be corrected. Accordingly, W40 is multiplied by A40/B40 to calculate the amount of CP-derived component in fraction 1. For example, when the average ethylene content (A40) of fraction 1 is 30 wt % and the ethylene content (B40) of CP contained in fraction 1 is 40 wt %, 30/40=3/4 (i.e., 75 wt %) of fraction 1 is derived from CP, and ¼ is derived from PP. In this way, the operation of multiplication by A40/B40 in the first term on the right side means to calculate the contribution of CP from wt % (W40) of fraction 1. The same applies to the second term on the right side, and the sum of contributions of CP calculated for respective fractions is the CP content.

Each of the average ethylene contents A40, A100 and A140 of fractions 1 to 3 is obtained as a sum of the products of the weight proportion for each data point in the absorbance chromatograph of 2,945 $cm^{-1}$ and the ethylene content for each data point (obtained from the ratio of absorbance at 2,956 $cm^{-1}$ to absorbance at 2,927 $cm^{-1}$).

The ethylene content (unit:wt %) corresponding to a peak position in the differential molecular weight distribution curve of fraction 1 is designated as B40.

As for fraction 2, the rubber moiety is considered to entirely elute at 40° C., and the ethylene content cannot be specified by the same definition and therefore, is defined as B100=100 in the present invention. Although B40 and B100 are ethylene contents of CP contained in respective fractions, it is substantially impossible to analytically determine these values. The reason therefor is that there is no means for completely separating and fractionating PP and CP mixed in the fraction.

As a result of studies using various model samples, it has been found that when an ethylene content corresponding to a peak position in the differential molecular weight distribution curve of fraction 1 is used for B40, the effect of improving physical properties of a material can be reasonably explained. In addition, for two reasons that the fraction has crystallinity derived from an ethylene chain and that the amount of CP contained in the fraction is relatively small compared with the amount of CP contained in fraction 1, when B100 is approximated to 100, this is close to the reality and substantially no error is caused by the calculation. Accordingly, analysis is performed by defining the content as B100=100.

Consequently, the CP content can be determined according to the following formula (ii):

$$CP \text{ content (wt \%)}=W40 \times A40/B40+W100 \times A100/100 \quad \text{(ii)}$$

That is, $W40 \times A40/B40$ in the first item on the right side of formula (ii) indicates the CP content (wt %) having no crystallinity, and $W100 \times A100/100$ in the second item indicates the CP content (wt %) having crystallinity.

The ethylene content in a copolymer component can be determined using the copolymer component content obtained by formula (ii) according to the following formula (iii):

$$\text{Ethylene content in copolymer component (wt \%)}= \\ (W40 \times A40+W100 \times A100+W140 \times A140)/[\text{copolymer component content (wt \%)}] \quad \text{(iii)}$$

The meaning of setting the above-described three kinds of fractionation temperatures is as follows.

In the CFC analysis according to the present invention, 40° C. has a meaning of a temperature condition necessary and sufficient for fractionating only a polymer not having crystallinity (for example, the majority of CP or among propylene polymer components (PP), a component having an extremely low molecular weight and an atactic component); 100° C. is a temperature necessary and sufficient for eluting only a component that is insoluble at 40° C. but becomes soluble at 100° C. (for example, a component, among CP, having crystallinity ascribable to the ethylene and/or propylene chain, and PP having low crystallinity); and 140° C. is a temperature necessary and sufficient for eluting only a component that is insoluble at 100° C. but becomes soluble at 140° C. (for example, a component, among PP, having particularly high crystallinity, and a component, among CP, having an extremely high molecular weight and extremely high ethylene crystallinity), and recovering the entire amount of the propylene-based block copolymer for use in the analysis.

Incidentally, in W140, a CP component is not contained at all or, if any, is contained in an extremely small and substantially negligible, and therefore, W140 is excluded from the calculation of the CP content or ethylene content.
(6) Ethylene Polymerization Ratio The ethylene content in CP is determined according to the following formula:

$$\text{Ethylene content (wt \%) in } CP=(W40 \times A40+W100 \times A100)/[CP]$$

wherein [CP] is the CP content (wt %) determined above.

The value of ethylene content (wt %) in CP obtained is finally converted to mol % by using the molecular weights of ethylene and propylene.

EXAMPLES

In order to more specifically and clearly describe the present invention, the present invention is described below by referring to Examples and Comparative Examples, and the reasonability and significance of constitutional requirements of the present invention as well as the superiority to conventional techniques are verified.

In the following examples, all of the complex synthesis step, the catalyst synthesis step and the polymerization step were performed in a purified nitrogen atmosphere, and the solvent was dehydrated and deaerated by bubbling with purified nitrogen before use.

In Examples, the measurement of physical properties, the analysis, etc. were performed according to the above-described methods and the methods described below.
(1) Measurement of MFR:

6 g of an acetone solution of a thermal stabilizer (BHT) (0.6 wt %) was added to 6 g of a polymer.

The polymer above was dried, then charged into a melt indexer (230° C.), and left standing for 5 minutes under a load of 2.16 Kg. Thereafter, the amount of the polymer extruded was measured, converted to an amount per 10 minutes, and used as the value of MFR (unit: dg/min).
(2) Measurement of Melting Point (Tm):

By using DSC (Model TA-2000 manufactured by DuPont, or Model DSC-6200 manufactured by Seiko Instruments Inc.), the melting point was determined from the measured value in second temperature rise at 10° C./min after temperature rise/drop was performed once at 10° C./min in a range of 20 to 200° C.
(3) Measurement of CFC:

The measurement was performed by the method described in detail above in the description.

Example 1

Metallocene Complex A

Synthesis of dichlorosilacyclobutylenebis[2-(5-methyl-2-furyl)-4-phenyl-1,5,6,7-tetrahydro-s-indacen-1-yl]zirconium (1-1) Synthesis of
4-bromo-1,2,3,5-tetrahydro-s-indacene 4-Bromo-3,5,6,7-tetrahydro-2H-s-indacen-1-one (45 g) was added to a suspended solution of aluminum chloride (81 g) and chloroform (300 mL). After stirring at room temperature for 1 hour, a chloroform solution (40 mL) of bromine (13 mL) was added dropwise under cooling on an ice bath and reacted day and night at room temperature. After the completion of reaction, the reaction solution was poured in 1 N hydrochloric acid-ice water, followed by stirring. The organic layer was liquid-separated, washed with 1 N hydrochloride acid, water and saturated brine, and then dried over magnesium sulfate. The solvent was removed by distillation under reduced pressure, and the residue was extracted with diethyl ether to obtain a yellow solid (26 g). The obtained solid was dissolved in ethanol, and sodium borohydride (4 g) was added under cooling on an ice bath, followed by stirring day and night at room temperature. After the reaction, about half of the solvent was removed by distillation under reduced pressure, and the residue was quenched by the addition of 1 N hydrochloric acid and then extracted with ether. The organic layer was washed successively with water and saturated brine and dried over magnesium sulfate, and the solvent was removed by distillation under reduced pressure. Furthermore, a suspension solution of the obtained yellow solid (27 g), p-toluenesulfonic acid (0.5 g) and toluene (150 mL) was heated under reflux. After one hour, the organic layer was separated by adding water, washed with saturated brine and then dried over magnesium sulfate, and the solvent was removed by distillation to obtain 24.3 g of a crude product of 4-bromo-1,2,3,5-tetrahydro-s-indacene.

$^1$H-NMR (400 MHz, CDCl$_3$) δ 2.0-2.2 (m, 2H), 2.9-3.1 (m, 4H), 3.33 (s, 2H), 6.52 (d, 1H), 6.85 (d, 1H), 7.51 (s, 1H).

(1-2) Synthesis of 4-phenyl-1,2,3,5-tetrahydro-s-indacene

In a 500 mL three-neck flask, 4-bromo-1,2,3,5-tetrahydro-s-indacene (5.0 g, 21 mmol), phenylboronic acid (3.1 g, 25 mmol), potassium phosphate n-hydrate (10.6 g, 43 mmol), palladium acetate (0.16 g, 0.70 mmol), dicyclohexylbiphenylylphosphine (0.46 g, 1.3 mmol) and toluene (400 mL) were added and heated under reflux for one hour.

The obtained solution was subjected to liquid separation and removal of solvent by distillation to quantitatively yield 4-phenyl-1,2,3,5-tetrahydro-s-indacene (5.0 g, 22 mmol) as a yellow-brown oily substance.

(1-3) Synthesis of 6-(5-methyl-2-furyl)-4-phenyl-1,2,3,5-tetrahydro-s-indacene

4-Phenyl-1,2,3,5-tetrahydro-s-indacene (5.0 g, 22 mmol), dimethylsulfoxide (50 mL) and water (1.5 mL) were put in a 300-mL eggplant flask, and N-bromosuccinimide (6.3 g, 35 mmol) was gradually added, followed by stirring for 3 hours at room temperature. Toluene extraction was performed by adding toluene (200 mL) and water (100 mL) at room temperature, and after extraction with toluene, the organic layer was washed with dilute hydrochloric acid, water and saturated brine, left standing still overnight, added with p-toluenesulfonic acid monohydrate (0.56 g, 2.9 mmol), and heated under reflux for 30 minutes.

The obtained solution was washed with an aqueous sodium hydrogencarbonate, subjected to liquid separation and removal of solvent by distillation, and then washed with hexane to obtain 6-bromo-4-phenyl-1,2,3,5-tetrahydro-s-indacene (5.8 g, 19 mmol) as an ocher solid with 85% yield.

On the other hand, 2-methylfuran (2.3 g, 28 mmol) and dimethoxyethane (25 mL) were put in a 300 mL three-neck flask, and an n-hexane solution (19 mL, 31 mmol, 1.62 M) of n-butyllithium was added dropwise under ice cooling. After stirring for 2.5 hours, dimethoxyethane (25 mL) was added, and trimethyl borate (3.4 mL, 31 mmol) was added dropwise under ice cooling. The resulting solution was left standing still overnight at room temperature and ice-cooled, and sodium carbonate (3.9 g, 37 mmol) and water (30 mL) were added, followed by stirring for one hour at room temperature. After the solvent was concentrated under reduced pressure to half of the amount, separately synthesized 6-bromo-4-phenyl-1,2,3,5-tetrahydro-s-indacene (5.8 g, 19 mmol), bis(triphenylphosphine)dichloropalladium (0.14 g, 0.19 mmol), dimethoxyethane (45 mL) and water (6 mL) were added, and the mixture was heated under reflux for 1.5 hours.

The obtained solution was subjected to liquid separation and removal of solvent by distillation and then gel-filtered to obtain 6-(5-methyl-2-furyl)-4-phenyl-1,2,3,5-tetrahydro-s-indacene (5.0 g, 16 mmol) as a yellow-brown oily substance with 86% yield.

(1-4) Synthesis of 1,1-bis[2-(5-methyl-2-furyl)-4-phenyl-1,5,6,7-tetrahydro-s-indacen-1-yl]silacyclobutane 4-Phenyl-6-(5-methyl-2-furyl)-1,2,3,5-tetrahydro-s-indacene (5.0 g, 16.0 mmol) was dissolved in tetrahydrofuran (80 mL), and an n-hexane solution (1.65 M, 11 mL) of n-butyllithium was added dropwise at −78° C. After stirring for 3 hours while gradually raising the temperature to room temperature, N-methylimidazole (0.03 mL) and 1,1-dichlorosilacyclobutane (0.97 mL, 8.2 mmol) were added dropwise at −78° C., and the resulting solution was stirred for 2 hours while gradually raising the temperature to room temperature. The organic layer was separated by adding water and dried over magnesium sulfate and after removing the solvent by distillation under reduced pressure, the residue was filtered on silica gel to obtain 1,1-bis[2-(5-methyl-2-furyl)-4-phenyl-1,5,6,7-tetrahydro-s-indacen-1-yl]silacyclobutane (4.9 g).

(1-5) Synthesis of dichlorosilacyclobutylenebis[2-(5-methyl-2-furyl)-4-phenyl-1,5,6,7-tetrahydro-s-indacen-1-yl]zirconium (Metallocene A)

1,1-Bis[2-(5-methyl-2-furyl)-4-phenyl-1,5,6,7-tetrahydro-s-indacen-1-yl]silacyclobutane (4.9 g) was dissolved in diethyl ether (63 mL) and toluene (16 mL), and an n-hexane solution (1.65 M, 9.4 mL) of n-butyllithium was added dropwise at −78° C. After stirring for 2 hours while gradually raising the temperature to room temperature, toluene (233 mL) was added, and zirconium tetrachloride (1.6 g) was added at −78° C. After stirring for 15 hours while raising the temperature to room temperature, the obtained reaction solution was once concentrated and extracted with n-hexane and n-hexane-dichloromethane. Subsequently, crystallization from n-hexane-toluene was repeated to obtain 0.5 g of a racemic form of dichlorosilacyclobutylenebis[2-(5-methyl-2-furyl)-4-phenyl-1,5,6,7-tetrahydro-s-indacen-1-yl]zirconium.

$^1$H-NMR (400 MHz, C$_6$D$_6$) δ 1.64-1.82 (m, 4H), 1.90 (s, 6H), 2.26-2.44 (m, 4H), 2.60-2.86 (m, 10H), 5.45 (d, J=3.1 Hz, 2H), 6.24 (d, J=3.1 Hz, 2H), 6.90-7.28 (m, 6H), 7.51 (s, 2H), 7.60-7.90 (br, 2H).

(1-6) Acid Treatment and Salt Treatment of Smectite-Group Ion-Exchange Layered Silicate Acid Treatment Distilled water (1,130 g) and 96% sulfuric acid (750 g) were added to a separable flask, and the inner temperature was kept at 90° C. Thereto, Benclay SL produced by Mizusawa Industrial Chemicals, Ltd. (average particle diameter: 19 μm, 300 g) as granulated montmorillonite was added, and reaction was allowed to proceed for 2 hours. The suspension solution was cooled to room temperature over one hour and washed with distilled water until pH=4. The magnification ratio of washing here was 1/10,000 or less.

Salt Treatment:

In a separable flask, lithium sulfate monohydrate (210 g) was dissolved in distilled water (520 g), and a filtered acid-treated clay was added thereto, followed by stirring for 120 minutes at room temperature. The resulting slurry was filtered and to the obtained solid, distilled water (3,000 mL)

was added, followed by stirring for 5 minutes at room temperature. The resulting slurry was filtered. An operation of adding distilled water (2,500 mL) to the obtained solid, stirring the solution for 5 minutes, and again filtering the slurry was further repeated 4 times. The obtained solid was predried for 2 days at 130° C. in a nitrogen stream and after removing coarse particles of 53 μm or more, further dried under reduced pressure at 200° C. for 2 hours to obtain chemically treated montmorillonite.

(1-7) Preparation of Catalyst Using Metallocene Complex A (Catalyst A)

Chemically treated montmorillonite (10 g) obtained above was weighed in a flask with an inner volume of 1 L, and 65 ml of heptane and a heptane solution (35 mL, 25.3 mmol) of triisobutylaluminum were added, followed by stirring for one hour at room temperature. The solution was then washed with heptane to a residual liquid ratio of 1/100 to finally prepare a slurry in an amount of 100 mL. A heptane solution (3.3 mL) of triisobutylaluminum was added thereto, followed by stirring for 10 minutes at room temperature, and a toluene (60 mL) solution of Metallocene Complex A (257 mg, 300 μmol) was further added, followed by stirring for 60 minutes at room temperature.

Next, heptane (340 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the temperature was raised to 50° C. and maintained as it is for 2.5 hours. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure to recover 29.9 g of a solid catalyst (Catalyst A). The prepolymerization magnification (a value obtained by dividing the amount of prepolymerized polymer by the amount of solid catalyst) was 1.91.

(1-8) Propylene-Propylene.Ethylene Two-Stage Polymerization by Catalyst A

First Step:
After the inside of a stirring-type autoclave with an inner volume of 3 L was sufficiently replaced by a propylene gas, an n-heptane solution (2.76 mL, 2.02 mmol) of triisobutylaluminum was added, and hydrogen (300 mL) and subsequently liquid propylene (750 g) were introduced. The temperature was raised to 65° C., and this temperature was maintained. Catalyst A was slurried in n-heptane and injected as a catalyst in an amount of 30 mg (excluding the weight of prepolymerized polymer) under pressure to start polymerization. The temperature inside the reactor was maintained at 65° C. and after the elapse of one hour from the injection of catalyst, the residual monomer was purged to replace the inside of the reactor by an argon gas. Stirring was stopped and while flowing an argon gas, a tube was inserted into the reactor to extract a small amount of a propylene polymer component (PP).

Second Step:
A propylene gas and an ethylene gas were thereafter introduced at an inner temperature of 60° C. until reaching 1.8 MPa to provide a gas molar composition of propylene/ethylene=60/40, and the inner temperature was raised to 80° C. Subsequently, the polymerization reaction was controlled for 30 minutes while introducing a mixed gas prepared in advance of propylene and ethylene and adjusting the inner pressure to 2.0 MPa.

As a result, 277 g of a propylene-propylene.ethylene two-stage polymer with good particle properties was obtained. The average gas molar composition in the reactor during the polymerization of propylene and ethylene was propylene/ethylene=57/43.

In the two-stage polymer obtained above, from the results of CFC-IR, the rubber content (CP content) was 42 wt %, the ethylene content in rubber (CP) was 38 mol %, and the weight average molecular weight (Mw) of the CP moiety was 168,000. The rubber polymerization activity (CP activity) was 10,100 (g-CP/g-Cat/hr).

Tm of the propylene polymer component (PP) separately collected in the first step was 162° C., MFR was 0.8 (dg/min), and the PP polymerization activity (first step activity) was 5,800 (g-PP/g-Cat/hr).

The results are shown together in Table 1.

Example 2

Metallocene Complex B

Synthesis of dichlorosilacyclopentylenebis[2-(5-methyl-2-furyl)-4-phenyl-1,5,6,7-tetrahydro-s-indacen-1-yl]zirconium (Metallocene Complex B)

(2-1) Synthesis of 1,1-bis[2-(5-methyl-2-furyl)-4-phenyl-1,5,6,7-tetrahydro-s-indacen-1-yl]silacyclopentane 4-Phenyl-6-(5-methyl-2-furyl)-1,2,3,5-tetrahydro-s-indacene (5.0 g, 16.0 mmol) was dissolved in tetrahydrofuran (75 mL), and an n-hexane solution (1.58 M, 11 mL) of n-butyllithium was added dropwise at −78° C. After stirring for 3 hours while gradually raising the temperature to room temperature, N-methylimidazole (0.06 mL) and 1,1-dichlorosilacyclobutane (1.1 mL, 8.4 mmol) were added dropwise at −78° C., and the resulting solution was stirred for 2.5 hours while gradually raising the temperature to room temperature. The organic layer was separated by adding water and dried over magnesium sulfate and after removing the solvent by distillation under reduced pressure, the residue was subjected to silica gel column chromatography to obtain 1,1-bis[2-(5-methyl-2-furyl)-4-phenyl-1,5,6,7-tetrahydro-s-indacen-1-yl]silacyclobutane (3.0 g).

(2-2) Synthesis of dichlorosilacyclopentylenebis[2-(5-methyl-2-furyl)-4-phenyl-1,5,6,7-tetrahydro-s-indacen-1-yl]zirconium (Metallocene Complex B)

1,1-Bis[2-(5-methyl-2-furyl)-4-phenyl-1,5,6,7-tetrahydro-s-indacen-1-yl]silacyclopentane (3.0 g) was dissolved in diethyl ether (38 mL) and toluene (9.5 mL), and an n-hexane solution (1.58 M, 6.0 mL) of n-butyllithium was added dropwise at −78° C. After stirring for 3 hours while gradually raising the temperature to room temperature, toluene (141 mL) was added, and zirconium tetrachloride (1.1 g) was added at −78° C. After stirring for 16 hours while gradually raising the temperature to room temperature, the obtained reaction solution was once concentrated and repeatedly extracted with n-hexane and toluene to obtain 0.4 g of a racemic form of dichlorosilacyclopentylenebis[2-(5-methyl-2-furyl)-4-phenyl-1,5,6,7-tetrahydro-s-indacen-1-yl]zirconium.

$^1$H-NMR (400 MHz, C$_6$D$_6$) δ 1.66-1.84 (m, 6H), 1.96-2.20 (m, 4H), 2.16 (s, 6H), 2.36-2.46 (m, 2H), 2.50-2.70 (m, 4H), 2.74-2.92 (m, 4H), 5.72 (d, J=3.1 Hz, 2H), 6.30 (d, J=3.1 Hz, 2H), 6.89 (s, 2H), 7.00-7.28 (m, 10H), 7.60-7.90 (br, 2H).

(2-3) Preparation of Catalyst Using Metallocene Complex B (Catalyst B)

Chemically treated montmorillonite (10 g) obtained above was weighed in a flask with an inner volume of 1 L, and 65 ml of heptane and a heptane solution (35 mL, 25.3 mmol) of triisobutylaluminum were added, followed by stirring for one hour at room temperature. The solution was then washed with heptane to a residual liquid ratio of 1/100 to finally prepare a slurry in an amount of 100 mL. A heptane solution (3.3 mL) of triisobutylaluminum was added thereto, followed by stirring for 10 minutes at room temperature, and a toluene (60 mL) solution of Metallocene Complex B (260 mg, 300 μmol) was further added, followed by stirring for 60 minutes at room temperature.

Next, heptane (340 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the temperature was raised to 50° C. and maintained as it is for 2.5 hours. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure to recover 28.4 g of a solid catalyst (Catalyst B). The prepolymerization magnification (a value obtained by dividing the amount of prepolymerized polymer by the amount of solid catalyst) was 1.76.

(2-4) Propylene-Propylene.Ethylene Two-Stage Polymerization by Catalyst B

First Step:

After the inside of a stirring-type autoclave with an inner volume of 3 L was sufficiently replaced by a propylene gas, an n-heptane solution (2.76 mL, 2.02 mmol) of triisobutylaluminum was added, and hydrogen (300 mL) and subsequently liquid propylene (750 g) were introduced. The temperature was raised to 65° C., and this temperature was maintained. Catalyst B was slurried in n-heptane and injected as a catalyst in an amount of 30 mg (excluding the weight of prepolymerized polymer) under pressure to start polymerization. The temperature inside the reactor was maintained at 65° C. and after the elapse of one hour from the injection of catalyst, the residual monomer was purged to replace the inside of the reactor by an argon gas. Stirring was stopped and while flowing an argon gas, a tube was inserted into the reactor to extract a small amount of a propylene polymer component (PP).

Second Step:

A propylene gas and an ethylene gas were thereafter introduced at an inner temperature of 60° C. until reaching 1.8 MPa to provide a gas molar composition of propylene/ethylene=60/40, and the inner temperature was raised to 80° C. Subsequently, the polymerization reaction was controlled for 30 minutes while introducing a mixed gas prepared in advance of propylene and ethylene and adjusting the inner pressure to 2.0 MPa.

As a result, 194 g of a propylene-propylene.ethylene two-stage polymer with good particle properties was obtained. The average gas molar composition in the reactor during the polymerization of propylene and ethylene was propylene/ethylene=44/56.

In the two-stage polymer obtained above, from the results of CFC-IR, the rubber content (CP content) was 28 wt %, the ethylene content in rubber (CP) was 56 mol %, and the weight average molecular weight (Mw) of the CP moiety was 192,000. The rubber polymerization activity (CP activity) was 11,100 (g-CP/g-Cat/hr).

Tm of the propylene polymer component (PP) separately collected in the first step was 161° C., MFR was 7.7 (dg/min), and the PP polymerization activity (first step activity) was 4,300 (g-PP/g-Cat/hr).

The results are shown together in Table 1.

Example 3

Metallocene Complex C

Synthesis of dichlorosilacyclobutylenebis[2-(5-methyl-2-furyl)-4-phenyl-5,6-dimethyl-1-indenyl]zirconium (3-1) Synthesis of 5,6-dimethyl-indanone A mixed solution of 48 mL (0.4 mol) of o-xylene and 50 g of 3-chloropropionyl chloride was added dropwise, on an ice bath, to a suspension solution of 116 g (0.87 mol) of aluminum chloride and 200 mL of nitromethane. The temperature was raised to room temperature and after stirring for 5 hours, the reaction solution was poured in 1 N hydrochloric acid-ice water, followed by stirring. The organic layer was separated, washed with 1 N hydrochloric acid, water and saturated brine, and then dried over magnesium sulfate. The solvent was removed by distillation under reduced pressure, and a solid obtained halfway was separated. The solid obtained was added little by little to 300 mL of sulfuric acid and heated under stirring at 100° C. for 4 hours on an oil bath. About 40% of a cyclic isomer was yielded as a byproduct. After the completion of reaction, the reaction solution was poured in ice water and extracted with diethyl ether, and the organic layer was washed with water and saturated brine and then dried over magnesium sulfate. The solvent was removed by distillation under reduced pressure, and the obtained solid was recrystallized from hot hexane to remove the cyclic isomer and obtain 25.5 g of 5,6-dimethyl-indanone (yield: 40%).

$^1$H-NMR (400 MHz, CDCl$_3$) δ 2.26 (s, 3H, tol-Me), 2.35 (s, 3H, tol-Me), 2.66 (d, J=4 Hz, 2H, CH$_2$), 3.05 (d, J=4 Hz, 2H, CH$_2$), 7.25 (s, 1H, arm), 7.53 (s, 1H, arm).

(3-2) Synthesis of 4-bromo-5,6-dimethyl-indene 25.5 g of 5,6-dimethyl-indanone obtained was added to a suspension solution of 49 g of aluminum chloride and 250 mL of chloroform. After stirring at room temperature for 3 hours, 10 mL of a chloroform solution of 8.2 mL of bromine was added dropwise under cooling on an ice bath and reacted day and night at room temperature. After the completion of reaction, the reaction solution was poured in 1 N hydrochloric acid-ice water, followed by stirring. The organic layer was liquid-separated, washed with 1 N hydrochloride acid, water and saturated brine, and then dried over magnesium sulfate. The solvent was removed by distillation under reduced pressure, and the resulting solid was washed with hexane. The obtained 33 g of a crude product of 4-bromo-5,6-dimethylindanone was suspended in ethanol, and 5.2 g of sodium borohydride was added under cooling on an ice bath, followed by stirring day and night at room temperature. After the reaction, about half of the solvent was removed by distillation under reduced pressure, and the residue was quenched by the addition of 1 N hydrochloric acid and then extracted with diethyl ether.

The organic layer was washed successively with water and saturated brine and dried over magnesium sulfate, and the solvent was removed by distillation under reduced pressure. To the obtained yellow solid, 0.5 g of p-toluenesulfonic acid and 250 mL of toluene were added and heated under reflux. After 0.5 hours, the organic layer was separated by adding water, washed with saturated brine, and then dried over magnesium sulfate. The solvent was removed by distillation, and the obtained crude product was purified by silica gel chromatography to obtain 13 g of the target 4-bromo-5,6-dimethyl-indene (yield: 37%).

$^1$H-NMR (400 MHz, CDCl$_3$) δ 2.37 (s, 3H, tol-Me), 2.41 (s, 3H, tol-Me), 3.37 (s, 2H, CH$_2$), 6.51 (d, 1H, CH), 6.82 (d, 1H, CH), 7.14 (s, 1H, arm).

(3-3) Synthesis of 4-phenyl-5,6-dimethylindene

Phenylboronic acid (5.7 g, 46.7 mmol), tripotassium phosphate n-hydrate (15.2 g), 4-bromo-5,6-dimethylindene (8 g, 36 mmol), palladium acetate (0.24 g, 1.1 mmol %), and biphenyldicyclohexylphosphine (0.75 g) were dissolved in 200 mL of anhydrous toluene and reacted by heating under reflux for 0.5 hours. The reaction solution was poured in 1 N hydrochloric acid-ice water and after stirring, the organic layer was separated. The obtained organic layer was washed with saturated brine and dried over magnesium sulfate and after removing the solvent by distillation under reduced pressure, the residue was filtered on silica gel to obtain a crude product (7.7 g) of 4-phenyl-5,6-dimethylindene.

(3-4) Synthesis of 2-bromo-4-phenyl-5,6-dimethylindene

The crude product (10.6 g, 48 mmol) of 4-phenyl-5,6-dimethylindene was dissolved in dimethyl sulfoxide (120 mL), and water (4 mL) was added. N-Bromosuccinimide (11.1 g, 62 mmol) was added thereto at 0° C., followed by stirring for 4 hours at room temperature, and the resulting solution was quenched by the addition of water on an ice bath. The organic layer was extracted by adding toluene, and p-toluenesulfonic acid monohydrate (0.2 g) was added to the organic layer and reacted by heating under reflux for 2 hours. Thereafter, water was added to the reaction solution, and the organic layer was separated. The obtained organic layer was washed with saturated brine and dried over magnesium sulfate and after removing the solvent by distillation under reduced pressure, the residue was filtered on silica gel to obtain a crude product (12.5 g).

(3-5) Synthesis of 2-(5-methyl-2-furyl)-4-phenyl-5,6-dimethylindene

2-Methylfuran (5.9 mL, 65.8 mmol) was dissolved in dimethoxyethane (100 mL), and an n-hexane solution (1.62 M, 40.4 mL) of n-butyllithium was added dropwise under cooling on an ice bath, followed by stirring for 2 hours. Thereafter, while continuing cooling on an ice bath, trimethyl borate (8.5 mL, 75 mmol) was added dropwise, and the resulting solution was stirred for 16 hours at room temperature. Water (5 mL) was added and after stirring for one hour, the solvent was removed by distillation under reduced pressure. Thereto, an aqueous solution (80 mL) of sodium carbonate (8.8 g), a dimethoxyethane (60 mL) solution of the crude product (12.5 g) of 2-bromo-4-phenyl-5,6-dimethylindene synthesized above, and tetrakis(triphenylphosphine)palladium (1.2 g) were sequentially added and reacted by heating under reflux for 2 hours. The reaction solution was poured in 1 N hydrochloric acid-ice water, and the organic layer was separated, washed with 1 N hydrochloric acid and saturated brine, and dried over magnesium sulfate. The solvent was removed by distillation under reduced pressure, and the residue was recrystallized to obtain the target 2-(5-methyl-2-furyl)-4-phenyl-5,6-dimethylindene (7.3 g).

(3-6) Synthesis of 1,1-bis[2-(5-methyl-2-furyl)-4-phenyl-5,6-dimethylindenyl]silacyclobutane 2-(5-Methyl-2-furyl)-4-phenyl-5,6-dimethylindene (5.0 g, 16.7 mmol) was dissolved in tetrahydrofuran (78 mL), and an n-hexane solution (1.58 M, 12 mL) of n-butyllithium was added dropwise at −78° C. After stirring for 3 hours while gradually raising the temperature to room temperature, N-methylimidazole (0.03 mL) and 1,1-dichlorosilacyclobutane (1.0 mL, 8.4 mmol) were added dropwise at −78° C., and the resulting solution was stirred for 2 hours while gradually raising the temperature to room temperature. The organic layer was separated by adding water and dried over magnesium sulfate and after removing the solvent by distillation under reduced pressure, the residue was subjected to silica gel column chromatography to obtain 1,1-bis[2-(5-methyl-2-furyl)-4-phenyl-5,6-dimethylindenyl]silacyclobutane (5.7 g).

(3-7) Synthesis of dichlorosilacyclobutylenebis[2-(5-methyl-2-furyl)-4-phenyl-5,6-dimethyl-1-indenyl]zirconium (Metallocene Complex C)

1,1-Bis[2-(5-methyl-2-furyl)-4-phenyl-5,6-dimethylindenyl]silacyclobutane (6.6 g) was dissolved in diethyl ether (120 mL), and an n-hexane solution (1.58 M, 14 mL) of n-butyllithium was added dropwise at −78° C. After stirring for 3 hours while gradually raising the temperature to room temperature, the obtained reaction solution was once concentrated, dichloromethane (237 mL) was added, and zirconium tetrachloride (2.3 g) was added at −78° C. After stirring for 3 hours while gradually raising the temperature to room temperature, the obtained reaction solution was once concentrated and extracted with n-hexane and n-hexane-dichloromethane. Subsequently, extraction with toluene was repeated to obtain 1.7 g of a racemic form of dichlorosilacyclobutylenebis[2-(5-methyl-2-furyl)-4-phenyl-5,6-dimethyl-1-indenyl]zirconium.

$^1$H-NMR (400 MHz, C$_6$D$_6$) δ 1.92 (s, 6H), 2.10 (s, 6H), 2.13 (s, 6H), 2.18-2.30 (m, 2H), 2.58-2.80 (m, 4H), 5.69 (d, J=3.2 Hz, 2H), 6.16 (d, J=3.2 Hz, 2H), 6.78 (s, 2H), 6.83 (s, 2H), 7.06-7.22 (m, 6H), 7.28 (t, J=7.8 Hz, 2H), 8.23 (d, J=7.8 Hz, 2H).

(3-8) Preparation of Catalyst Using Metallocene Complex C (Catalyst C)

Chemically treated montmorillonite (10 g) obtained above was weighed in a flask with an inner volume of 1 L, and 65 mL of heptane and a heptane solution (35 mL, 25.3 mmol) of triisobutylaluminum were added, followed by stirring for one hour at room temperature. The solution was then washed with heptane to a residual liquid ratio of 1/100 to finally prepare a slurry in an amount of 100 mL. A heptane solution (3.3 mL) of triisobutylaluminum was added thereto, followed by stirring for 10 minutes at room temperature, and a toluene (60 mL) solution of Metallocene Complex C (249 mg, 300 μmol) was further added, followed by stirring for 60 minutes at room temperature.

Next, heptane (340 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the temperature was raised to 50° C. and maintained as it is for 2 hours. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure to recover 31.1 g of a solid catalyst (Catalyst C). The prepolymerization magnification (a value obtained by dividing the amount of prepolymerized polymer by the amount of solid catalyst) was 2.02.

(3-9) Propylene-Propylene.Ethylene Two-Stage Polymerization by Catalyst C

First Step:

After the inside of a stirring-type autoclave with an inner volume of 3 L was sufficiently replaced by a propylene gas, an n-heptane solution (2.76 mL, 2.02 mmol) of triisobutylaluminum was added, and hydrogen (300 mL) and subsequently liquid propylene (750 g) were introduced. The temperature was raised to 65° C., and this temperature was maintained. Catalyst C was slurried in n-heptane and injected as a catalyst in an amount of 20 mg (excluding the weight of prepolymerized polymer) under pressure to start polymerization. The temperature inside the reactor was maintained at 65° C. and after the elapse of one hour from the injection of catalyst, the residual monomer was purged to replace the inside of the reactor by an argon gas. Stirring was stopped and while flowing an argon gas, a tube was inserted into the reactor to extract a small amount of a propylene polymer component (PP).

Second Step:

A propylene gas and an ethylene gas were thereafter introduced at an inner temperature of 60° C. until reaching 1.8 MPa to provide a gas molar composition of propylene/ethylene=60/40, and the inner temperature was raised to 80° C. Subsequently, the polymerization reaction was controlled for 30 minutes while introducing a mixed gas prepared in advance of propylene and ethylene and adjusting the inner pressure to 2.0 MPa.

As a result, 228 g of a propylene-propylene.ethylene two-stage polymer with good particle properties was obtained. The average gas molar composition in the reactor during the polymerization of propylene and ethylene was propylene/ethylene=54/46.

In the two-stage polymer obtained above, from the results of CFC-IR, the rubber content (CP content) was 52 wt %, the ethylene content in rubber (CP) was 41 mol %, and the weight average molecular weight (Mw) of the CP moiety was 351,000. The rubber polymerization activity (CP activity) was 7,400 (g-CP/g-Cat/hr).

Tm of the propylene polymer component (PP) separately collected in the first step was 160° C., MFR was 3.4 (dg/min), and the PP polymerization activity (first step activity) was 6,100 (g-PP/g-Cat/hr).

The results are shown together in Table 1.

Example 4

Metallocene Complex D

Synthesis of dichlorosilacyclobutylenebis[2-(4,5-dimethyl-2-furyl)-4-phenyl-5,6-dimethyl-1-indenyl]zirconium (4-1) Synthesis of 2-(4,5-dimethyl-2-furyl)-4-phenyl-5,6-dimethylindene 2,3-Dimethylfuran (4.8 mL, 50.2 mmol) was dissolved in dimethoxyethane (46 mL), and an n-hexane solution (1.58 M, 35.2 mL) of n-butyllithium was added dropwise at −40° C. After stirring for 3 hours while gradually raising the temperature to room temperature, trimethyl borate (6.2 mL, 56 mmol) was added dropwise, and the resulting solution was stirred for 2 hours while gradually raising the temperature to room temperature and then stirred for 16 hours at room temperature. An aqueous solution (46 mL) of sodium carbonate (7.2 g) was added, followed by stirring for one hour, and the solvent was removed by distillation under reduced pressure. Thereto, a dimethoxyethane (80 mL) solution of 2-bromo-4-phenyl-5,6-dimethylindene (10.0 g), water (10 mL), and bis(triphenylphosphine)palladium dichloride (0.25 g) were sequentially added and reacted by heating under reflux for 3 hours. After adding 1 N hydrochloric acid to the reaction solution, the organic layer was separated, washed with an aqueous sodium carbonate solution and saturated brine, and dried over magnesium sulfate, and the solvent was removed by distillation under reduced pressure. The residue was subjected to silica gel column chromatography to obtain the target 2-(4,5-dimethyl-2-furyl)-4-phenyl-5,6-dimethylindene (6.6 g).

(4-2) Synthesis of 1,1-bis[2-(4,5-dimethyl-2-furyl)-4-phenyl-5,6-dimethylindenyl]silacyclobutane 2-(4,5-Dimethyl-2-furyl)-4-phenyl-5,6-dimethylindene (6.6 g, 21.0 mmol) was dissolved in tetrahydrofuran (100 mL), and an n-hexane solution (1.58 M, 13 mL) of n-butyllithium was added dropwise at −78° C. After stirring for 3 hours while gradually raising the temperature to room temperature, N-methylimidazole (0.04 mL) and 1,1-dichlorosilacyclobutane (1.3 mL, 10.5 mmol) were added dropwise at −78° C., and the resulting solution was stirred for 3 hours while gradually raising the temperature to room temperature. The organic layer was separated by adding water and dried over magnesium sulfate and after removing the solvent by distillation under reduced pressure, the residue was extracted with hexane to obtain 1,1-bis[2-(4,5-dimethyl-2-furyl)-4-phenyl-5,6-dimethylindenyl]silacyclobutane (4.9 g).

(4-3) Synthesis of dichlorosilacyclobutylenebis[2-(4,5-dimethyl-2-furyl)-4-phenyl-5,6-dimethyl-1-indenyl]zirconium (Metallocene Complex D)

1,1-Bis[2-(4,5-dimethyl-2-furyl)-4-phenyl-5,6-dimethylindenyl]silacyclobutane (4.9 g) was dissolved in diethyl ether (84 mL), and an n-hexane solution (1.58 M, 9.7 mL) of n-butyllithium was added dropwise at −78° C. After stirring for 3 hours while gradually raising the temperature to room temperature, the obtained reaction solution was once concentrated, dichloromethane (167 mL) was added, and zirconium tetrachloride (1.7 g) was added at −78° C. After stirring for 3 hours while gradually raising the temperature to room temperature, the obtained reaction solution was once concentrated and extracted with dichloromethane and n-hexane. Subsequently, extraction with toluene was repeated to obtain 2.0 g of a racemic form of dichlorosilacyclobutylenebis[2-(4,5-dimethyl-2-furyl)-4-phenyl-5,6-dimethyl-1-indenyl]zirconium.

$^1$H-NMR (400 MHz, C$_6$D$_6$) δ 1.65 (s, 6H), 1.90 (s, 6H), 2.09 (s, 6H), 2.11 (s, 6H), 2.20-2.34 (m, 2H), 2.64-2.82 (m, 4H), 5.97 (s, 2H), 6.79 (s, 4H), 6.98-7.24 (m, 6H), 7.30 (t, J=7.6 Hz, 2H), 8.23 (d, J=7.6 Hz, 2H).

(4-4) Preparation of Catalyst Using Metallocene Complex D (Catalyst D)

Chemically treated montmorillonite (10 g) obtained above was weighed in a flask with an inner volume of 1 L, and 65 mL of heptane and a heptane solution (35 mL, 25.3 mmol) of triisobutylaluminum were added, followed by stirring for one hour at room temperature. The solution was then washed with heptane to a residual liquid ratio of 1/100 to finally prepare a slurry in an amount of 100 mL. A heptane solution (3.3 mL) of triisobutylaluminum was added thereto, followed by stirring for 10 minutes at room temperature, and a toluene (60 mL) solution of Metallocene Complex D (257 mg, 300 µmol) was further added, followed by stirring for 60 minutes at room temperature.

Next, heptane (340 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the temperature was raised to 50° C. and maintained as it is for 2 hours. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure to recover 32.2 g of a solid catalyst (Catalyst D). The prepolymerization magnification (a value obtained by dividing the amount of prepolymerized polymer by the amount of solid catalyst) was 2.11.

(4-5) Propylene-Propylene.Ethylene Two-Stage Polymerization by Catalyst D

First Step:
After the inside of a stirring-type autoclave with an inner volume of 3 L was sufficiently replaced by a propylene gas, an n-heptane solution (2.76 mL, 2.02 mmol) of triisobutylaluminum was added, and hydrogen (300 mL) and subsequently liquid propylene (750 g) were introduced. The temperature was raised to 65° C., and this temperature was maintained. Catalyst D was slurried in n-heptane and injected as a catalyst in an amount of 20 mg (excluding the weight of prepolymerized polymer) under pressure to start polymerization. The temperature inside the reactor was maintained at 65° C. and after the elapse of one hour from the injection of catalyst, the residual monomer was purged to replace the inside of the reactor by an argon gas. Stirring was stopped and while flowing an argon gas, a tube was inserted into the reactor to extract a small amount of a propylene polymer component (PP).

Second Step:
A propylene gas and an ethylene gas were thereafter introduced at an inner temperature of 60° C. until reaching 1.8 MPa to provide a gas molar composition of propylene/ethylene=60/40, and the inner temperature was raised to 80° C. Subsequently, the polymerization reaction was controlled for 30 minutes while introducing a mixed gas prepared in advance of propylene and ethylene and adjusting the inner pressure to 2.0 MPa.

As a result, 177 g of a propylene-propylene.ethylene two-stage polymer with good particle properties was obtained. The average gas molar composition in the reactor during the polymerization of propylene and ethylene was propylene/ethylene=45/55.

In the two-stage polymer obtained above, from the results of CFC-IR, the rubber content (CP content) was 36 wt %, the ethylene content in rubber (CP) was 51 mol %, and the weight average molecular weight (Mw) of the CP moiety was 521,000. The rubber polymerization activity (CP activity) was 9,400 (g-CP/g-Cat/hr).

Tm of the propylene polymer component (PP) separately collected in the first step was 161° C., MFR was 1.6 (dg/min), and the PP polymerization activity (first step activity) was 7,000 (g-PP/g-Cat/hr).

The results are shown together in Table 1.

Example 5

Metallocene Complex E

Synthesis of dichlorosilacyclobutylenebis[2-(5-tert-butyl-2-furyl)-4-phenyl-5,6-dimethyl-1-indenyl] zirconium

(5-1) Synthesis of 2-(5-tert-butyl-2-furyl)-4-phenyl-5,6-dimethylindene 2-tert-Butylfuran (6.2 mL, 50.3 mmol) was dissolved in dimethoxyethane (46 mL), and an n-hexane solution (1.58 M, 35.2 mL) of n-butyllithium was added dropwise under at −40° C. After stirring for 3 hours while raising the temperature to room temperature, trimethyl borate (6.2 mL, 56 mmol) was added dropwise, and the resulting solution was stirred for 4 hours while gradually raising the temperature to room temperature and then stirred for 16 hours at room temperature. An aqueous solution (46 mL) of sodium carbonate (7.2 g) was added, followed by stirring for one hour, and the solvent was removed by distillation under reduced pressure. Thereto, a dimethoxyethane (80 mL) solution of 2-bromo-4-phenyl-5,6-dimethylindene (10.0 g), water (10 mL), and bis(triphenylphosphine)palladium dichloride (0.25 g) were sequentially added and reacted by heating under reflux for 2 hours. After adding 1 N hydrochloric acid to the reaction solution, the organic layer was separated, washed with an aqueous sodium carbonate solution and saturated brine, and dried over magnesium sulfate, and the solvent was removed by distillation under reduced pressure. The residue was subjected to silica gel column chromatography to obtain the target 2-(5-tert-butyl-2-furyl)-4-phenyl-5,6-dimethylindene (7.4 g).

(5-2) Synthesis of 1,1-bis[2-(5-tert-butyl-2-furyl)-4-phenyl-5,6-dimethylindenyl]silacyclobutane 2-(5-tert-Butyl-2-furyl)-4-phenyl-5,6-dimethylindene (7.4 g, 21.6 mmol) was dissolved in tetrahydrofuran (101 mL), and an n-hexane solution (1.58 M, 14 mL) of n-butyllithium was added dropwise at −78° C. After stirring for 3 hours while gradually raising the temperature to room temperature, N-methylimidazole (0.04 mL) and 1,1-dichlorosilacyclobutane (1.3 mL, 10.8 mmol) were added dropwise at −78° C., and the resulting solution was stirred for 3 hours while gradually raising the temperature to room temperature. The organic layer was separated by adding water and dried over magnesium sulfate and after removing the solvent by distillation under reduced pressure, the residue was extracted with hexane to obtain 1,1-bis[2-(5-tert-butyl-2-furyl)-4-phenyl-5,6-dimethylindenyl]silacyclobutane (4.0 g).

(5-3) Synthesis of dichlorosilacyclobutylenebis[2-(5-tert-butyl-2-furyl)-4-phenyl-5,6-dimethyl-1-indenyl]zirconium (Metallocene Complex E)

1,1-Bis[2-(5-tert-butyl-2-furyl)-4-phenyl-5,6-dimethylindenyl]silacyclobutane (4.0 g) was dissolved in diethyl ether (64 mL), and an n-hexane solution (1.58 M, 7.4 mL) of n-butyllithium was added dropwise at −78° C. After stirring for 3 hours while gradually raising the temperature to room temperature, the obtained reaction solution was once concentrated, dichloromethane (128 mL) was added, and zirconium tetrachloride (1.3 g) was added at −78° C. After stirring for 3 hours while gradually raising the temperature to room temperature, the obtained reaction solution was once concentrated and extracted with n-hexane and n-hexane-dichloromethane. Subsequently, recrystallization from toluene was repeated to obtain 1.1 g of a racemic form of dichlorosilacyclobutylenebis[2-(5-tert-butyl-2-furyl)-4-phenyl-5,6-dimethyl-1-indenyl]zirconium.

$^1$H-NMR (400 MHz, $C_6D_6$) δ 1.31 (s, 18H), 1.95 (s, 6H), 2.10 (s, 6H), 2.10-2.22 (m, 2H), 2.50-2.64 (m, 2H), 2.68-2.82 (m, 2H), 5.82 (d, J=3.2 Hz, 2H), 6.40 (d, J=3.2 Hz, 2H), 6.80 (s, 2H), 6.84 (s, 2H), 7.04-7.22 (m, 6H), 7.26 (t, J=7.6 Hz, 2H), 8.20 (d, J=7.6 Hz, 2H).

(5-4) Preparation of Catalyst Using Metallocene Complex E (Catalyst E)

Chemically treated montmorillonite (10 g) obtained above was weighed in a flask with an inner volume of 1 L, and 65 mL of heptane and a heptane solution (35 mL, 25.3 mmol) of triisobutylaluminum were added, followed by stirring for one hour at room temperature. The solution was then washed with heptane to a residual liquid ratio of 1/100 to finally prepare a slurry in an amount of 100 mL. A heptane solution (3.3 mL) of triisobutylaluminum was added thereto, followed by stirring for 10 minutes at room temperature, and a toluene (60 mL) solution of Metallocene Complex E (274 mg, 300 μmol) was further added, followed by stirring for 60 minutes at room temperature.

Next, heptane (340 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the temperature was raised to 50° C. and maintained as it is for 3 hours. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure to recover 29.0 g of a solid catalyst (Catalyst E). The prepolymerization magnification (a value obtained by dividing the amount of prepolymerized polymer by the amount of solid catalyst) was 1.78.

(5-5) Propylene-Propylene.Ethylene Two-Stage Polymerization by Catalyst E

First Step:

After the inside of a stirring-type autoclave with an inner volume of 3 L was sufficiently replaced by a propylene gas, an n-heptane solution (2.76 mL, 2.02 mmol) of triisobutylaluminum was added, and hydrogen (300 mL) and subsequently liquid propylene (750 g) were introduced. The temperature was raised to 65° C., and this temperature was maintained. Catalyst E was slurried in n-heptane and injected as a catalyst in an amount of 30 mg (excluding the weight of prepolymerized polymer) under pressure to start polymerization. The temperature inside the reactor was maintained at 65° C. and after the elapse of one hour from the injection of catalyst, the residual monomer was purged to replace the inside of the reactor by an argon gas. Stirring was stopped and while flowing an argon gas, a tube was inserted into the reactor to extract a small amount of a propylene polymer component (PP).

Second Step:

A propylene gas and an ethylene gas were thereafter introduced at an inner temperature of 60° C. until reaching 1.8 MPa to provide a gas molar composition of propylene/ethylene=60/40, and the inner temperature was raised to 80° C. Subsequently, the polymerization reaction was controlled for 30 minutes while introducing a mixed gas prepared in advance of propylene and ethylene and adjusting the inner pressure to 2.0 MPa.

As a result, 103 g of a propylene-propylene.ethylene two-stage polymer with good particle properties was obtained. The average gas molar composition in the reactor during the polymerization of propylene and ethylene was propylene/ethylene=49/51.

In the two-stage polymer obtained above, from the results of CFC-IR, the rubber content (CP content) was 20 wt %, the ethylene content in rubber (CP) was 46 mol %, and the weight average molecular weight (Mw) of the CP moiety was 305,000. The rubber polymerization activity (CP activity) was 880 (g-CP/g-Cat/hr).

Tm of the propylene polymer component (PP) separately collected in the first step was 161° C., MFR was 4.2 (dg/min), and the PP polymerization activity (first step activity) was 4,300 (g-PP/g-Cat/hr).

The results are shown together in Table 1.

Example 6

Metallocene Complex F

Synthesis of dichlorosilacyclobutylenebis[2-(5-methyl-2-furyl)-4-(3,5-dimethylphenyl)-5,6-dimethyl-1-indenyl]zirconium (6-1) Synthesis of 4-(3,5-dimethylphenyl)-5,6-dimethylindene 3,5-Dimethylphenylboronic acid (18.6 g, 124 mmol), tripotassium phosphate n-hydrate (53.2 g), 4-bromo-5,6-dimethylindene (23.2 g, 104 mmol), palladium acetate (0.79 g, 3.5 mmol %), and 2-(dicyclohexylphosphino)biphenyl (2.6 g) were dissolved in anhydrous toluene (438 mL) and reacted by heating under reflux for 3 hours. After adding 1 N hydrochloric acid to the reaction solution, the organic layer was separated. The obtained organic layer was washed with an aqueous sodium carbonate solution and saturated brine and dried over magnesium sulfate and after removing the solvent by distillation under reduced pressure, the residue was filtered on silica gel to obtain a crude product (24.5 g) of 4-(3,5-dimethylphenyl)-5,6-dimethylindene.

(6-2) Synthesis of 2-bromo-4-(3,5-dimethylphenyl)-5,6-dimethylindene 4-(3,5-Dimethylphenyl)-5,6-dimethylindene (24.5 g) was dissolved in dimethyl sulfoxide (250 mL), and water (9 mL) was added. N-Bromosuccinimide (28.7 g, 161 mmol) was added thereto at 0° C., followed by stirring for 3.5 hours at room temperature, and the resulting solution was quenched by the addition of water on an ice bath. The organic layer was extracted by adding toluene, and p-toluenesulfonic acid monohydrate (2.5 g) was added to the organic layer and reacted by heating under reflux for one hour. Thereafter, water was added to the reaction solution, and the organic layer was separated. The obtained organic layer was washed with an aqueous sodium carbonate solution and saturated brine and dried over magnesium sulfate, and the solvent was then removed by distillation under reduced pressure to obtain a crude product (33.9 g).

(6-3) Synthesis of 2-(5-methyl-2-furyl)-4-(3,5-dimethylphenyl)-5,6-dimethylindene 2-Methylfuran (3.8 mL, 46.0 mmol) was dissolved in dimethoxyethane (42 mL), and an n-hexane solution (1.58 M, 32.0 mL) of n-butyllithium was added dropwise at −40° C. After stirring for 3 hours while gradually raising the temperature to room temperature, triisopropyl borate (11.6 mL, 50.6 mmol) was added dropwise, and the resulting solution was stirred for 2 hours while gradually raising the temperature to room temperature and then stirred for 16 hours at room temperature. An aqueous solution (75 mL) of sodium carbonate (6.5 g) was added, followed by stirring for one hour. A dimethoxyethane (25 mL) solution of the crude product (10.1 of 2-bromo-4-(3,5-dimethylphenyl)-5,6-dimethylindene, and triphenylphosphine (0.18 g), and bis(triphenylphosphine)palladium dichloride (0.24 g) were sequentially added and reacted by heating under reflux for 3.5 hours. After adding 1 N hydrochloric acid to the reaction solution, the organic layer was separated, washed with an aqueous sodium carbonate solution and saturated brine, and dried over magnesium sulfate. The solvent was removed by distillation under reduced pressure, and the residue was subjected to silica gel column chromatography to obtain the target 2-(5-methyl-2-furyl)-4-(3,5-dimethylphenyl)-5,6-dimethylindene (6.4 g).

(6-4) Synthesis of 1,1-bis[2-(5-methyl-2-furyl)-4-(3,5-dimethylphenyl)-5,6-dimethylindenyl]silacyclobutane 2-(5-Methyl-2-furyl)-4-(3,5-dimethylphenyl)-5,6-dimethylindene (6.4 g, 19.4 mmol) was dissolved in tetrahydrofuran (91 mL), and an n-hexane solution (1.60 M, 12 mL) of n-butyllithium was added dropwise at −78° C. After stirring for 3 hours while gradually raising the temperature to room temperature, N-methylimidazole (0.04 mL) and 1,1-dichlorosilacyclobutane (1.2 mL, 9.7 mmol) were added dropwise at −78° C., and the resulting solution was stirred for 3 hours while gradually raising the temperature to room temperature. The organic layer was separated by adding water and dried over magnesium sulfate and after removing the solvent by distillation under reduced pressure, the residue was subjected to silica gel column chromatography to obtain 1,1-bis[2-(5-methyl-2-furyl)-4-(3,5-dimethylphenyl)-5,6-dimethylindenyl]silacyclobutane (7.1 g).

(6-5) Synthesis of dichlorosilacyclobutylenebis[2-(5-methyl-2-furyl)-4-(3,5-dimethylphenyl)-5,6-dimethyl-1-indenyl]zirconium (Metallocene Complex F)

1,1-Bis[2-(5-methyl-2-furyl)-4-(3,5-dimethylphenyl)-5,6-dimethylindenyl]silacyclobutane (7.1 g) was dissolved in diethyl ether (118 mL), and an n-hexane solution (1.60 M, 14 mL) of n-butyllithium was added dropwise at −78° C. After stirring for 2 hours while gradually raising the temperature to room temperature, the obtained reaction solution was once concentrated, dichloromethane (235 mL) was added, and zirconium tetrachloride (2.4 g) was added at −78° C. After stirring for 3 hours while gradually raising the temperature to room temperature, the obtained reaction solution was once concentrated and extracted with n-hexane and n-hexane-dichloromethane. Subsequently, extraction with toluene was repeated to obtain 1.4 g of a racemic form of dichlorosilacyclobutylenebis[2-(5-methyl-2-furyl)-4-(3,5-dimethylphenyl)-5,6-dimethyl-1-indenyl]zirconium (Metallocene Complex F).

$^1$H-NMR (400 MHz, $C_6D_6$) δ 1.96 (s, 6H), 2.13 (s, 6H), 2.14 (s, 6H), 2.16 (s, 6H), 2.21 (s, 6H), 2.08-2.30 (m, 2H), 2.58-2.82 (m, 4H), 5.69 (d, J=3.4 Hz, 2H), 6.19 (d, J=3.4 Hz, 2H), 6.79 (s, 2H), 6.81 (s, 2H), 6.84 (s, 2H), 6.91 (s, 2H), 7.89 (s, 2H).

(6-6) Preparation of Catalyst Using Metallocene Complex F (Catalyst F)

Chemically treated montmorillonite (10 g) obtained above was weighed in a flask with an inner volume of 1 L, and 65 mL of heptane and a heptane solution (35 mL, 25.3 mmol) of triisobutylaluminum were added, followed by stirring for one hour at room temperature. The solution was then washed with heptane to a residual liquid ratio of 1/100 to finally prepare a slurry in an amount of 100 mL. A heptane solution (3.3 mL) of triisobutylaluminum was added thereto, followed by stirring for 10 minutes at room temperature, and a toluene (60 mL) solution of Metallocene Complex F (266 mg, 300 μmol) was further added, followed by stirring for 60 minutes at room temperature.

Next, heptane (340 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the temperature was raised to 50° C. and maintained as it is for 2 hours. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure to recover 31.5 g of a solid catalyst (Catalyst F). The prepolymerization magnification (a value obtained by dividing the amount of prepolymerized polymer by the amount of solid catalyst) was 2.01.

(6-7) Propylene-Propylene.Ethylene Two-Stage Polymerization by Catalyst F

First Step:

After the inside of a stirring-type autoclave with an inner volume of 3 L was sufficiently replaced by a propylene gas, an n-heptane solution (2.76 mL, 2.02 mmol) of triisobutylaluminum was added, and hydrogen (300 mL) and subsequently liquid propylene (750 g) were introduced. The temperature was raised to 65° C., and this temperature was maintained. Catalyst F was slurried in n-heptane and injected as a catalyst in an amount of 20 mg (excluding the weight of prepolymerized polymer) under pressure to start polymerization. The temperature inside the reactor was maintained at 65° C. and after the elapse of one hour from the injection of catalyst, the residual monomer was purged to replace the inside of the reactor by an argon gas. Stirring was stopped and while flowing an argon gas, a tube was inserted into the reactor to extract a small amount of a propylene polymer component (PP).

Second Step:

A propylene gas and an ethylene gas were thereafter introduced at an inner temperature of 60° C. until reaching 1.8 MPa to provide a gas molar composition of propylene/ethylene=60/40, and the inner temperature was raised to 80° C. Subsequently, the polymerization reaction was controlled for 30 minutes while introducing a mixed gas prepared in advance of propylene and ethylene and adjusting the inner pressure to 2.0 MPa.

As a result, 205 g of a propylene-propylene.ethylene two-stage polymer with good particle properties was obtained. The average gas molar composition in the reactor during the polymerization of propylene and ethylene was propylene/ethylene=43/57.

In the two-stage polymer obtained above, from the results of CFC-IR, the rubber content (CP content) was 30 wt %, the ethylene content in rubber (CP) was 52 mol %, and the weight average molecular weight (Mw) of the CP moiety was 544,000. The rubber polymerization activity (CP activity) was 7,600 (g-CP/g-Cat/hr).

Tm of the propylene polymer component (PP) separately collected in the first step was 161° C., MFR was 4.0 (dg/min), and the PP polymerization activity (first step activity) was 8,500 (g-PP/g-Cat/hr).

The results are shown together in Table 1.

Example 7

Metallocene Complex G

Synthesis of dichlorosilacyclobutylenebis[2-(5-methyl-2-furyl)-4-(4-tert-butylphenyl)-5,6-dimethyl-1-indenyl]zirconium (7-1) Synthesis of 4-(4-tert-butylphenyl)-5,6-dimethylindene In 500 mL three-neck flask, 4-bromo-5,6-dimethylindene (3.4 g, 15 mmol), 4-tert-butylphenylboronic acid (3.25 g, 18.2 mmol), tripotassium phosphate n-hydrate (7.7 g, 31 mmol), palladium acetate (0.11 g, 0.5 mmol), biphenyldicyclohexylphosphine (0.33 g, 0.94 mmol) and toluene (287 mL) were added and heated under flux for 2 hours on an oil bath. The obtained solution was subjected to liquid separation and removal of solvent by distillation to obtain a crude product (4.6 g) of 4-(4-tert-butylphenyl)-5,6-dimethylindene.

(7-2) Synthesis of 2-bromo-4-(4-tert-butylphenyl)-5,6-dimethylindene

Crude 4-(4-tert-butylphenyl)-5,6-dimethylindene (4.6 g, 17 mmol), dimethylsulfoxide (41 mL) and water (1.5 mL) were put in a 500 mL eggplant flask, and N-bromosuccinimide (5.0 g, 28 mmol) was gradually added under ice cooling, followed by stirring for 3.5 hours at room temperature. Toluene (100 mL) and water (100 mL) were added at room temperature and after extraction with toluene, the organic layer was washed with water and saturated brine. The organic layer was transferred to a 500 mL three-neck flask, and p-toluenesulfonic acid monohydrate (0.50 g, 2.6 mmol) was added, followed by heating under reflux for 1.5 hours on an oil bath. The obtained solution was washed with an aqueous sodium carbonate solution and saturated brine and subjected to liquid separation and removal of solvent by distillation to obtain a crude product (5.4 g, 15 mmol) of 2-bromo-4-(4-tert-butylphenyl)-5,6-dimethylindene as a yellow-brown oily substance.

(7-3) Synthesis of 2-(5-methyl-2-furyl)-4-(4-tert-butylphenyl)-5,6-dimethylindene 2-Methylfuran (1.9 g, 23 mmol) and dimethoxyethane (21 mL) were put in a 200 mL Schlenk tube and cooled to −20° C., and an n-hexane solution (16 mL, 25 mmol, 1.63 M) of n-butyllithium was added dropwise. After stirring for one hour, dimethoxyethane (21 mL) was added, and trimethyl borate (2.9 mL, 26 mmol) was added under ice cooling, followed by stirring for one hour at room temperature. The resulting solution was ice-cooled, and sodium carbonate (3.3 g, 31 mmol) and water (21 mL) were added, followed by stirring for one hour at room temperature. After the solvent was concentrated under reduced pressure to half of the amount, 2-bromo-4-(4-tert-butylphenyl)-5,6-dimethylindene (5.4 g, 15 mmol), tetrakis(triphenylphosphine)palladium (0.44 g, 0.38 mmol), dimethoxyethane (37 mL) and water (4.8 mL) were added, and the mixture was heated under reflux for 2 hours on an oil bath. The obtained solution was subjected to liquid separation and removal of solvent by distillation and then purified by silica gel column chromatography to obtain 2-(5-methyl-2-furyl)-4-(4-tert-butylphenyl)-5,6-dimethylindene (2.7 g, 7.5 mmol) as a plate orange solid with 49% yield.

(7-4) Synthesis of 1,1-bis[2-(5-methyl-2-furyl)-4-(4-tert-butylphenyl)-5,6-dimethylindenyl]silacyclobutane 2-(5-Methyl-2-furyl)-4-(4-tert-butylphenyl)-5,6-dimethylindene (12.7 g, 35.6 mmol) and tetrahydrofuran (120 mL) were put in a 500 mL eggplant flask and cooled to −78° C., and an n-hexane solution (22 mL, 36 mmol, 1.60 M) of n-butyllithium was added dropwise. After stirring for 2 hours at −78 to 0° C., a tetrahydrofuran (30 mL) solution of N-methylimidazole (0.15 g, 1.8 mmol) was added and cooled to −50° C., and 1,1-dichlorosilacyclobutane (2.5 g, 18 mmol) was added dropwise, followed by stirring for 3 hours at −50 to 0° C. The obtained solution was subjected to liquid separation and removal of solvent by distillation and purified on silica gel to obtain 1,1-bis[2-(5-methyl-2-furyl)-

4-(4-tert-butylphenyl)-5,6-dimethylindenyl]silacyclobutane (12.8 g, 16 mmol) as a yellow solid with 92% yield.

(7-5) Synthesis of dichlorosilacyclobutylenebis[2-(5-methyl-2-furyl)-4-(4-tert-butylphenyl)-5,6-dimethyl-1-indenyl]zirconium (Metallocene Complex G)

1,1-Bis[2-(5-methyl-2-furyl)-4-(4-tert-butylphenyl)-5,6-dimethylindenyl]silacyclobutane (9.4 g, 12 mmol) and diethyl ether (200 mL) were put and cooled to −78° C., and an n-hexane solution (15 mL, 24 mmol, 1.60 M) of n-butyllithium was added dropwise. The resulting solution was gradually stirred for 3 hours at −76 to 0° C. and concentrated, and toluene (300 mL) was added. The solution was cooled to −78° C. and after adding zirconium tetrachloride (2.8 g, 12 mmol), stirred overnight while gradually raising the temperature to room temperature, and the solvent was then removed by distillation under reduced pressure. The resulting mixture was washed with hexane and extracted with dichloromethane/hexane to obtain a racemic form (1.4 g, 1.5 mmol) of dichlorosilacyclobutylenebis[2-(5-methyl-2-furyl)-4-(4-tert-butylphenyl)-5,6-dimethyl-1-indenyl]zirconium as an orange crystal with 11% yield.

$^1$H-NMR (400 MHz, $C_6D_6$) δ 1.18 (s, 18H), 1.92 (s, 6H), 2.12 (s, 6H), 2.16 (s, 6H), 2.21-2.28 (m, 2H), 2.64-2.75 (m, 4H), 5.66 (dd, 2H), 6.06 (d, 2H), 6.79 (s, 2H), 6.95 (s, 2H), 7.22 (dd, 2H), 7.37 (dd, 2H), 7.44 (dd, 2H), 8.28 (dd, 2H).

(7-6) Preparation of Catalyst Using Metallocene Complex G (Catalyst G)

33.5 g of a solid catalyst (Catalyst G) was obtained by the same operation as in Example 1 (1-7) except that 290 mg (310 μmol) of Metallocene Complex G was used in place of Metallocene Complex A.

The prepolymerization magnification (a value obtained by dividing the amount of prepolymerized polymer by the amount of solid catalyst) was 2.23.

(7-7) Propylene-Propylene.Ethylene Two-Stage Polymerization by Catalyst G

The operation was performed in the same manner as in Example 1 (1-8) except that the amount of the catalyst used was 16 mg, 300 mL of hydrogen was used in the first step, the average gas molar composition in the reactor during the propylene/ethylene polymerization was adjusted to propylene/ethylene=48/52 in the seconds step, and the polymerization time was 25 minutes in the second step. As a result, 240 g of a propylene-propylene.ethylene block copolymer was obtained.

In the block copolymer obtained above, from the results of CFC-IR, the rubber content (CP content) was 26 wt %, the ethylene content in rubber (CP) was 42 mol %, and the weight average molecular weight (Mw) of the CP moiety was 622,000. The rubber polymerization activity (CP activity) was 12,700 (g-CP/g-Cat/hr).

Tm of 67 g of the propylene polymer component (PP) separately collected in the first step was 160° C., MFR was 3.9 (dg/min), and the PP polymerization activity was 15,400 (g-PP/g-Cat/hr).

The results are shown together in Table 1.

Example 8

Metallocene Complex H

Synthesis of dichlorosilacyclobutylenebis[2-(5-methyl-2-furyl)-4-phenyl-1,5,6,7-tetrahydro-5,5,7,7-tetra methyl-s-indacen-1-yl]zirconium (8-1) Synthesis of 5,5,7,7-tetramethyl-3,5,6,7-tetrahydro-2H-s-indacen-1-one A mixed solution of 1,1,3,3-tetramethylindane (34.3 g) and 3-chloropropionyl chloride (25 g) was added dropwise, on an ice bath, to a nitromethane (150 mL) solution of aluminum chloride (32 g). The temperature was raised to room temperature and after stirring for 5 hours, the reaction solution was poured in 1 N hydrochloric acid-ice water, followed by stirring. The organic layer was separated, washed with 1 N hydrochloric acid, water and saturated brine, and then dried over magnesium sulfate. The solvent was removed by distillation under reduced pressure, and sulfuric acid (150 mL) was added thereto, followed by stirring under heating at 80° C. for 3 hours. After the completion of reaction, the reaction solution was poured in ice water and extracted with diethyl ether, and the organic layer was washed with water and saturated brine and then dried over magnesium sulfate. The solvent was removed by distillation under reduced pressure to obtain 27.5 g of a crude product of 5,5,7,7-tetramethyl-3,5,6,7-tetrahydro-2H-s-indacen-1-one.

$^1$H-NMR (400 MHz, $CDCl_3$) δ 1.33 (s, 6H), 1.35 (s, 6H), 1.97 (s, 2H), 2.69 (t, 2H), 3.10 (t, 2H), 7.19 (s, 1H), 7.53 (s, 1H).

(8-2) Synthesis of 1,1,3,3-tetramethyl-4-bromo-1,2,3,5-tetrahydro-s-indacene

The crude product (27.5 g) of 5,5,7,7-tetramethyl-3,5,6,7-tetrahydro-2H-s-indacen-1-one was added to a suspension solution of aluminum chloride (37 g) and chloroform (150 mL) and after stirring for 0.5 hours, a chloroform solution (20 mL) of bromine (6.2 mL) was added dropwise under cooling on an ice bath and reacted for 4 hours at room temperature. After the completion of reaction, the reaction solution was poured in 1 N hydrochloric acid-ice water, followed by stirring. The organic layer was liquid-separated, washed with 1 N hydrochloride acid, water and saturated brine, and then dried over magnesium sulfate. The solvent was removed by distillation under reduced pressure, and the residue was purified by recrystallization from diethyl ether and hexane to obtain a yellow solid (18 g). The obtained solid was suspended in methanol (120 mL), and sodium borohydride (2.2 g) was added under cooling on an ice bath, followed by stirring for 2 hours at room temperature. After the reaction, about half of the solvent was removed by distillation under reduced pressure, and the residue was quenched by the addition of 1 N hydrochloric acid and then extracted with diethyl ether. The organic layer was washed successively with 1 N hydrochloric acid, water and saturated brine and dried over magnesium sulfate, and the solvent was removed by distillation under reduced pressure. Furthermore, a toluene (150 mL) solution of the obtained yellow solid (18 g) and p-toluenesulfonic acid (0.1 g) was heated under reflux. After one hour, the organic layer was separated by adding water, washed with saturated brine, and then dried over magnesium sulfate. The solvent was removed by distillation, and the obtained crude product was purified by silica gel column chromatography to obtain 1,1,3,3-tetramethyl-4-bromo-1,2,3,5-tetrahydro-s-indacene (15 g).

$^1$H-NMR (400 MHz, CDCl$_3$) δ 1.31 (s, 6H), 1.52 (s, 6H), 1.99 (s, 2H), 3.36 (s, 2H), 6.54 (d, 1H), 6.86 (d, 1H), 7.10 (s, 1H).

(8-3) Synthesis of 1,1,3,3-tetramethyl-4-phenyl-1,2,3,5-tetrahydro-s-indacene

Phenylboronic acid (3.2 g, 26 mmol) was dissolved in dimethoxyethane (80 mL), and an aqueous solution (30 mL) of cesium carbonate (11.3 g), 1,1,3,3-tetramethyl-4-bromo-1,2,3,5-tetrahydro-s-indacene (5.06 g, 17.4 mmol), and tetrakis(triphenylphosphine)palladium (0.8 g) were sequentially added. After allowing the reaction to proceed for 13 hours by heating under reflux, the reaction solution was poured in 1 N hydrochloric acid-ice water, followed by stirring, and extracted with diethyl ether. The organic layer was washed with saturated brine and dried over magnesium sulfate, and the solvent was then removed by distillation under reduced pressure to obtain a crude product. The crude produce was purified by silica gel column chromatography to obtain the target 1,1,3,3-tetramethyl-4-phenyl-1,2,3,5-tetrahydro-s-indacene (3.8 g, yield: 77%).

(8-4) Synthesis of 1,1,3,3-tetramethyl-4-phenyl-6-(5-methyl-2-furyl)-1,2,3,5-tetrahydro-s-indacene The obtained 1,1,3,3-tetramethyl-4-phenyl-1,2,3,5-tetrahydro-s-indacene (3.8 g, 13.2 mmol) was dissolved in dimethylsulfoxide (100 mL), and water (4 mL) was added. N-Bromosuccinimide (3 g) was added thereto at 0° C., followed by stirring day and night at room temperature, and the resulting solution was quenched by the addition of water on an ice bath. The organic layer was extracted by adding toluene, and p-toluenesulfonic acid monohydrate (0.1 g) was added to the organic layer and reacted by heating under reflux for one hour. Thereafter, water was added to the reaction solution, and the organic layer was separated. The obtained organic layer was washed with saturated brine and dried over magnesium sulfate, and the solvent was then removed by distillation under reduced pressure to obtain a crude product.

On the other hand, 2-methylfuran (1.8 mL, 19.8 mmol) was dissolved in dimethoxyethane (50 mL), and an n-hexane solution (1.64 M, 12.1 mL) of n-butyllithium was added dropwise under ice cooling, followed by stirring for one hour. Thereafter, while continuing cooling on an ice bath, trimethyl borate (2.5 mL, 22 mmol) was added dropwise, and the resulting solution was stirred for 16 hours at room temperature. Water (10 mL) was added and after stirring for one hour, the solvent was removed by distillation under reduced pressure. Thereto, an aqueous solution (30 mL) of sodium carbonate (2.8 g, 26.4 mmol), a dimethoxyethane (25 mL) solution of the crude product synthesized above, and tetrakis(triphenylphosphine)palladium (0.38 g) were sequentially added and reacted by heating under reflux for 3 hours. Water was added to the reaction solution, and the organic layer was separated, washed with saturated brine, and dried over magnesium sulfate. The solvent was then removed by distillation under reduced pressure, and the obtained crude produce was purified by silica gel column chromatography to obtain the target 1,1,3,3-tetramethyl-4-phenyl-6-(5-methyl-2-furyl)-1,2,3,5-tetrahydro-s-indacene (2.25 g).

(8-5) Synthesis of 1,1-bis[2-(5-methyl-2-furyl)-4-phenyl-5,5,7,7-tetramethyl-1,5,6,7-tetrahydro-s-indacenyl]silacyclobutane 1,1,3,3-Tetramethyl-4-phenyl-6-(5-methyl-2-furyl)-1,2,3,5-tetrahydro-s-indacene (3.7 g, 10 mmol) was dissolved in tetrahydrofuran (60 mL), and an n-hexane solution (1.65 M, 6.1 mL) of n-butyllithium was added dropwise at −70° C. After stirring for 3 hours while slowly raising the temperature, N-methylimidazole (0.02 mL) and 1,1-dichlorosilacyclobutane (0.59 mL, 5.0 mmol) were added dropwise at −70° C. The temperature was raised to room temperature and after stirring for 1.5 hours, the organic layer was separated by adding water and dried over magnesium sulfate. The solvent was then removed by distillation under reduced pressure to obtain a crude product (4.3 g) of 1,1-bis[2-(5-methyl-2-furyl)-4-phenyl-5,5,7,7-tetramethyl-1,5,6,7-tetrahydro-s-indacenyl]silacyclobutane.

(8-6) Synthesis of dichlorosilacyclobutylenebis[2-(5-methyl-2-furyl)-4-phenyl-1,5,6,7-tetrahydro-5,5,7,7-tetra methyl-s-indacen-1-yl]zirconium (Metallocene H)

The synthesized crude product (4.3 g) of 1,1-bis[2-(5-methyl-2-furyl)-4-phenyl-5,5,7,7-tetramethyl-1,5,6,7-tetrahydro-s-indacenyl]silacyclobutane was suspended in diethyl ether (50 mL) and toluene (10 mL), and an n-hexane solution (1.65 M, 6.1 mL) of n-butyllithium was added dropwise on an ice bath. After stirring for 2 hours at room temperature, the solvent was removed by distillation under reduced pressure. Methylene chloride (50 mL) was added and dissolved, and zirconium tetrachloride (1.16 g) was added at −72° C., followed by stirring for 2 hours at room temperature. The obtained reaction solution was once concentrated, washed with toluene, and extracted with methylene chloride. The solution was further washed with toluene and n-hexane to obtain 1.3 g of a racemic form of dichlorosilacyclobutylenebis[2-(5-methyl-2-furyl)-4-phenyl-1,5,6,7-tetrahydro-5,5,7,7-tetra methyl-s-indacen-1-yl]zirconium.

$^1$H-NMR (400 MHz, CDCl$_3$) δ 0.84 (s, 6H, Me$_4$), 0.93 (s, 6H, Me$_4$), 1.16 (s, 6H, Me$_4$), 1.19 (s, 6H, Me$_4$), 1.71 (q, 4H, —CH$_2$—), 2.2-2.8 (m, 6H, Si(CH$_2$)$_3$), 2.43 (s, 6H, Furyl-CH$_3$), 5.95 (dd, J=1.0 Hz, 3.2 Hz, 2H, Furyl-H), 6.25 (d, J=3.3 Hz, 2H, Furyl-H), 6.24 (s, 2H, Cp), 6.73 (s, 2H, arm), 7.1-7.2 (m, 2H, arm), 7.2-7.3 (m, 4H, arm), 7.3-7.5 (m, 2H, arm), 7.6-7.8 (m, 2H, arm.).

(8-7) Preparation of Catalyst Using Metallocene Complex H (Catalyst H)

32.5 g of a solid catalyst (Catalyst H) was obtained by the same operation as in Example 1 (1-7) except that 300 mg (310 μmol) of Metallocene Complex H was used in place of Metallocene Complex A.

The prepolymerization magnification (a value obtained by dividing the amount of prepolymerized polymer by the amount of solid catalyst) was 2.14.

(8-8) Propylene-Propylene.Ethylene Two-Stage Polymerization by Catalyst H

The operation was performed in the same manner as in Example 1 (1-8) except that the amount of the catalyst used was 30 mg, 540 mL of hydrogen was used in the first step, the average gas molar composition in the reactor during the propylene/ethylene polymerization was adjusted to propylene/ethylene=56/44 in the seconds step, and the polymerization time was 15 minutes in the second step. As a result, 99.6 g of a propylene-propylene.ethylene block copolymer was obtained.

In the block copolymer obtained above, from the results of CFC-IR, the rubber content (CP content) was 61 wt %, the ethylene content in rubber (CP) was 35 mol %, and the weight average molecular weight (Mw) of the CP moiety was 447,000. The rubber polymerization activity (CP activity) was 10,000 (g-CP/g-Cat/hr).

Tm of the propylene polymer component (PP) separately collected in the first step was 158° C., MFR was 7.0 (dg/min), and the PP polymerization activity was 1,600 (g-PP/g-Cat/hr).

The results are shown together in Table 1.

Example 9

Metallocene Complex I

Synthesis of dichlorosilacyclobutylenebis[2-(5-methyl-2-furyl)-4-(2,6-dimethyl-4-biphenylyl)-5,6-dimethyl-1-indenyl]zirconium (9-1) Synthesis of 4-(2,6-dimethyl-4-biphenylyl)-5,6-dimethylindene 2,6-Dimethyl-4-bromobiphenyl (11 g) was dissolved in diethyl ether and after cooling to −78° C., an n-pentane solution (1.65 M, 51 mL) of tert-butyllithium was added dropwise, followed by stirring for 2 hours. Thereafter, triisopropyl borate (11 mL) was added dropwise, and the resulting solution was stirred for 16 hours at room temperature. Water (10 mL) was added, followed by stirring for one hour, and the solvent was removed by distillation under reduced pressure. Thereto, 4-bromo-5,6-dimethylindene (8.5 g, 38 mmol), cesium carbonate (25 g), tetrakis(triphenylphosphine)palladium (0.88 g), dimethoxyethane (90 mL), and water (30 mL) were sequentially added. After allowing the reaction to proceed for 2 hours by heating under reflux, the reaction solution was quenched with 1 N hydrochloric acid and extracted with diethyl ether. The organic layer was washed with saturated brine and dried over magnesium sulfate and after removing the solvent by distillation under reduced pressure, the residue was filtered on silica gel to obtain a crude product (11.8 g) of 4-(2,6-dimethyl-4-biphenylyl)-5,6-dimethylindene.

(9-2) Synthesis of 2-bromo-4-(2,6-dimethyl-4-biphenylyl)-5,6-dimethylindene

The crude product (11.8 g, 36 mmol) of 4-(2,6-dimethyl-4-biphenylyl)-5,6-dimethylindene was dissolved in dimethyl sulfoxide (150 mL), and water (4 mL) was added. N-Bromosuccinimide (8.6 g, 48 mmol) was added thereto on an ice bath, followed by stirring for 4 hours at room temperature, and the resulting solution was quenched by the addition of water on an ice bath. The organic layer was extracted by adding toluene, and p-toluenesulfonic acid monohydrate (0.25 g) was added to the organic layer and reacted by heating under reflux for 2 hours. Thereafter, water was added to the reaction solution, and the organic layer was separated. The obtained organic layer was washed with saturated brine and dried over magnesium sulfate and after removing the solvent by distillation under reduced pressure, the residue was filtered on silica gel to obtain a crude product (11 g).

(9-3) Synthesis of 2-(5-methyl-2-furyl)-4-(2,6-dimethyl-4-biphenylyl)-5,6-dimethylindene 2-Methylfuran (3.7 mL, 41 mmol) was dissolved in dimethoxyethane (130 mL), and an n-hexane solution (1.6 M, 25.6 mL) of n-butyllithium was added dropwise under cooling on an ice bath, followed by stirring for 2 hours. Thereafter, while continuing cooling on an ice bath, trimethyl borate (5.1 mL, 45 mmol) was added dropwise, and the resulting solution was stirred for 16 hours at room temperature. Water (5 mL) was added and after stirring for one hour, the solvent was removed by distillation under reduced pressure. Thereto, sodium carbonate (5.8 g), the crude product (11 g) synthesized above of 2-bromo-4-(2,6-dimethyl-4-biphenylyl)-5,6-dimethylindene, tetrakis(triphenylphosphine)palladium (0.8 g), DME (100 mL), and water (40 mL) were sequentially added and reacted by heating under reflux for 2 hours. The reaction solution was quenched with 1 N hydrochloric acid, and the organic layer was then separated, washed with 1 N hydrochloric acid and saturated brine, and dried over magnesium sulfate. The solvent was removed by distillation under reduced pressure, and the residue was purified by silica gel column chromatography to obtain the target 2-(5-methyl-2-furyl)-4-(2,6-dimethyl-4-biphenylyl)-5,6-dimethylindene (5 g).

(9-4) Synthesis of 1,1-bis[2-(5-methyl-2-furyl)-4-(2,6-dimethyl-4-biphenylyl)-5,6-dimethylindene]silacyclobutane 2-(5-Methyl-2-furyl)-4-(2,6-dimethyl-4-biphenylyl)-5,6-dimethylindene (3.0 g, 7.4 mmol) was dissolved in tetrahydrofuran (60 mL), and an n-hexane solution (1.55 M, 4.8 mL) of n-butyllithium was added dropwise at −78° C. After stirring for 3 hours, N-methylimidazole (0.03 mL) and 1,1-dichlorosilacyclobutane (0.44 mL, 3.7 mmol) were added dropwise, and the resulting solution was stirred for 2 hours while gradually raising the temperature to room temperature. The organic layer was separated by adding water and dried over magnesium sulfate and after removing the solvent by distillation under reduced pressure, the obtained solid was washed with hexane to obtain 1,1-bis[2-(5-methyl-2-furyl)-4-(2,6-dimethyl-4-biphenylyl)-5,6-dimethylindenyl]silacyclobutane (2.5 g).

(9-5) Synthesis of dichlorosilacyclobutylenebis[2-(5-methyl-2-furyl)-4-(2,6-dimethyl-4-biphenylyl)-5,6-dimethyl-1-indenyl]zirconium (Metallocene Complex I)

1,1-Bis[2-(5-methyl-2-furyl)-4-(2,6-dimethyl-4-biphenylyl)-5,6-dimethylindenyl]silacyclobutane (2.5 g) was suspended in diethyl ether (40 mL), and an n-hexane solution (1.55 M, 3.7 mL) of n-butyllithium was added dropwise on an ice bath. After stirring for 3 hours while gradually raising the temperature to room temperature, the obtained reaction solution was once concentrated, dichloromethane (40 mL) was added, and zirconium tetrachloride (0.7 g) was added at −50° C. After stirring for 2.5 hours while gradually raising the temperature to room temperature, the obtained reaction solution was once concentrated, washed with n-hexane, diethyl ether and toluene, and extracted with dichloromethane. Subsequently, recrystallization from toluene was performed to obtain 0.5 g of a racemic form of dichlorosilacyclobutylenebis[2-(5-methyl-2-furyl)-4-(2,6-dimethyl-4-biphenylyl)-5,6-dimethyl-1-indenyl]zirconium.

$^1$H-NMR (400 MHz, C$_6$D$_6$) δ 1.97 (s, 6H), 2.01 (s, 6H), 2.05 (s, 6H), 2.23 (s, 6H), 2.52 (s, 6H), 2.2-2.3 (m, 2H), 2.55-2.65 (m, 2H), 2.79-2.85 (m, 2H), 6.01 (d, J=2.3 Hz, 2H), 6.29 (d, J=3.3 Hz, 2H), 6.56 (s, 2H), 6.61 (s, 2H), 6.89 (s, 2H), 7.1-7.2 (m, 2H), 7.3-7.5 (m, 10H).

(9-6) Preparation of Catalyst Using Metallocene Complex I (Catalyst I)

31.9 g of a solid catalyst (Catalyst I) was obtained by the same operation as in Example 1 (1-7) except that 290 mg (279 μmol) of Metallocene Complex I was used in place of Metallocene Complex A.

The prepolymerization magnification (a value obtained by dividing the amount of prepolymerized polymer by the amount of solid catalyst) was 2.09.

(9-7) Propylene-Propylene.Ethylene Two-Stage Polymerization by Catalyst I

The operation was performed in the same manner as in Example 1 (1-8) except that the amount of the catalyst used was 15 mg, 297 mL of hydrogen was used in the first step, the average gas molar composition in the reactor during the propylene/ethylene polymerization was adjusted to propylene/ethylene=47/53 in the seconds step, and the polymerization time was 60 minutes in the second step. As a result, 137.0 g of a propylene-propylene.ethylene block copolymer was obtained.

In the block copolymer obtained above, from the results of CFC-IR, the rubber content (CP content) was 43 wt %, the ethylene content in rubber (CP) was 41 mol %, and the weight average molecular weight (Mw) of the CP moiety was 765,000. The rubber polymerization activity (CP activity) was 5,600 (g-CP/g-Cat/hr).

Tm of the propylene polymer component (PP) separately collected in the first step was 162° C., MFR was 0.9 (dg/min), and the PP polymerization activity was 7,300 (g-PP/g-Cat/hr).

The results are shown together in Table 1.

Example 10

Metallocene Complex J

Synthesis of dichlorosilacyclobutylenebis[2-(4,5-dimethyl-2-furyl)-4-(4-tert-butyl-phenyl)-5,6-dimethyl-1-indenyl]zirconium (10-1) Synthesis of 2-(4,5-dimethyl-2-furyl)-4-(4-tert-butyl-phenyl)-5,6-dimethylindene 2,3-Dimethylfuran (1.0 g, 10 mmol) was dissolved in dimethoxyethane (20 mL), and an n-hexane solution (1.65 M, 6.3 mL) of n-butyllithium was added dropwise, followed by stirring for 2 hours. Subsequently, trimethyl borate (1.5 mL, 13 mmol) was added dropwise and after raising the temperature to room temperature, the resulting solution was stirred for 16 hours. Water (5 mL) was added, followed by stirring for one hour, and the solvent was removed by distillation under reduced pressure. Thereto, an aqueous solution (15 mL) of sodium carbonate (1.5 g), a crude product (2.5 g) of 2-bromo-4-(4-tert-butyl-phenyl)-5,6-dimethylindene, tetrakis(triphenylphosphine)palladium (0.2 g), and DME (30 mL) were sequentially added and reacted for one hour by heating under reflux. After adding 1 N hydrochloric acid to the reaction solution, the organic layer was separated, washed with 1 N hydrochloric acid and saturated brine, and dried over magnesium sulfate. Thereafter, the solvent was removed by distillation under reduced pressure, and the residue was purified by silica gel chromatography to obtain the target 2-(4,5-dimethyl-2-furyl)-4-(4-tert-butyl-phenyl)-5,6-dimethylindene (1.9 g).

(10-2) Synthesis of dichlorosilacyclobutylenebis[2-(4,5-methyl-2-furyl)-4-(4-tert-butyl-phenyl)-5,6-dimethyl-1-indenyl]zirconium (Metallocene Complex J)

2-(4,5-Dimethyl-2-furyl)-4-(4-tert-butyl-phenyl)-5,6-dimethylindene (1.9 g, 5.1 mmol) was suspended in tetrahydrofuran (30 mL), and an n-hexane solution (1.63 M, 3.1 mL) of n-butyllithium was added dropwise at −78° C. After stirring for 3 hours, N-methylimidazole (0.03 mL) and 1,1-dichlorosilacyclobutane (0.3 mL, 2.5 mmol) were added dropwise at −78° C., and the resulting solution was stirred for 2 hours while gradually raising the temperature to room temperature. The organic layer was separated by adding water and dried over magnesium sulfate, and the solvent was then removed by distillation under reduced pressure. The obtained crude product (1.9 g) of 1,1-bis[2-(4,5-dimethyl-2-furyl)-4-(4-tert-butyl-phenyl)-5,6-dimethylindenyl]silacyclobutane was dissolved in diethyl ether (35 mL), and an n-hexane solution (1.63 M, 3.1 mL) of n-butyllithium was added dropwise on an ice bath. After stirring for 2 hours while gradually raising the temperature to room temperature, the obtained reaction solution was once concentrated, dichloromethane (35 mL) was added, and zirconium tetrachloride (0.6 g) was added at −40° C. After stirring for 2 hours while gradually raising the temperature to room temperature, the obtained reaction solution was once concentrated, then extracted with toluene, washed with hexane, and extracted with a toluene-hexane mixed solution. Subsequently, washing with diethyl ether was performed to obtain 0.3 g of a racemic form of dichlorosilacyclobutylenebis[2-(4,5-dimethyl-2-furyl)-4-(4-tert-butyl-phenyl)-5,6-dimethyl-1-indenyl]zirconium.

$^1$H-NMR (400 MHz, C$_6$D$_6$) δ 1.35 (s, 18H), 1.88 (s, 6H), 1.90 (s, 6H), 2.13 (s, 6H), 2.41 (s, 6H), 2.1-2.3 (m, 2H), 2.5-2.8 (m, 4H), 6.13 (s, 2H), 6.42 (s, 2H), 6.52 (s, 2H), 7.0-7.1 (m, 2H), 7.3-7.7 (m, 6H).

(10-3) Preparation of Catalyst Using Metallocene Complex J (Catalyst J)

30.7 g of a solid catalyst (Catalyst J) was obtained by the same operation as in Example 1 (1-7) except that 293 mg (302 μmol) of Metallocene Complex J was used in place of Metallocene Complex A.

The prepolymerization magnification (a value obtained by dividing the amount of prepolymerized polymer by the amount of solid catalyst) was 1.92.

(10-4) Propylene-Propylene.Ethylene Two-Stage Polymerization by Catalyst J

The operation was performed in the same manner as in Example 1 (1-8) except that the amount of the catalyst used was 15 mg, 297 mL of hydrogen was used in the first step, the average gas molar composition in the reactor during the propylene/ethylene polymerization was adjusted to propylene/ethylene=49/51 in the seconds step, and the polymerization time was 60 minutes in the second step. As a result, 179.9 g of a propylene-propylene.ethylene block copolymer was obtained.

In the block copolymer obtained above, from the results of CFC-IR, the rubber content (CP content) was 38 wt %, the ethylene content in rubber (CP) was 46 mol %, and the weight average molecular weight (Mw) of the CP moiety was 777,000. The rubber polymerization activity (CP activity) was 5,800 (g-CP/g-Cat/hr).

Tm of the propylene polymer component (PP) separately collected in the first step was 161° C., MFR was 60 (dg/min), and the PP polymerization activity was 9,300 (g-PP/g-Cat/hr).

The results are shown together in Table 1.

Example 11

(11-1) Preparation of Methylaluminoxane-Supported Silica

In a nitrogen atmosphere, 30 g of silica (particle diameter: 45 μm) for supported catalyst, which was fired at 400° C. for 5 hours, was put in a 1 L three-neck flask and dried under reduced pressure for one hour by means of a vacuum pump while heating it on an oil bath at 150° C. 200 mL of dehydrated toluene and 83 mL of a 20% methylaluminoxane/toluene solution produced by Albemarle Corp. were added at room temperature, followed by stirring for one hour at 40° C., and the toluene solvent was removed by distillation under reduced pressure while keeping heating at 40° C. to obtain 46.7 g of methylaluminoxane-supported silica.

(11-2) Preparation of Catalyst Using Metallocene Complex G (Catalyst K)

In a nitrogen atmosphere, 15.5 g of the methylaluminoxane-supported silica was put in a 1 L three-neck flask, and 50 mL of heptane and a heptane solution (3.3 mL) of triisobutylaluminum were added, followed by stirring for 10 minutes at room temperature. Furthermore, a toluene (30 mL) solution of Metallocene Complex G (283 mg, 300 μmol) was added, followed by stirring for 60 minutes at room temperature.

Next, heptane (217 mL) was added to the heptane slurry above and after introducing it into a stirring-type autoclave with an inner volume of 1 L, propylene was fed at 40° C. for 120 minutes at a constant rate of 10 g/hour.

After the completion of propylene feeding, the system was maintained as it is for 30 minutes. The residual gas was then purged, and a prepolymerization catalyst slurry was recovered from the autoclave. The recovered prepolymerization catalyst slurry was left standing still, and the supernatant liquid was extracted. A heptane solution (8.5 mL, 6.1 mmol) of triisobutylaluminum was added at room temperature to the remaining solid and after stirring for 10 minutes at room temperature, the slurry was dried under reduced pressure at 40° C. to recover 28.9 g of a solid catalyst (Catalyst K). The prepolymerization magnification (a value obtained by dividing the amount of prepolymerized polymer by the amount of solid catalyst) was 1.83.

(11-3) Propylene-Propylene.Ethylene Two-Stage Polymerization by Catalyst K

The operation was performed in the same manner as in Example 1 (1-8) except that the amount of the catalyst used was 10 mg, 800 mL of hydrogen was used in the first step, and the average gas molar composition in the reactor during the propylene/ethylene polymerization was adjusted to propylene/ethylene=50/50. As a result, 328 g of a propylene-propylene.ethylene block copolymer was obtained.

In the block copolymer obtained above, from the results of CFC-IR, the rubber content (CP content) was 21 wt %, the ethylene content in rubber (CP) was 39 mol %, and the weight average molecular weight (Mw) of the CP moiety was 602,000. The rubber polymerization activity (CP activity) was 14,500 (g-CP/g-Cat/hr).

Tm of the propylene polymer component (PP) separately collected in the first step was 159° C., MFR was 120 (dg/min), and the PP polymerization activity was 28,100 (g-PP/g-Cat/hr).

The results are shown together in Table 1.

Example 12

(12-1) Propylene Polymerization by Catalyst A

After the inside of a stirring-type autoclave with an inner volume of 3 L was sufficiently replaced by a propylene gas, an n-heptane solution (2.76 mL, 2.02 mmol) of triisobutylaluminum was added, and hydrogen (310 mL) and subsequently liquid propylene (750 g) were introduced. The temperature was raised to 65° C., and this temperature was maintained. Catalyst A was slurried in n-heptane and injected as a catalyst in an amount of 34 mg (excluding the weight of prepolymerized polymer) under pressure to start polymerization, and the temperature inside the reactor was maintained at 65° C. After the elapse of one hour from the injection of catalyst, ethanol was injected under pressure to purge the residual monomer, and PP was recovered. As a result, 292 g of a propylene polymer was obtained.

In the PP obtained, the activity was 8,600 (g-PP/g-Cat/hr), MFR was 7.3 (dg/min), the weight average molecular weight (Mw) was 250,000, and Tm was 161° C.

The results are shown together in Table 2.

Examples 13 to 22

Propylene Polymerization by Catalysts B to K

The operation was performed in the same manner as in Example 12 (12-1) by changing the catalyst to Catalysts B to K, respectively.

The results are shown together in Table 2.

Comparative Example 1

(Compar. 1-1) Metallocene Complex W

Synthesis of dichlorodimethylsilylenebis[2-(5-methyl-2-furyl)-4-phenyl-1,5,6,7-tetrahydro-s-indacen-1-yl]zirconium Metallocene Complex W was synthesized by referring to the method described in Example 1 of JP-A-2012-121882, and a racemic form was obtained.

(Compar. 1-2) Preparation of Catalyst Using Metallocene Complex W (Catalyst W)

7.3 g of a solid catalyst (Catalyst W) was obtained by the same operation as in Example 1 (1-7) except that 63 mg (75 μmol) of Metallocene Complex W was used in place of Metallocene Complex A.

The prepolymerization magnification (a value obtained by dividing the amount of prepolymerized polymer by the amount of solid catalyst) was 0.44.

(Compar. 1-3) Propylene-Propylene.Ethylene Two-Stage Polymerization by Catalyst W The operation was performed in the same manner as in Example 1 (1-8) except that the amount of the catalyst was 50 mg and the average gas molar composition in the reactor during the propylene/ethylene polymerization was adjusted to propylene/ethylene=41/59. As a result, 105 g of a propylene-propylene.ethylene block copolymer was obtained.

In the block copolymer obtained above, from the results of CFC-IR, the rubber content (CP content) was 17 wt %, the ethylene content in rubber (CP) was 52 mol %, and the weight average molecular weight (Mw) of the CP moiety was 513,000. The rubber polymerization activity (CP activity) was 730 (g-CP/g-Cat/hr).

Tm of the propylene polymer component (PP) separately collected in the first step was 160° C., MFR was 16 (g/10 min), and the PP polymerization activity was 2,200 (g-PP/g-Cat/hr).

The results are shown together in Table 1.

Comparative Example 2

Metallocene Complex X

Synthesis of dichlorodimethylsilylenebis[2-(5-methyl-2-furyl)-4-phenyl-5,6-dimethyl-1-indenyl] zirconium (Compar. 2-1) Synthesis of dimethylbis[2-(5-methyl-2-furyl)-4-phenyl-5,6-dimethyl-1-indenyl] silane 2-(5-Methyl-2-furyl)-4-phenyl-5,6-dimethylindene (2.4 g, 8.0 mmol) was dissolved in diethyl ether (30 mL) and toluene (40 mL), and an n-hexane solution (1.59 M, 5.0 mL) of n-butyllithium was added dropwise at −40° C. The temperature was raised to room temperature and after stirring for 3 hours, N-methylimidazole (0.02 mL) and dichlorodimethylsilane (0.49 mL, 4.0 mmol) were added dropwise at −30° C. The temperature was raised to room temperature and after stirring for 1.5 hours, the organic layer was separated by adding water and dried over magnesium sulfate. Thereafter, the solvent was removed by distillation under reduced pressure to obtain a crude product (2.6 g) of dimethylbis{2-(5-methyl-2-furyl)-4-phenyl-5,6-dimethylindenyl}silane.

(Compar. 2-2) Synthesis of dichlorodimethylsilylenebis[2-(5-methyl-2-furyl)-4-phenyl-5,6-dimethyl-1-indenyl]zirconium (Metallocene Complex X)

The synthesized crude product (2.6 g) of dimethylbis {2-(5-methyl-2-furyl)-4-phenyl-5,6-dimethylindenyl}silane was dissolved in diethyl ether (30 mL) and toluene (50 mL), and an n-hexane solution (1.59 M, 5.0 mL) of n-butyllithium was added dropwise on an ice bath. After stirring for 3 hours at room temperature, the solvent was removed by distillation under reduced pressure. The residue was washed with hexane (40 mL) three times and a solid obtained by removing the solvent by distillation under reduced pressure was added to a methylene chloride (40 mL) suspension solution of zirconium tetrachloride (0.9 g) at −72° C. After stirring for 2 hours and stirring for 4 hours at room temperature, the obtained reaction solution was once concentrated, extracted with toluene, extracted with n-hexane, and washed successively with n-hexane, diisopropyl ether and toluene.

The methylene chloride-hexane recrystallization was further repeated to obtain 0.3 g of a racemic form of dichlorodimethylsilylenebis[2-(5-methyl-2-furyl)-4-phenyl-5,6-dimethyl-1-indenyl]zirconium.

$^1$H-NMR (400 MHz, CDCl$_3$) δ 1.09 (s, 6H, Si(CH$_3$)$_2$), 2.05 (s, 6H, tol-CH$_3$), 2.14 (s, 6H, tol-CH$_3$), 2.41 (s, 6H, Furyl-CH$_3$), 6.02 (dd, J=1.0 Hz, 3.3 Hz, 2H, Furyl-H), 6.16 (d, J=3.3 Hz, 2H, Furyl-H), 6.44 (s, 2H, Cp), 6.67 (s, 2H, arm), 7.09-7.12 (m, 2H, arm), 7.28-7.37 (m, 2H, arm), 7.43-7.50 (m, 2H, arm), 7.67-7.72 (m, 2H, arm.).

(Compar. 2-3) Preparation of Catalyst Using Metallocene Complex X (Catalyst X)

13.4 g of a solid catalyst (Catalyst X) was obtained by the same operation as in Example 1 (1-7) except that chemically treated montmorillonite (5.0 g) and 122 mg (150 μmol) of Metallocene Complex X in place of Metallocene Complex A were used.

The prepolymerization magnification (a value obtained by dividing the amount of prepolymerized polymer by the amount of solid catalyst) was 1.64.

(Compar. 2-4) Propylene-Propylene.Ethylene Two-Stage Polymerization by Catalyst X The operation was performed in the same manner as in Example 1 (1-8) except that the amount of the catalyst was 50 mg, 200 mL of hydrogen was used in the first step, the average gas molar composition in the reactor during the propylene/ethylene polymerization was adjusted to propylene/ethylene=59/41 in the seconds step, and the polymerization time was 30 minutes in the second step. As a result, 99.8 g of a propylene-propylene.ethylene block copolymer was obtained.

In the block copolymer obtained above, from the results of CFC-IR, the rubber content (CP content) was 14 wt %, the ethylene content in rubber (CP) was 32 mol %, and the weight average molecular weight (Mw) of the CP moiety was 730,000. The rubber polymerization activity (CP activity) was 570 (g-CP/g-Cat/hr).

Tm of the propylene polymer component (PP) separately collected in the first step was 159° C., MFR was 16 (dg/min), and the PP polymerization activity was 2,100 (g-PP/g-Cat/hr).

The results are shown together in Table 1.

Comparative Example 3

Synthesis of Metallocene Complex Y:

Synthesis of dichlorodimethylsilylenebis[2-(5-methyl-2-furyl)-4-phenyl-1,5,6,7-tetrahydro-5,5,7,7-tetramethyl-s-indacen-1-yl]zirconium (Compar. 3-1) Synthesis of dichlorodimethylsilylenebis[2-(5-methyl-2-furyl)-4-phenyl-1,5,6,7-tetrahydro-5,5,7,7-tetramethyl-s-indacenyl]zirconium 1,1,3,3-Tetramethyl-4-phenyl-6-(5-methyl-2-furyl)-1,2,3,5-tetrahydro-s-indacene (2.25 g, 6.1 mmol) was dissolved in diethyl ether (40 mL), and an n-hexane solution (1.64 M, 3.7 mL) of n-butyllithium was added dropwise at −20° C. After stirring for 2 hours at room temperature, N-methylimidazole (0.02 mL) and dichlorodimethylsilane (0.37 mL, 3.1 mmol) were added dropwise at −20° C. After stirring for 1.5 hours at room temperature, the organic layer was separated by adding water and dried over magnesium sulfate. Thereafter, the solvent was removed by distillation under reduced pressure to obtain a crude product (2.6 g) of dimethylbis[2-(5-methyl-2-furyl)-4-phenyl-5,5,7,7-tetramethyl-1,5,6,7-tetrahydro-s-indacenyl]silane. The crude product was dissolved in diethyl ether (40 mL), and an n-hexane solution (1.64 M, 3.7 mL) of n-butyllithium was added dropwise on an ice bath. After stirring for 2 hours at room temperature, the solvent was removed by distillation under reduced pressure.

Diethyl ether (4 mL) and toluene (80 mL) were added and after cooling to −72° C., zirconium tetrachloride (0.76 g, 3.3 mmol) was added, followed by stirring for 2 hours at room temperature. The obtained reaction solution was once concentrated, extracted with n-hexane, and again concentrated to dryness. After repeating washing with n-hexane and washing with diethyl ether, impurities with low solubility were removed by extraction with toluene to obtain 0.2 g of a racemic form of dichlorodimethylsilylenebis[2-(5-methyl-2-furyl)-4-phenyl-1,5,6,7-tetrahydro-5,5,7,7-tetramethyl-s-indacen-1-yl]zirconium.

$^1$H-NMR (400 MHz, CDCl$_3$) δ 0.98 (s, 6H), 1.09 (s, 12H), 1.16 (s, 6H), 1.20 (s, 6H), 1.76 (s, 4H), 2.36 (s, 6H), 5.94 (s, 2H), 6.16 (s, 2H), 6.26 (s, 2H), 6.7-7.7 (12H).

(Compar. 3-2) Preparation of Catalyst Using Metallocene Complex Y (Catalyst Y)

7.3 g of a solid catalyst (Catalyst Y) was obtained by the same operation as in Example 1 (1-7) except that 63 mg (75 μmol) of Metallocene Complex Y was used in place of Metallocene Complex A.

The prepolymerization magnification (a value obtained by dividing the amount of prepolymerized polymer by the amount of solid catalyst) was 0.44.

(Compar. 3-3) Propylene-Propylene.Ethylene Two-Stage Polymerization by Catalyst Y The operation was performed in the same manner as in Example 1 (1-8) except that the amount of the catalyst was 70 mg, the average gas molar composition in the reactor during the propylene/ethylene polymerization was adjusted to propylene/ethylene=42/58, and the polymerization time was 25 minutes in the second step. As a result, 174 g of a propylene-propylene.ethylene block copolymer was obtained.

In the block copolymer obtained above, from the results of CFC-IR, the rubber content (CP content) was 51 wt %, the ethylene content in rubber (CP) was 55 mol %, and the weight average molecular weight (Mw) of the CP moiety was 656,000. The rubber polymerization activity (CP activity) was 4,000 (g-CP/g-Cat/hr).

Tm of the propylene polymer component (PP) separately collected in the first step was 157° C., MFR was 14 (dg/min), and the PP polymerization activity was 1,600 (g-PP/g-Cat/hr).

The results are shown together in Table 1.

Comparative Examples 4 to 6

Propylene Polymerization by Catalysts W to Y

The operation was performed in the same manner as in Example 12 (12-1) by changing the catalyst to Catalysts W to Y, respectively.

The results are shown together in Table 2.

The polymerization results in Examples 1 to 11 using Metallocene Complexes A, B, C, D, E, F, G, H, I and J and Comparative Examples 1 to 3 using Metallocene Complexes W, X and Y are shown in Table 1.

TABLE 1

| | Metallocene Complex | Catalyst | PP Polymerization Activity (g-PP/g-Cat/hr) | MFR of PP (dg/min.) | Tm of PP (° C.) | Ethylene Composition of Polymerization Gas in Second Step (mol %) | Ethylene Content in CP (mol %) | CP Polymerization Activity (g-CP/g-Cat/hr) | Molecular Weight of CP Moiety (Mw) |
|---|---|---|---|---|---|---|---|---|---|
| Example 1 | A | A | 5,800 | 0.8 | 162 | 43 | 38 | 10,100 | 168,000 |
| Example 2 | B | B | 4,300 | 7.7 | 161 | 56 | 56 | 11,100 | 192,000 |
| Example 3 | C | C | 6,100 | 3.4 | 160 | 46 | 41 | 7,400 | 351,000 |
| Example 4 | D | D | 7,000 | 1.6 | 161 | 55 | 51 | 9,400 | 521,000 |
| Example 5 | E | E | 4,300 | 4.2 | 161 | 51 | 46 | 880 | 305,000 |
| Example 6 | F | F | 8,500 | 4.0 | 161 | 57 | 52 | 7,600 | 544,000 |
| Example 7 | G | G | 15,400 | 3.9 | 160 | 52 | 42 | 12,700 | 622,000 |
| Example 8 | H | H | 1,600 | 7.0 | 158 | 44 | 35 | 10,000 | 447,000 |
| Example 9 | I | I | 7,300 | 0.9 | 162 | 53 | 41 | 5,600 | 765,000 |
| Example 10 | J | J | 9300 | 60 | 161 | 51 | 46 | 5,800 | 777,000 |
| Example 11 | G | K | 28100 | 120 | 159 | 50 | 39 | 14,500 | 602,000 |
| Comparative Example 1 | W | W | 2,200 | 16 | 160 | 59 | 52 | 730 | 513,000 |
| Comparative Example 2 | X | X | 2,100 | 16 | 159 | 41 | 32 | 570 | 730,000 |
| Comparative Example 3 | Y | Y | 1,600 | 14 | 157 | 58 | 55 | 4,000 | 656,000 |

The polymerization results in Examples 12 to 22 using Metallocene Complexes A, B, C, D, E, F, G, H, I and J and Comparative Examples 4 to 6 using Metallocene Complexes W, X and Y are shown in Table 2.

Metallocene Complex Y: Dichlorodimethylsilylenebis[2-(5-methyl-2-furyl)-4-phenyl-1,5,6,7-tetrahydro-5,5,7,7-tetramethyl-s-indacen-1-yl]zirconium

TABLE 2

|  | Metallocene Complex | Catalyst | Amount of Catalyst (mg) | Amount of Hydrogen (ml) | Yield (g) | Polymerization Activity (g-PP/g-Cat/hr) | MFR (dg/min) | Molecular Weight (Mw) | Tm (° C.) |
| --- | --- | --- | --- | --- | --- | --- | --- | --- | --- |
| Example 12 | A | A | 34 | 310 | 292 | 8,600 | 7.3 | 250,000 | 161 |
| Example 13 | B | B | 33 | 300 | 157 | 4,700 | 4.6 | 260,000 | 161 |
| Example 14 | C | C | 33 | 310 | 262 | 7,900 | 5.5 | 261,000 | 159 |
| Example 15 | D | D | 31 | 300 | 222 | 7,100 | 9.9 | 244,000 | 161 |
| Example 16 | E | E | 28 | 300 | 111 | 3,900 | 4.8 | 261,000 | 162 |
| Example 17 | F | F | 29 | 300 | 227 | 7,600 | 3.5 | 290,000 | 161 |
| Example 18 | G | G | 20 | 300 | 299 | 15,000 | 0.9 | 441,000 | 160 |
| Example 19 | H | H | 30 | 320 | 35 | 1,200 | 3.7 | 384,000 | 157 |
| Example 20 | I | I | 19 | 300 | 287 | 15,000 | 6.3 | 268,000 | 162 |
| Example 21 | J | J | 15 | 300 | 213 | 14,200 | 5.6 | 276,000 | 161 |
| Example 22 | G | K | 10 | 300 | 115 | 11,500 | 5.1 | 289,000 | 159 |
| Comparative Example 4 | W | W | 50 | 200 | 127 | 2,500 | 24 | 181,000 | 160 |
| Comparative Example 5 | X | X | 35 | 300 | 96 | 2,800 | 38 | 155,000 | 159 |
| Comparative Example 6 | Y | Y | 70 | 300 | 72 | 1,000 | 2.4 | 332,000 | 157 |

Complex:

Metallocene Complex A: Dichlorosilacyclobutylenebis[2-(5-methyl-2-furyl)-4-phenyl-1,5,6,7-tetrahydro-s-indacen-1-yl]zirconium Metallocene Complex B: Dichlorosilacyclopentylenebis[2-(5-methyl-2-furyl)-4-phenyl-1,5,6,7-tetrahydro-s-indacen-1-yl]zirconium Metallocene Complex C: Dichlorosilacyclobutylenebis[2-(5-methyl-2-furyl)-4-phenyl-5,6-dimethyl-1-indenyl]zirconium Metallocene Complex D: Dichlorosilacyclobutylenebis[2-(4,5-dimethyl-2-furyl)-4-phenyl-5,6-dimethyl-1-indenyl]zirconium Metallocene Complex E: Dichlorosilacyclobutylenebis[2-(5-tert-butyl-2-furyl)-4-phenyl-5,6-dimethyl-1-indenyl]zirconium Metallocene Complex F: Dichlorosilacyclobutylenebis[2-(5-methyl-2-furyl)-4-(3,5-dimethylphenyl)-5,6-dimethyl-1-indenyl]zirconium Metallocene Complex G: Dichlorosilacyclobutylenebis[2-(5-methyl-2-furyl)-4-(4-tert-butylphenyl)-5,6-dimethyl-1-indenyl]zirconium Metallocene Complex H: Dichlorosilacyclobutylenebis[2-(5-methyl-2-furyl)-4-phenyl-1,5,6,7-tetrahydro-5,5,7,7-tetramethyl-s-indacen-1-yl]zirconium Metallocene Complex I: Dichlorosilacyclobutylenebis[2-(5-methyl-2-furyl)-4-(2,6-dimethyl-4-biphenylyl)-5, 6-dimethyl-1-indenyl]zirconium Metallocene Complex J: Dichlorosilacyclobutylenebis[2-(4,5-dimethyl-2-furyl)-4-(4-tert-butyl-phenyl)-5,6-dimethyl-1-indenyl]zirconium Metallocene Complex W: Dichlorodimethylsilylenebis[2-(5-methyl-2-furyl)-4-phenyl-1,5,6,7-tetrahydro-s-indacen-1-yl]zirconium Metallocene Complex X: Dichlorodimethylsilylenebis[2-(5-methyl-2-furyl)-4-phenyl-5,6-dimethyl-1-indenyl]zirconium As apparent from the polymerization results of Table 1, compared with conventional metallocene catalysts, the metallocene complex of the present invention and the catalyst containing it can polymerize a PP polymer component and a CP component with high activity while maintaining a high ethylene uptake efficiency, and furthermore, it is apparent from Table 2 that in the homopolymerization of propylene, a homopolypropylene having a high melting point can be produced with high activity While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2014-057557) filed on Mar. 20, 2014, the contents of which are incorporated herein by way of reference.

INDUSTRIAL APPLICABILITY

According to the metallocene complex, the catalyst containing the same, and the production method of an olefin polymer of the present invention, a propylene component and a rubber component can be polymerized with high activity and a propylene-propylene.(ethylene or α-olefin) block copolymer with the rubber moiety having a high ethylene or α-olefin content can be efficiently produced. In the homopolymerization of propylene, a homopolypropylene having a high melting point can also be produced. Thus, the present invention is very useful.

The invention claimed is:

1. A metallocene complex represented by the following formula [I]:

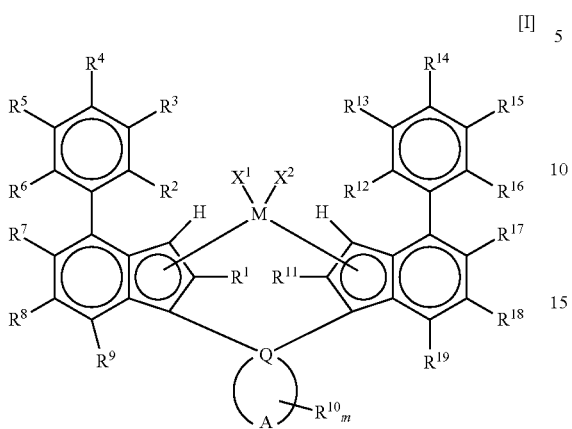

in which M is Ti, Zr, or Hf;

Q is a carbon atom, a silicon atom, or a germanium atom;

each of $X^1$ and $X^2$ is independently a halogen atom, an alkyl group having a carbon number of 1 to 6, an aryl group having a carbon number of 6 to 18, an amino group substituted with an alkyl group having a carbon number of 1 to 6, an alkoxy group having a carbon number of 1 to 6, a halogen-containing alkyl group having a carbon number of 1 to 6, or a halogen-containing aryl group having a carbon number of 6 to 18;

$R^1$ and $R^{11}$ are the same or different and are a hydrogen atom, an alkyl group having a carbon number of 1 to 6, an alkoxy group having a carbon number of 1 to 6, a furyl group, a thienyl group, a furyl group having a substituent, or a thienyl group having a substituent, and one or both of $R^1$ and $R^{11}$ are selected from a furyl group, a thienyl group, a furyl group having a substituent, or a thienyl group having a substituent;

$R^7$ and $R^{17}$ are the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18, and when either one of $R^7$ or $R^{17}$ is a hydrogen atom, the other is a substituent except for a hydrogen atom;

$R^8$ and $R^{18}$ are the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18;

adjacent substituents out of $R^7$, $R^8$, $R^{17}$, and $R^{18}$ are optionally bonded together to form a 5- to 7-membered ring, and the 5- to 7-membered ring optionally contains an unsaturated bond;

$R^2$, $R^3$, $R^4$, $R^5$, $R^6$, $R^9$, $R^{12}$, $R^{13}$, $R^{14}$, $R^{15}$, $R^{16}$, and $R^{19}$ are the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a trialkylsilyl group-containing alkyl group having a carbon number of 1 to 6, an aryl group having a carbon number of 6 to 18, a halogen-containing aryl group having a carbon number of 6 to 18, a furyl group, a thienyl group, a furyl group having a substituent, or a thienyl group having a substituent;

adjacent substituents out of $R^2$, $R^3$, $R^4$, $R^5$, $R^6$, $R^{12}$, $R^{13}$, $R^{14}$, $R^{15}$, and $R^{16}$ are optionally bonded together to form a 5- to 7-membered ring, and the 5- to 7-membered ring optionally contains an unsaturated bond;

A is a divalent hydrocarbon group having a carbon number of 3 to 12 and forming a ring together with Q to which it is bonded, and optionally contains an unsaturated bond;

$R^{10}$ is a substituent on A and is an alkyl group having a carbon number of 1 to 6, a halogen-containing alkyl group having a carbon number of 1 to 6, a trialkylsilyl group-containing alkyl group having a carbon number of 1 to 6, a silyl group containing a hydrocarbon group having a carbon number of 1 to 6, an aryl group having a carbon number of 6 to 18, or a halogen-containing aryl group having a carbon number of 6 to 18; and m represents an integer of 0 to 24, and when m is 2 or more, $R^{10}$s optionally combine with each other to form a new ring structure.

2. The metallocene complex according to claim 1, wherein in the formula [I], $R^7$ and $R^{17}$ are optionally the same or different and are selected from alkyl groups having a carbon number of 1 to 6.

3. The metallocene complex according to claim 1, wherein in the formula [I], $R^8$ and $R^{18}$ are optionally the same or different and are selected from alkyl groups having a carbon number of 1 to 6.

4. The metallocene complex according to claim 1, wherein in the formula [I], A is a divalent hydrocarbon group having a carbon number of 3 to 6 and forms a 4- to 7-membered ring, and m is an integer of 0 to 6.

5. The metallocene complex according to claim 1, wherein in the formula [I], $R^2$, $R^6$, $R^9$, $R^{12}$, $R^{16}$ and $R^{19}$ is each a hydrogen atom.

6. The metallocene complex according to claim 1, wherein the formula [I] is represented by the following formula [II]:

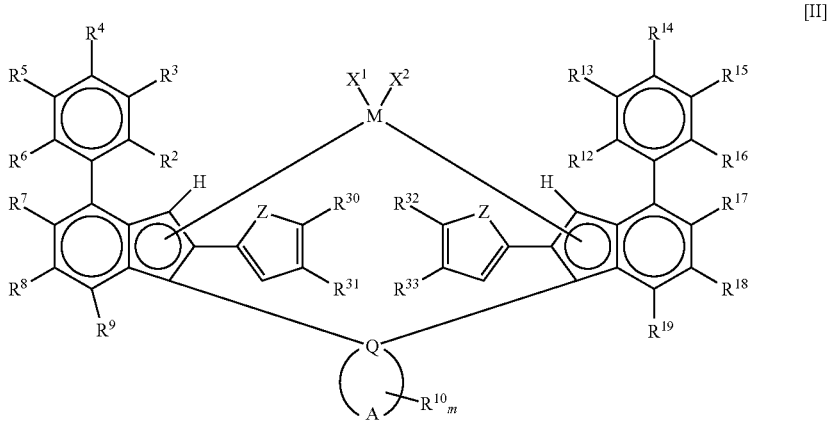

in which Z is an oxygen atom or a sulfur atom,
$R^{30}$, $R^{31}$, $R^{32}$, and $R^{33}$ are optionally the same or different and are a hydrogen atom, a halogen atom, an alkyl group having a carbon number of 1 to 6, an alkoxy group having a carbon number of 1 to 6, a halogen-containing alkyl group having a carbon number of 1 to 6, a silyl group containing a hydrocarbon group having a carbon number of 1 to 6, or an aryl group having a carbon number of 6 to 18, adjacent substituents out of $R^{30}$, $R^{31}$, $R^{32}$, and $R^{33}$ are optionally bonded together to form a 5- to 7-membered ring, the 5- to 7-membered ring optionally contains an unsaturated bond, and each of M, $X^1$, $X^2$, Q, $R^2$ to $R^{10}$, $R^{12}$ to $R^{19}$, and m has the same meaning as in formula [I].

7. A catalyst for olefin polymerization, comprising the metallocene complex according to claim 1.

8. A catalyst for olefin polymerization, comprising each of the following components (A), (B), and (C):
component (A): the metallocene complex according to claim 1,
component (B): a compound reacting with the component (A) to form an ion pair, or an ion-exchange layered silicate, and
component (C): an organoaluminum compound.

9. The catalyst for olefin polymerization according to claim 8, wherein the component (B) is an ion-exchange layered silicate.

10. A method for producing an olefin polymer, comprising performing a polymerization or copolymerization of olefin by using the catalyst for olefin polymerization according to claim 7.

11. A method for producing a propylene-based polymer by using the catalyst for olefin polymerization according to claim 7, comprising:
(i) polymerizing propylene in a ratio of 90 to 100 wt % and ethylene or α-olefin in a ratio of 0 to 10 wt %, relative to all monomer components; and
(ii) polymerizing propylene in a ratio of 10 to 90 wt % and ethylene and/or α-olefin having a carbon number of 4 or more in a ratio of 10 to 90 wt %, relative to all monomer components.

12. A method for producing a propylene-based polymer by using the catalyst for olefin polymerization according to claim 7, comprising:
(i) polymerizing propylene in a ratio of 90 to 100 wt % and ethylene or α-olefin in a ratio of 0 to 10 wt %, relative to all monomer components, by bulk polymerization using propylene as a solvent or gas phase polymerization of maintaining the monomers in a gas state; and
(ii) gas phase polymerizing propylene in a ratio of 10 to 90 wt % and ethylene or α-olefin in a ratio of 10 to 90 wt %, relative to all monomer components.

* * * * *